US011627985B2

(12) United States Patent
Worrel

(10) Patent No.: US 11,627,985 B2
(45) Date of Patent: Apr. 18, 2023

(54) SURGICAL DEVICES AND DEPLOYMENT APPARATUSES

(71) Applicant: SUREMKA, LLC, Dallas, TX (US)

(72) Inventor: Daniel A. Worrel, Dallas, TX (US)

(73) Assignee: SUREMKA, LLC, Dallas, TX (US)

( * ) Notice: Subject to any disclaimer, the term of this patent is extended or adjusted under 35 U.S.C. 154(b) by 32 days.

(21) Appl. No.: 16/877,042

(22) Filed: May 18, 2020

(65) Prior Publication Data

US 2020/0281625 A1 Sep. 10, 2020

Related U.S. Application Data

(63) Continuation-in-part of application No. 16/505,093, filed on Jul. 8, 2019, which is a continuation-in-part of application No. 15/626,431, filed on Jun. 19, 2017, now Pat. No. 10,342,577, which is a continuation-in-part of application No. 14/300,755, filed on Jun. 10, 2014, now Pat. No. 10,258,368.

(60) Provisional application No. 62/849,836, filed on May 17, 2019.

(51) Int. Cl.
*A61B 17/34* (2006.01)
*A61B 17/02* (2006.01)
*A61B 17/00* (2006.01)

(52) U.S. Cl.
CPC ...... *A61B 17/3423* (2013.01); *A61B 17/0218* (2013.01); *A61B 2017/00871* (2013.01); *A61B 2017/3445* (2013.01)

(58) Field of Classification Search
CPC ........ A61B 17/3423; A61B 2017/3445; A61B 2017/3488
See application file for complete search history.

(56) References Cited

U.S. PATENT DOCUMENTS

| | | | | |
|---|---|---|---|---|
| 3,397,699 | A * | 8/1968 | Kohl | A61M 25/04 29/451 |
| 5,279,564 | A * | 1/1994 | Taylor | A61B 17/34 606/198 |
| 5,309,894 | A * | 5/1994 | Heckele | A61B 17/34 600/101 |
| 5,971,960 | A * | 10/1999 | Flom | A61B 17/3417 604/174 |
| 6,228,063 | B1 * | 5/2001 | Aboul-Hosn | A61B 17/3423 604/174 |
| 6,565,536 | B1 * | 5/2003 | Sohn | A61M 25/0082 604/174 |

(Continued)

*Primary Examiner* — Jenna Zhang

(57) ABSTRACT

Surgical devices having a plurality of outwardly-biased flexible fins capable of both inward convergence and outward flexion, provide for fluid retention and soft tissue retraction during surgical procedures. The outwardly-biased flexible fins also provide for soft tissue compression, decreasing the length of the lumen or passageway through which instruments pass, allowing for a wider range of movement of instruments and better access to the surgical site, especially in patients with greater amounts of fat tissue that would otherwise require longer lumen lengths in prior art endoscopic cannulas. An obturator assembly including a cannulated handle member with a cannulated shaft attached to said handle member, said shaft extending distally and terminating at a cannulated obturator tip. A hood structure found on such obturator tip may be used to secure one or more flexible fins prior to deployment.

5 Claims, 64 Drawing Sheets

(56) References Cited

U.S. PATENT DOCUMENTS

| | | | |
|---|---|---|---|
| 6,929,621 B2* | 8/2005 | Whitmore | A61M 25/0069 |
| | | | 604/177 |
| 8,679,151 B2* | 3/2014 | Rodrigues, Jr. | A61B 17/0218 |
| | | | 606/208 |
| 2006/0129165 A1* | 6/2006 | Edoga | A61B 17/3423 |
| | | | 604/174 |
| 2008/0242930 A1* | 10/2008 | Hanypsiak | A61B 17/3421 |
| | | | 600/114 |
| 2010/0249517 A1* | 9/2010 | Fischvogt | A61B 17/3421 |
| | | | 600/204 |
| 2011/0034775 A1* | 2/2011 | Lozman | A61B 17/1684 |
| | | | 600/204 |
| 2011/0092912 A1* | 4/2011 | Li | A61J 15/0015 |
| | | | 604/175 |
| 2012/0130182 A1* | 5/2012 | Rodrigues, Jr. | A61B 17/0218 |
| | | | 600/206 |

* cited by examiner

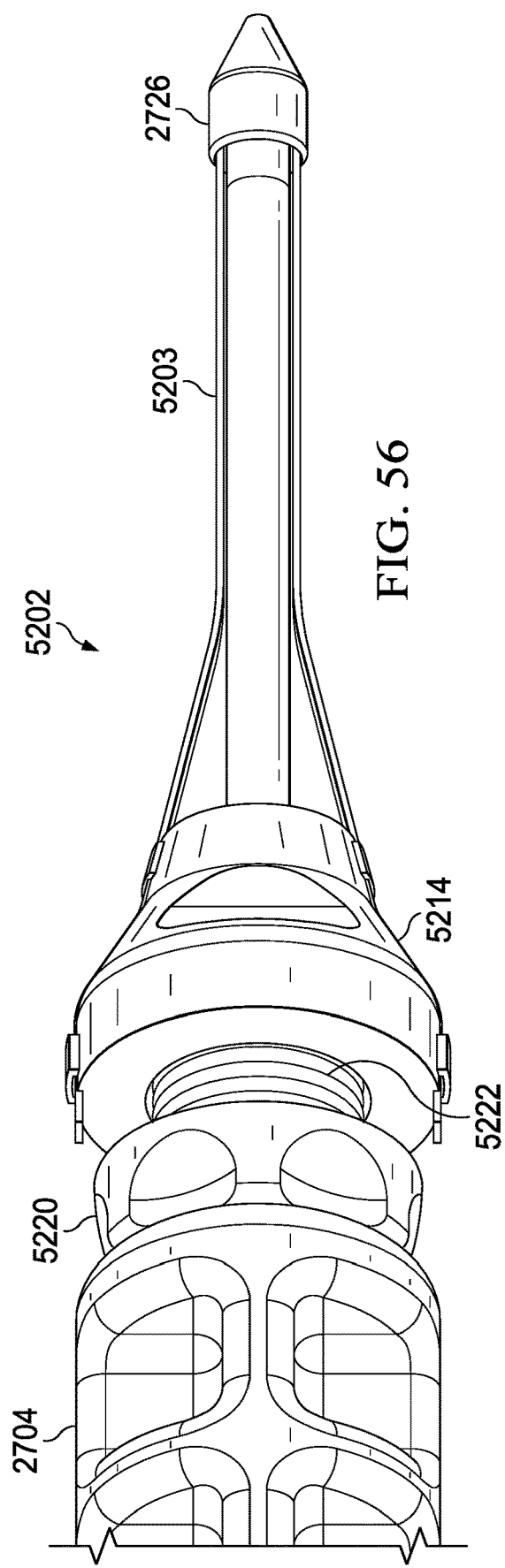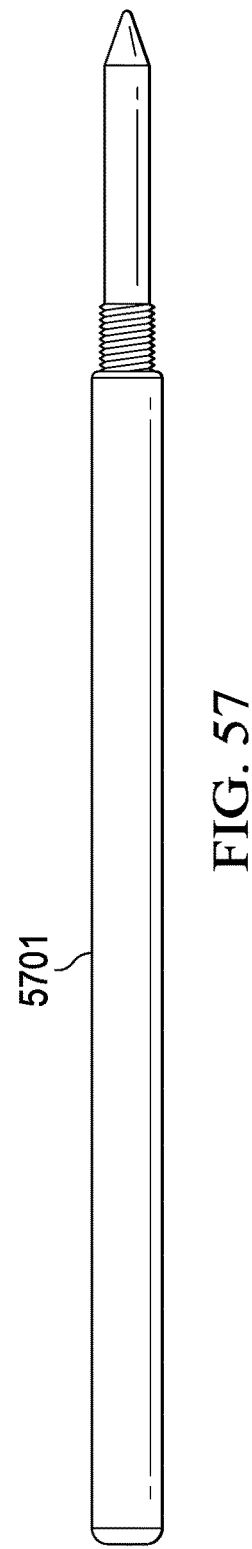

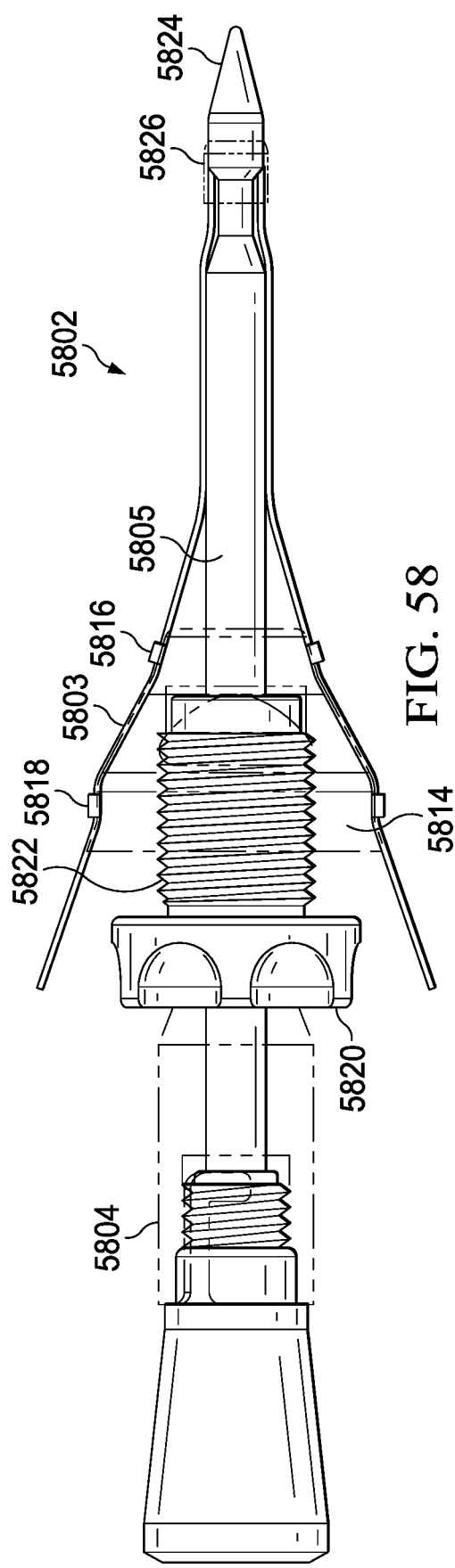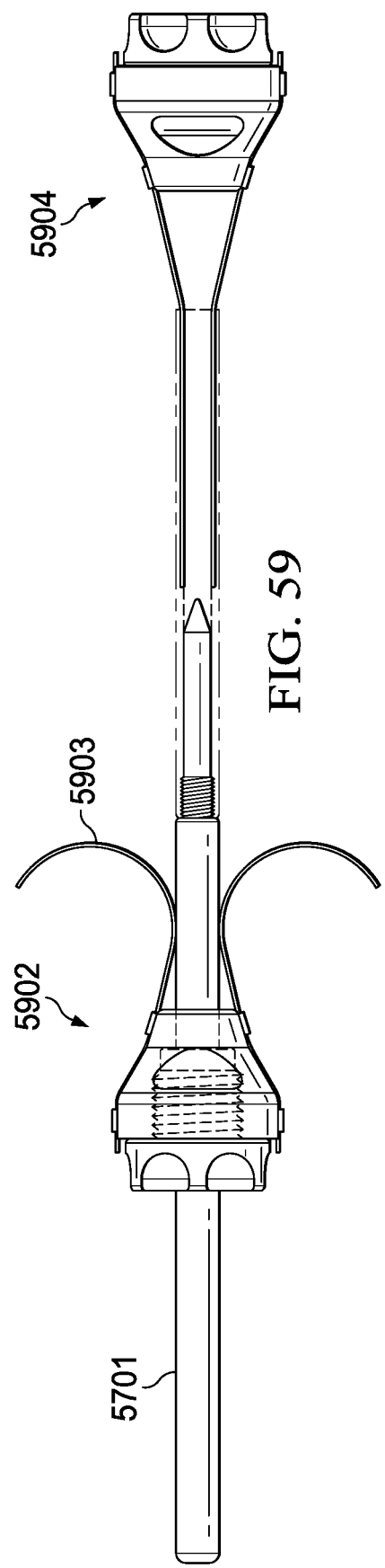

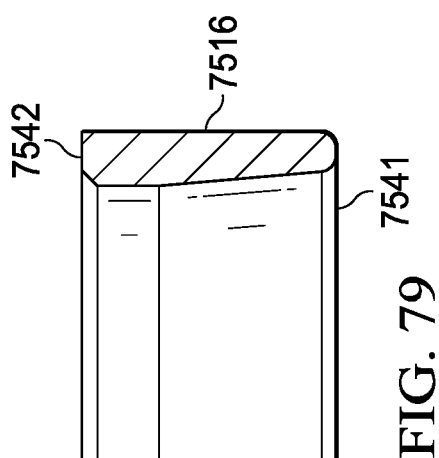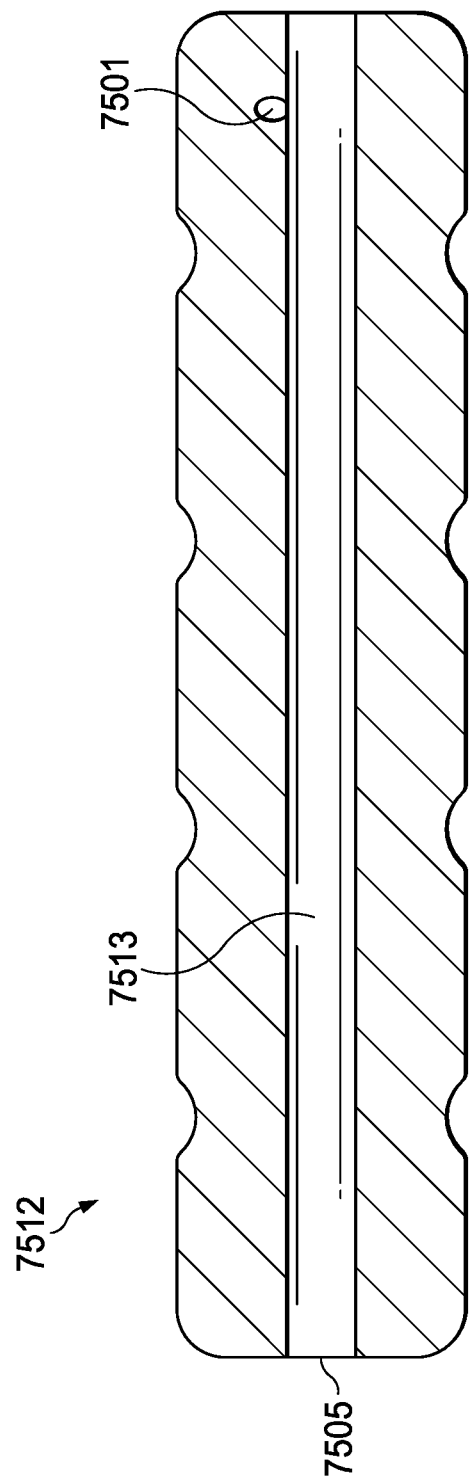
FIG. 79
FIG. 80

SURGICAL DEVICES AND DEPLOYMENT APPARATUSES

BACKGROUND OF THE INVENTION

1. Field of the Invention

The present invention relates to devices for performing percutaneous arthroscopic and other endoscopic or laparoscopic surgeries and, more specifically, to surgical devices such as cannula devices and "portal holder devices" for forming a surgical port, as well as apparatuses for deploying such surgical devices into a surgical site. The surgical devices disclosed herein, utilizing outwardly biased fins, work to limit fluid leakage and to provide soft tissue retraction and compression to improve visualization during surgery. This concept utilizes, in addition to the features of the devices discussed herein, the inherent soft tissue and hydrostatic pressure to limit leakage. Numerous open (non-arthroscopic) applications also exist for these inventions in that the low-profile insertion of the biased fins improves surgical exposure and visualization. In open applications, the biasing fins have greater divergence for direct visualization.

2. Description of Related Art Including Information Disclosed Under 37 CFR 1.97 and 1.98

Traditional minimally-invasive arthroscopic surgeries are performed using a cannula device to penetrate small incisions in the patient's skin and outer tissue, creating a port through which surgical tools may be passed to allow access to the underlying structure of interest. For example, in shoulder arthroscopy, the procedure is performed through "portals" in the patient's skin. These portals are formed from small incisions, generally about ½ of an inch to an inch long in the skin, and are located over particular areas of the joint that the surgeon will need to operate upon. Cannulas are then inserted into the portals so that instruments can easily be placed in the shoulder joint. Shoulder arthroscopy itself involves inserting a specially designed video camera with a fiber optic light source into the shoulder joint so that the anatomic structures of the joint can be seen. Instruments that have been specially designed to remove inflamed tissue, attach sutures to bone, and repair torn tendons and ligaments are then used to operate inside the shoulder.

The area between the skin tissue and shoulder joint is quite small. Consequently, it is necessary to "inflate" the area by pumping an irrigation fluid (e.g. saline) into the joint under pressure. In laparoscopic surgical procedures, carbon dioxide in gaseous form may be utilized as an insufflating agent to perform a similar function. The pressure produced by the irrigation fluid pushes the tissue outward from the joint and allows greater room for manipulation of the arthroscopic camera and other surgical tools. However, the actual working angle of the tools is ultimately determined by the length and inner diameter of the cannula. Heavy patients or patients with large amounts of skin and other tissue covering the joint require a longer cannula to penetrate the tissue sufficiently for the procedure. This increased cannula length decreases the working angle of the tools at the joint, limiting the ability of the surgeon to perform the procedure. Although this angle may be improved by increasing the inner diameter of the cannula, there are realistic limits on the useable diameter. For example, the diameter can only be increased by a small amount or else it would effectively eliminate any benefit of conducting the arthroscopic procedure as the portal size could become the equivalent of a large incision as performed in traditional surgery.

The aforementioned irrigation fluid and/or gases pumped into a joint during a surgical procedure must remain sealed within said joint to maintain sufficient pressure and space for the movement of surgical instruments. Various devices and techniques have been employed in the prior art to maintain such seal. Most typically, a series of annular seals mounted within a cannula, at an end of said cannula proximal to the patient, serve to prevent leakage of fluid out of the joint during a surgical procedure. However, the usage of such annular seals for fluid retention has drawbacks in that undesirable leakage tends to occur as surgical instruments passing through the cannula are manipulated during a procedure. Further undesired leakage also tends to occur upon the insertion and/or removal of surgical instruments to/from the cannula during a procedure.

What is needed is a surgical portal device that is capable of retracting the tissue through which it penetrates, that is relatively simple to insert and remove so as to minimize tissue damage to the patient, that includes a novel means for incorporating a shape memory alloy into its design that is easy to store, use, remove, and reuse (or dispose of), and that provides for enhanced fluid retention. What is further needed are devices and apparatuses that are specially configured to deploy such surgical cannula and portal devices during surgery, such that the apparatuses have a minimal cross-sectional area and thus are less likely to cause damage while passing from an incision point to a surgical site. The surgical cannula devices, portal devices, and deployment tools disclosed herein satisfies these needs and others as will become apparent to one of ordinary skill after a careful study of the detailed description and embodiments.

BRIEF DESCRIPTION OF THE SEVERAL VIEWS OF THE DRAWINGS

The present invention will be more fully understood by reference to the following detailed description of the preferred embodiments of the present invention when read in conjunction with the accompanying drawings, wherein:

FIG. 28 depicts a perspective view of the alternate embodiments on the cannula device (2002) and trocar device (2704) shown in FIG. 27;

FIG. 56 depicts a partial perspective view of the alternate embodiment of the portal holder device, deployment plug, and trocar device as shown in FIG. 52;

FIG. 57 depicts an alternate embodiment of a trocar device usable to deploy embodiments of the portal holder device during surgery;

FIG. 58 depicts a side view of a further alternate embodiment of a portal holder device and deployment plug mounted to an embodiment of a trocar device for use during surgery;

FIG. 59 depicts a side view of a further alternate embodiments of portal holder devices removably mounted to opposing sides of an embodiment of a trocar device, for use during surgery;

FIG. 79 depicts a cross-sectional view of the tip sleeve of the embodiment of a cannulated obturator assembly having a selectable length shaft depicted in FIG. 76;

FIG. 80 depicts a cross-sectional view of the cannulated obturator handle of the embodiment of a cannulated obturator assembly having a selectable length shaft as appearing in FIG. 76;

Figure 1:
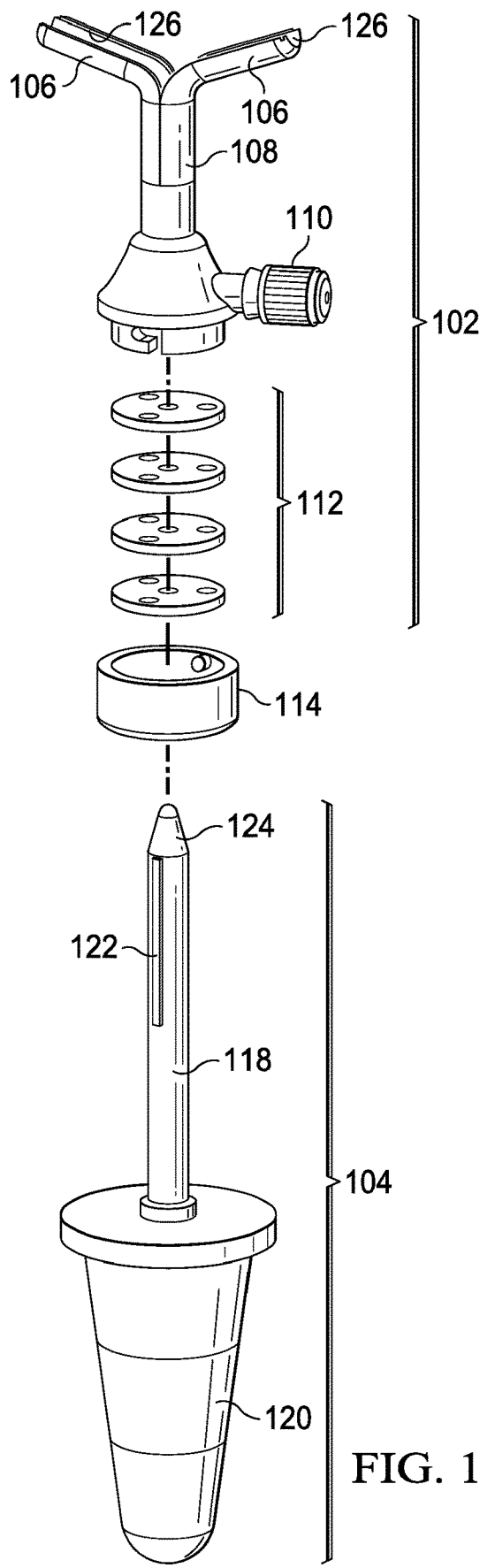
FIG. 1 is an exploded view of a first embodiment of the cannula invention.

The above figures are provided for the purpose of illustration and description only, and are not intended to define the limits of the disclosed invention. Use of the same reference number in multiple figures is intended to designate the same or similar parts. Furthermore, if and when the terms "top," "bottom," "first," "second," "upper," "lower," "height," "width," "length," "end," "side," "horizontal," "vertical," and similar terms are used herein, it should be understood that these terms have reference only to the structure shown in the drawing and are utilized only to facilitate describing the particular embodiment. The extension of the figures with respect to number, position, relationship, and dimensions of the parts to form the preferred embodiment will be explained or will be within the skill of the art after the following teachings of the present invention have been read and understood.

DETAILED DESCRIPTION OF THE INVENTION

FIG. 1 depicts an exploded view of a first embodiment of the cannula invention. As shown in this figure, the complete apparatus includes a cannula device (102) and a trocar device (104). The trocar device (104) includes a handle (120) at its proximal end with a shaft member (118) extending therefrom to form a distal end with a defined tip (124). Along the shaft are multiple raised members (122) that protrude essentially radially from the axial center of the shaft (118) and that extend longitudinally along the shaft length. The raised members (122) in the present embodiment are depicted as extending approximately one half of the length of the shaft (118) near the distal end. However, the length of the raised members (122) may vary in other embodiments. For example, the raised members (122) in another embodiment may be wider than they are in length. Such alternate lengths are within the scope of the present invention. The raised member (122) of the embodiment, as depicted, is also a single element. However, in another embodiment the raised member may be split in two portions such that, on the whole, the raised member (122) may still engage the corresponding slot.

The present embodiment of the cannula device (102) includes body member (108) having a proximal end and a distal end. The body member (108) is essentially cylindrical in shape, having a lumen extending from end to end. Although the body member in the present embodiment is essentially cylindrical in shape, other embodiments may have a geometric cross-sectional shape other than circular, or may include a mix of circular and other geometric shape such as a circular lumen cross section with a geometric outer wall cross section or vice versa. The outer wall may also include a ribbed, grooved, or helical raised feature (or even a recessed feature) that assists the device in gripping a patient's skin and muscle tissue for device retention. Such alternate embodiments are envisioned and are within the scope of the present invention.

The proximal end includes a fluid drain port (110) and a proximal collar (114) that retains several silicon discs (112) that are used as fluid seals through which surgical instruments may pass. The proximal collar (114) attaches to the proximal end of the body member for positive retention of the silicon discs (112). The drain port (110) allows for fluid management during surgical procedures in the same fashion as conventional cannula devices.

The distal end of the body member (108) includes a plurality of flexible, yet semi-rigid fins (106) that are formed in the outwardly-biased position (as shown in FIG. 1) during injection molding of the device. The present embodiment utilizes medical grade polymers during the injection molding or extrusion process. These polymers allow the fins to retain the outwardly-biased shape at normal operating temperatures for the device, yet also allow the fins to flex inwardly when sufficient pressure is applied. For example, polyurethanes such as Hytrel® or Arnitel® may be utilized due to the desired durability characteristics, or polyvinyl chloride ("PVC") if expense is a concern.

Figure 3:
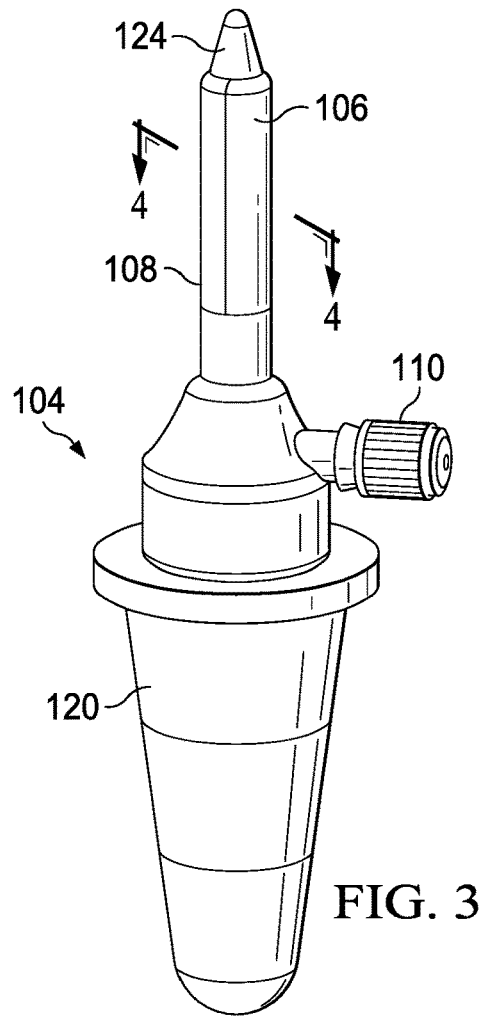
FIG. 3 is an assembled view of the embodiment, highlighting a cross sectional area.

Each fin (106) of the present embodiment includes a radius of curvature that approximates that of the wall of the body member (108) that forms the lumen. When the fins (106) are forcibly moved to the inward position (as depicted in FIG. 3), the inner surface of the fins essentially extends the lumen of the body member (108) to the distal end of the fins. Further, because the fins have a wall thickness, each fin features an edge surface that extends from the fin inner surface to the fin outer surface. It is the edge surface of the fin that contacts the edge surface of the adjacent fin when the fins are in the inward-most position (as in FIG. 3).

Figure 2:
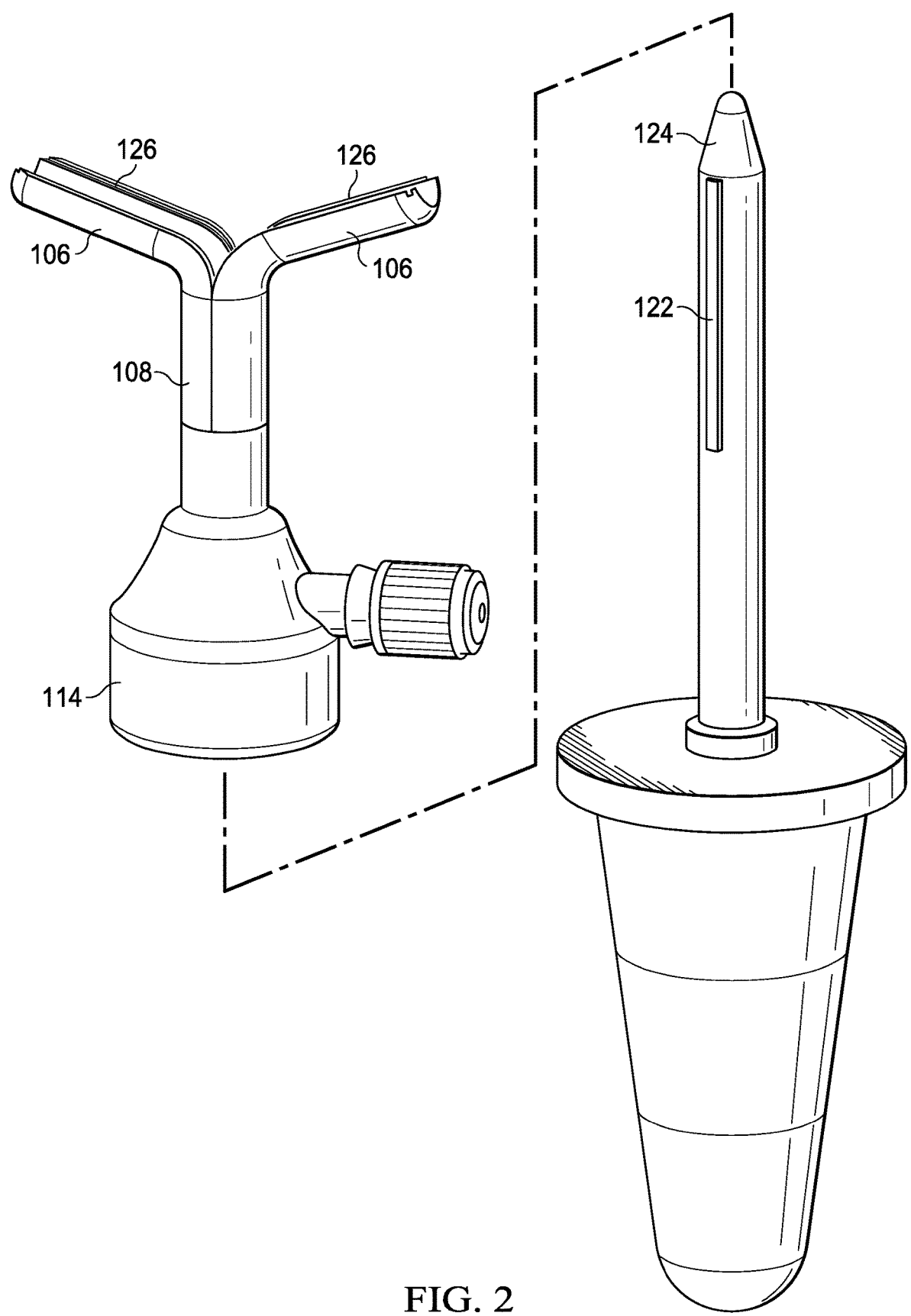
FIG. 2 is a depiction of the cannula invention prior to insertion of the trocar device.

FIG. 2 depicts the cannula invention prior to insertion of the trocar device. As shown, the tip (124) of the trocar device is inserted through the cannula device proximal collar (114) such that the raised members (122) engage with complimentary slots formed within the body member (108) of the cannula device. These complimentary slots extend a distance within the cannula device lumen and along the edge surfaces of the fins (106). This embodiment features two corresponding slots (126), one for each fin. Other embodiments may utilize a greater number of fins and, consequently, would require a correspondingly greater number of slots. For example, an embodiment with three outwardly-biased fins would have three pairs of adjacent fin edge surfaces. Such an embodiment would require three slots within the cannula body member and three corresponding complimentary raised members on the trocar device.

FIG. 3 depicts an assembled view of the embodiment as it would be configured for use once the trocar device (104) is inserted into the cannula device body member (108). As shown, insertion of the trocar device (104) engages the slots within the fins (106), causing the fins (106) to move inward against the outward bias pressure that is normally present. In the full inward position the edge surfaces of the fins (106) meet. This figure also highlights a cross sectional area, which is shown in detail in FIG. 4.

Figure 4:
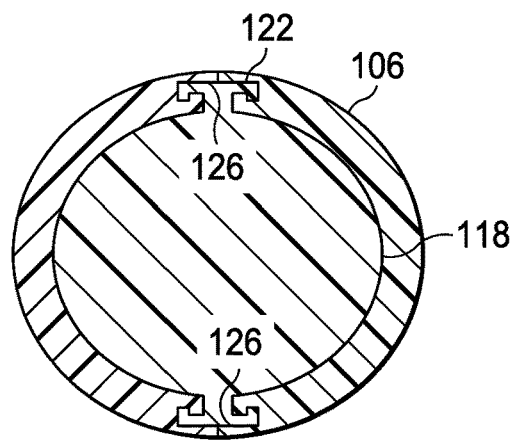
FIG. 4 is a cross section of the working end of the invention as in the assembled view of the embodiment.

The cross-section detail depicted in FIG. 4 demonstrates how the trocar shaft member (118) fits within the cannula lumen and engages the complementary slots in the fins (106). In this embodiment, the cannula device has two fins. Formed within the inner wall of the body member are two slots, each having a cross section that resembles a serif font capital letter "T". This slot extends the length of the body member inner wall and is aligned with the origin of the edge surfaces of the fins (106) as they extend from the body member, and accepts a corresponding serif font capital letter "T" shaped raised member (122) on the trocar.

A corresponding portion of the "T" slot is formed in the wall of each fin at the junction of the edge surface and the inner surface. When the fins (106) are in the inward most (or "closed") position (as shown in FIG. 3), the adjoining fin edge surfaces (126) meet and complete the overall "T" slot such that it extends from the body member to the distal end of the fins. Although the corresponding "T" slot portion in the fin edge surfaces (126) extends approximately the entire length of the fin in the present embodiment, other embodiments may extend less than the entire length of the fin.

To prepare the embodiment for use with a patient, the trocar device is inserted into the cannula device lumen such that raised members (122) engage the corresponding and complimentary body member "T" slots. As the trocar shaft (118) is further inserted into the lumen, the raised members slide within the "T" slots until they reach the origin of the edge surfaces of the fins (106). As the trocar is further inserted, the raised members apply stress to the corresponding "tail" elements of "T" slot portions in each fin edge surface (126) causing the fins to move inward and come together along adjacent edge surfaces. This has the effect of "zipping" the fin edges together for insertion of the device into a patient.

Although a serif capital "T" shaped slot cross section is discussed, other embodiments may utilize cross-sectional slot shapes that provide an elemental feature that positively engages and accepts compressive stresses from the corresponding elements of the raised members to cause the fins to move inward and come together along adjacent edge surfaces as the trocar is inserted. Each fin edge surface may include a slot that features a cavity that is larger than the opening formed in the edge surface, with additional material removed from the edge surface where it intersects with the fin inner surface to allow for the corresponding raised member to pass therebetween. For example, the edge surface may have a longitudinal slot formed therein that has a dovetail cross-section. The corresponding raised member would include two corresponding dovetail pin features to engage the adjacent dovetail slots in the adjacent fin edge surfaces. Each fin edge surface may also include a slot with a formed cavity that turns inward towards the inner surface, outward towards the outer surface, or both, such that the slot opening in the edge surface is not aligned with the deepest portion of the slot cavity. For example, the edge surface may have a longitudinal slot that is formed such that cavity beneath the slot opening is centered toward the inner surface and does not share the exact centerline of the cavity opening. Again, the trocar device would include a corresponding raised member that engages the slot as before. In yet another embodiment it is also possible to have a plurality of slots, with each slot having a different geometric cross sectional shape.

Figure 5:
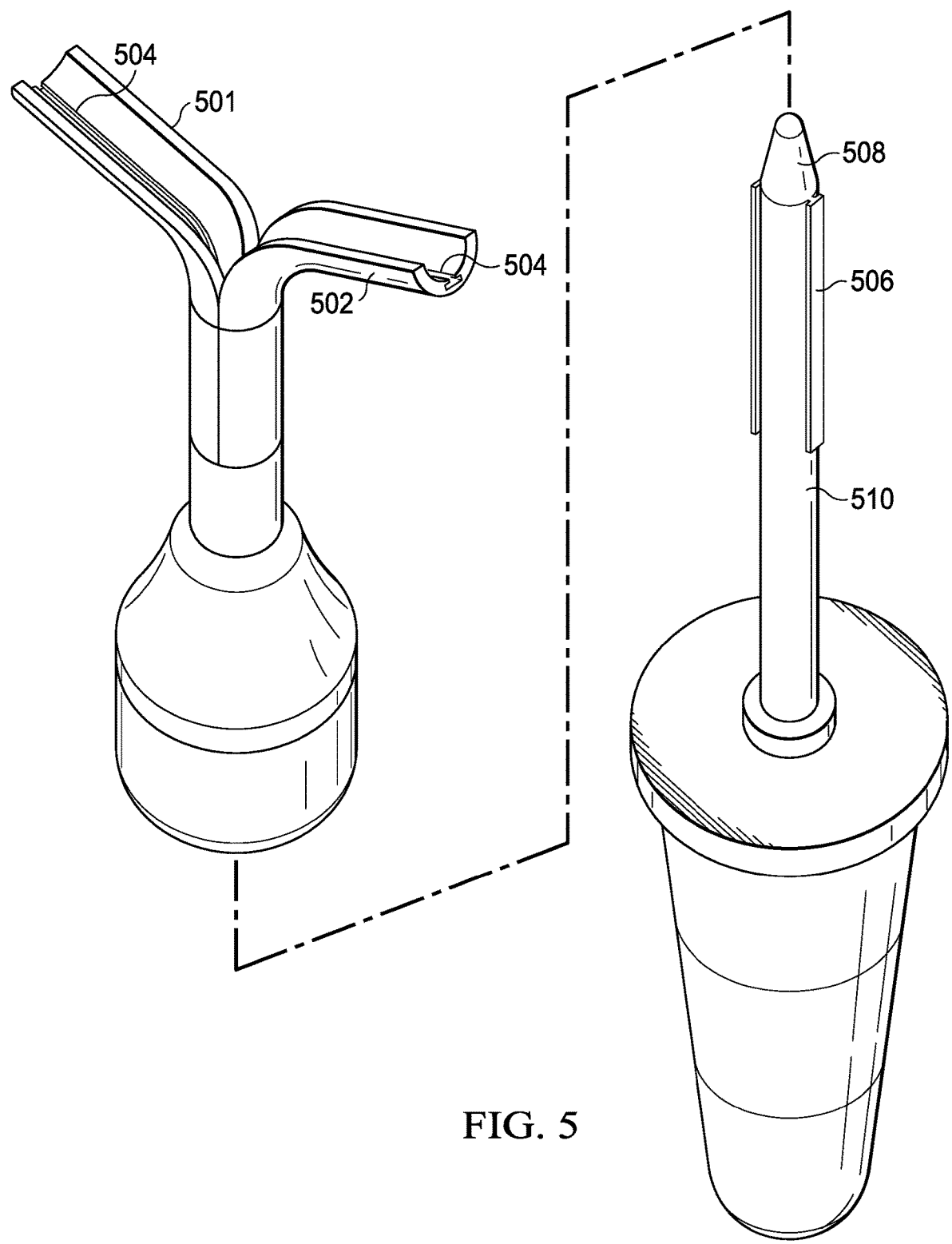
FIG. 5 is a depiction of an alternative embodiment of the cannula invention prior to insertion of the trocar device.
Figure 6:
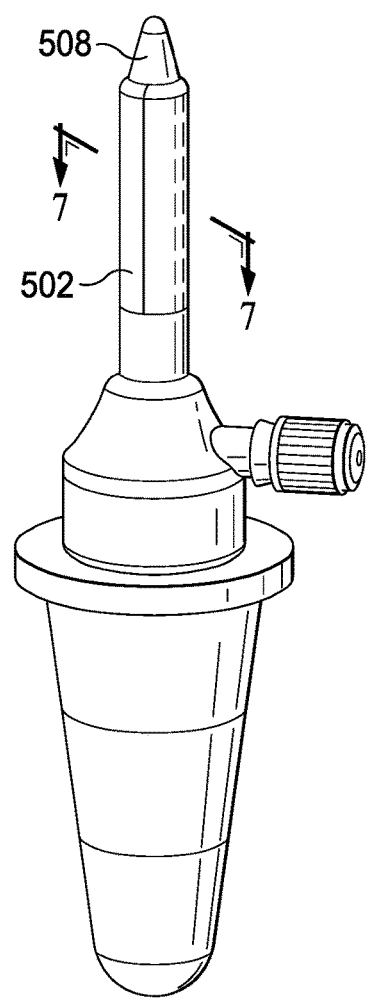
FIG. 6 is an assembled view of the alternative embodiment, highlighting a cross-sectional area.

FIG. 5 depicts an alternative embodiment of the cannula invention prior to insertion of the trocar device. As shown, the trocar device has a shaft member (510) with raised members (506) and a distal tip (508). However, in this embodiment the corresponding slots (504) in the cannula device are formed such that they extend from the proximal opening and along the inner wall of the body member and along the inner wall of the fins (502) at some point between each fin's edge surface (501). Insertion of the trocar device into the cannula device, once again, causes the flexible outwardly-biased fins (502) to move inward such that adjacent fin edge surfaces (501) meet and the closed fins essentially form an extension of the body member as shown in FIG. 6. In this figure, the device is again ready for insertion into a patient.

Figure 8:
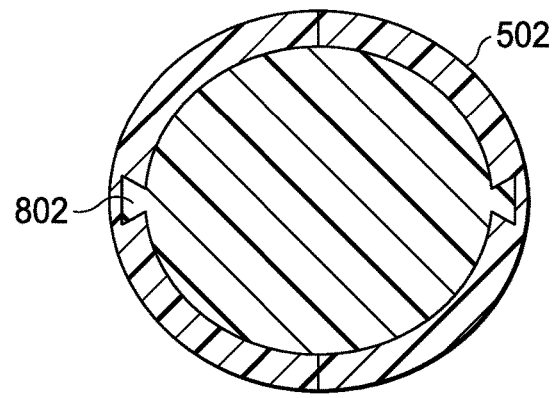
FIG. 8 is a cross section of the working end highlighting an alternative dovetail channel shape.
Figure 9:
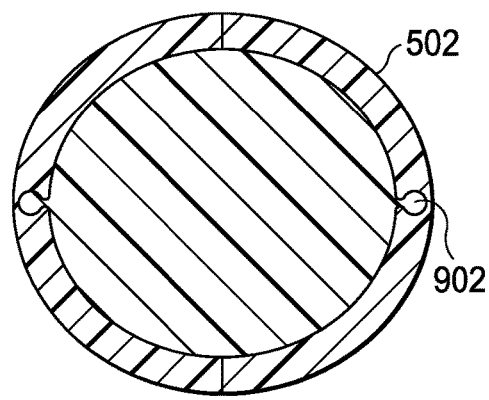
FIG. 9 is a cross section of the working end highlighting an alternative circular channel shape.
Figure 7:
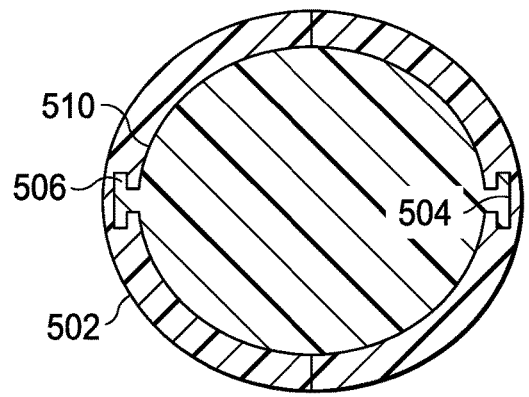
FIG. 7 is a cross section of the working end of the invention as in the assembled view of the alternative embodiment.

FIG. 6 depicts an assembled view of the alternative embodiment, highlighting a cross sectional area. FIG. 7 depicts the cross section of this embodiment in which conventional "T" slots (504) are formed in the fin (502) inner walls approximately midway between the edge surfaces. The trocar shaft (510) features raised members (506) that correspond with each "T" slot. Although the present embodiment depicts a single slot formed midway between the edge surfaces of each fin, other embodiments may utilize multiple slots per fin, with appropriate spacing between the slots. In such embodiments, the trocar shaft will feature corresponding raised members that engage the slots. Further, although the present embodiment describes use of "T" slots in the fins, other geometric slot shapes that afford positive engagement with corresponding raised members may be utilized. For example, FIG. 8 depicts use of dovetail slots (802) formed in the inner surfaces of the fins (502). Likewise, FIG. 9 depicts use of circular slots (902) formed in the inner surfaces of the fins (502). Still other geometric slot shapes are contemplated and are within the scope of the present invention. Further, it is possible to combine fin edge surface slots with inner surface slots. Such an arrangement may be helpful to more evenly distribute the closing forces applied to the fins during insertion of the trocar device and prevent distortion of the fins.

Figure 10:
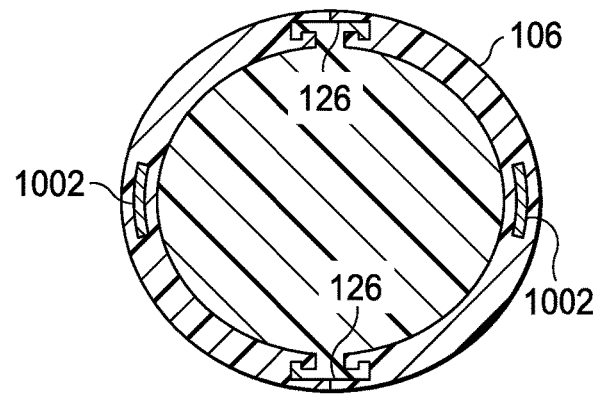
FIG. 10 is a cross section of the working end highlighting an alternative embodiment with an embedded material that assists in the open bias of the fins.
Figure 14:
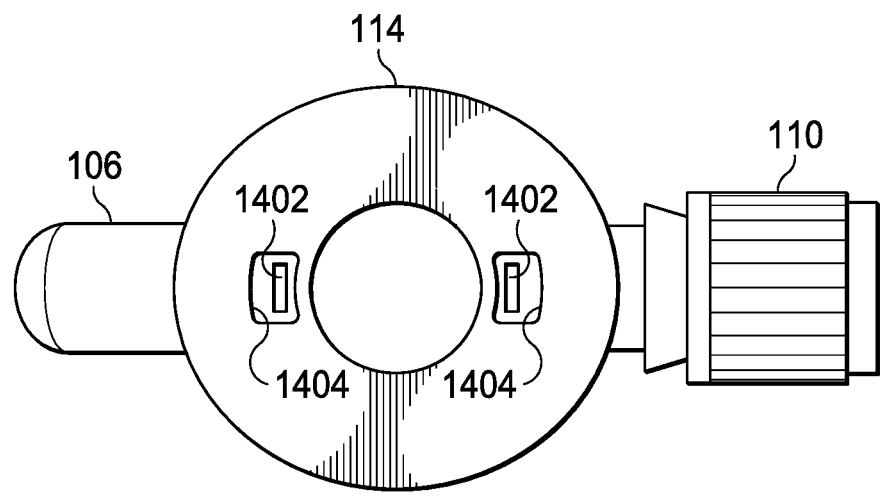
FIG. 14 is a proximal end view depiction of an embodiment of the cannula invention highlighting penetrations into which a biasing device may be inserted.
Figure 15:
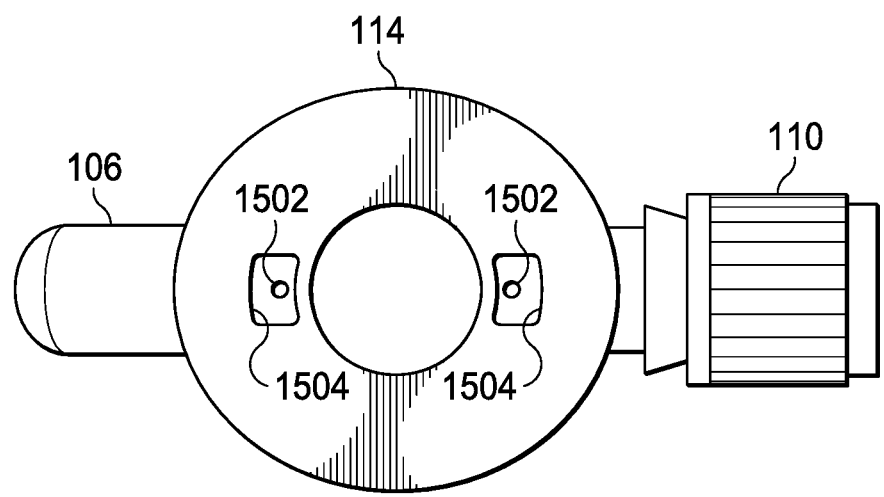
FIG. 15 is a proximal end view depiction of another embodiment of the cannula invention highlighting penetrations into which a biasing device of an alternate shape may be inserted.

In yet another embodiment, it is possible to utilize an embedded shape memory alloy as a biasing device, such as but not limited to Nitinol, in each fin to increase the outward-bias pressure generated by the fins. By increasing the outward bias pressure, it is possible to apply additional compressive stress to the tissue of the patient through which the cannula device is inserted. FIG. 10 depicts such an embodiment. As shown, each fin (106) includes an embedded shape memory alloy strip (1002) within the fin wall at some location between the edge slots (126). This embedded shape memory alloy strip may also be used with the embodiments discussed above, and may be incorporated within the wall beneath or near the respective slot. Further, although the figure depicts use of a single embedded shape memory alloy (1002) in each fin (106), other embodiments may utilize multiple shape memory alloys at various locations spaced within the fin walls. Other biasing devices may include other metals, such as stainless steel, or polymers that exert added biasing force over that provided by the molded fins solely. Moreover, while the shape memory alloys may be permanently included in the fins during manufacture, it is also envisioned that the shape memory alloys may be provided in an insertable/removable form. FIGS. 14 and 15 each present an embodiment of the cannula device incorporating such a feature.

In yet another embodiment it is possible to incorporate an additional alloy with the embedded shape memory alloy to create a bimetallic strip or alter the composition such that it varies, with temperature, the fin outward-bias pressure that is generated. For example, Nitinol may also be "tuned" or "trained" to react at different temperatures by adding additional alloys to its composition. Such a material may be used in the fins of an embodiment to allow the fins to generate greater outward-bias pressures when the fins reach the patient's body temperature.

In other alternate embodiments, integral or removable biasing devices composed of shape memory alloys (such as Nitinol) may be embedded into the fins to generate or supplement outward-bias pressure of varying degrees through electrical activation. For example, a biasing device composed of Nitinol may be embedded into one or more fins of a cannula device and electrically connected to a voltage differential such that the Nitinol forms an electrical circuit. When a current is selectively passed through such circuit, the Nitinol biasing device may be trained to flex outwardly in an amount corresponding to the amount of current passing through such biasing device at least partially forming the aforementioned circuit. A pulse width modulation ("PWM") circuit is preferably utilized to provide for more even heating of the Nitinol biasing device. In this manner, the degree to which the Nitinol biasing device flexes inward and outward may be selectively controlled by the surgical team. Such alternate embodiments configured for electrical activation and in particular, the biasing devices composed of shape memory alloys, should preferably be constructed to include sufficient electrical insulation such that neither the patient nor the surgical team risks being exposed to dangerous electrical current. Electrical components, such as wires, may pass through passages formed in a trocar. Other necessary electrical components needed to provide for electrical activation of such a biasing device (power supply, switch(es), control systems, etc.), may be located remotely from the trocar and cannula or integrated within such structures.

Figure 11:
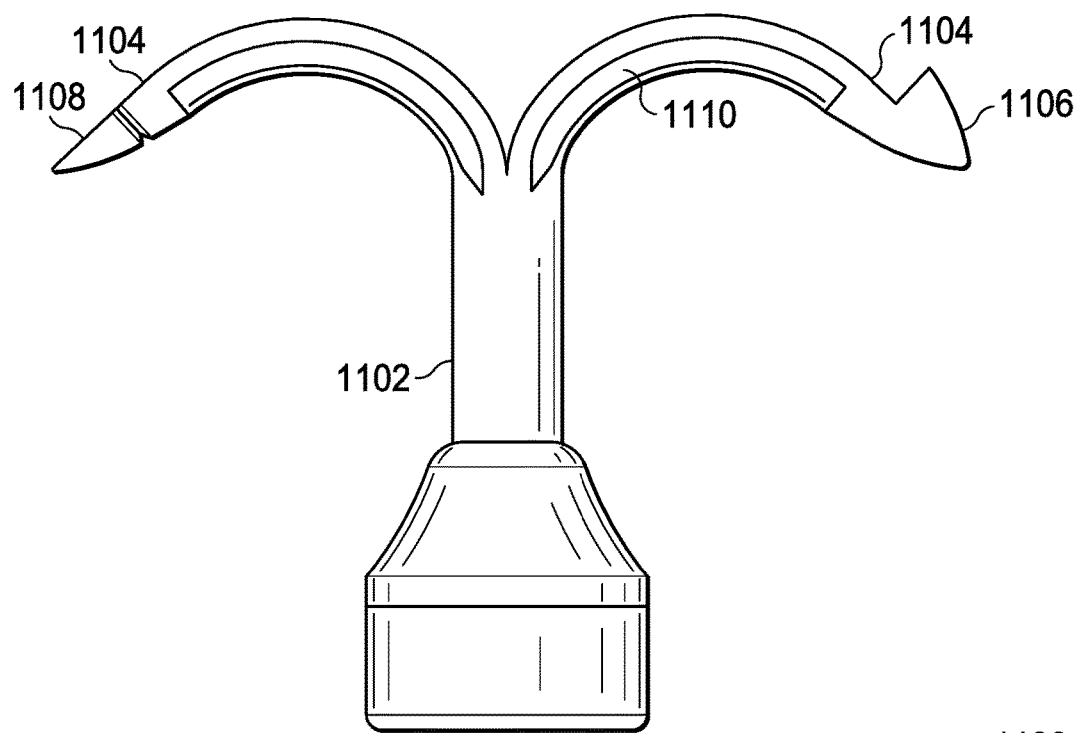
FIG. 11 is an alternative embodiment of the cannula invention with the fins in the open position.

FIG. 11 depicts an alternative embodiment of the cannula device of the present invention. As shown, the cannula device features a body member (1102) with a lumen that exists from the proximal end to the distal end, and a plurality of outwardly-biased fins (1104) extending from the distal end of the body member. Each fin includes a plurality of corrugated features (1110) that extend inward from the outer surface of the fin and are formed along the length of the fin. One fin includes a locking feature (1106) at its distal end for capturing the distal end of the other fins (1108). The locking feature in this embodiment is a conical portion of the distal end of the fin that allows the distal end of the other fins to be captured beneath.

Figure 12:
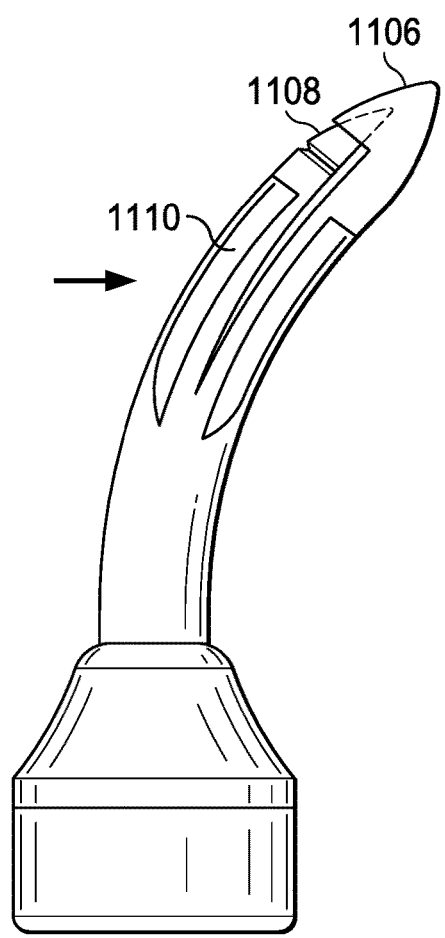
FIG. 12 is a depiction of the process for closing the fins in the alternative embodiment.

This embodiment of the device is prepared as shown in FIG. 12. As depicted, the fins are physically moved inward such that the adjacent fin edges meet and a fin grouping is formed. The fin grouping is then bent toward the fin having the locking feature such that the fin with the locking feature is bent backward as depicted. The relative flexing of the fins in this fashion allows the fins without the locking feature (1108) to be inserted beneath the conical locking feature (1106) such that all are captured in the closed position as further depicted in FIG. 13.

Figure 13:
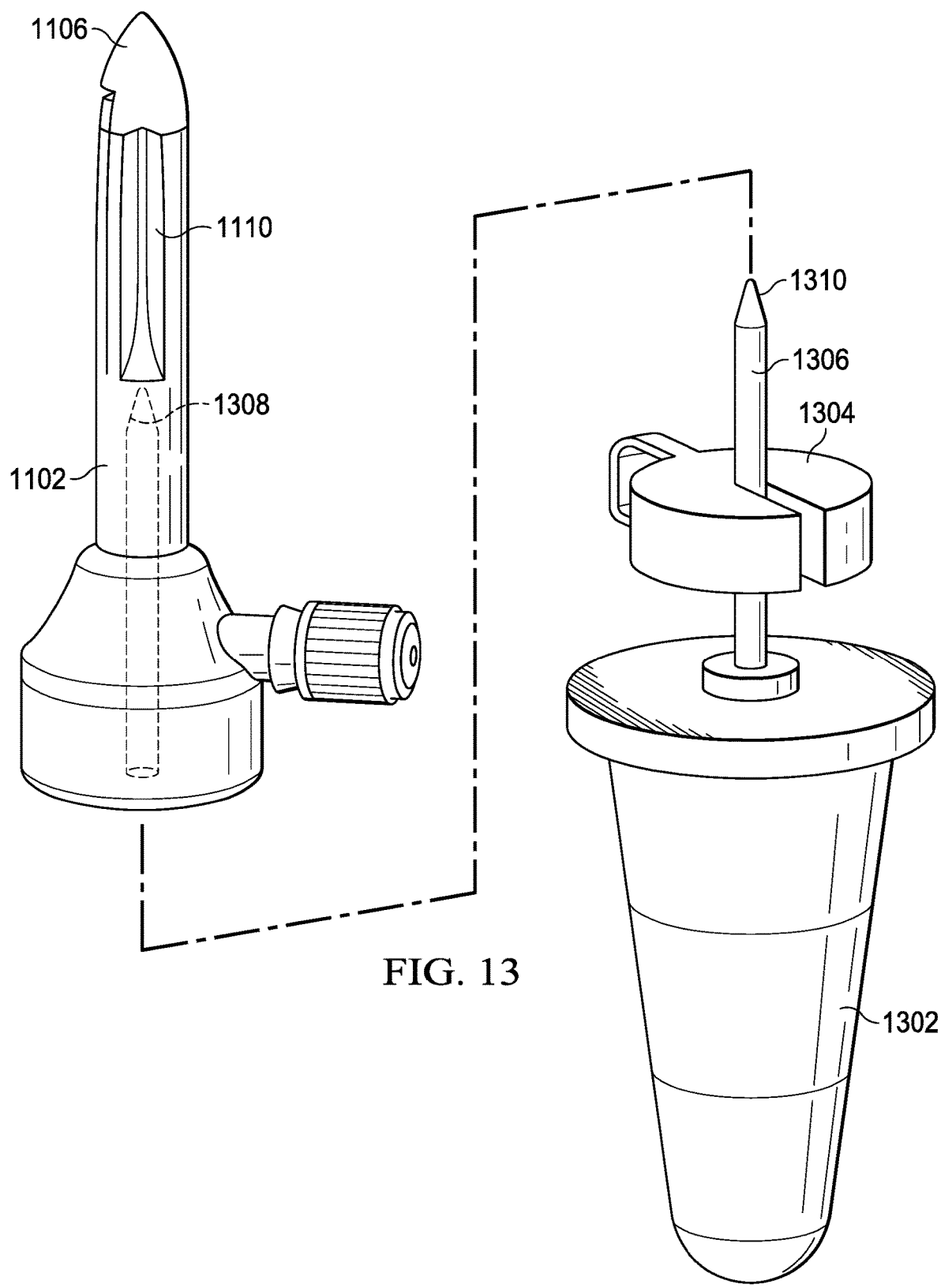
FIG. 13 is a depiction of the alternative embodiment of the cannula invention prior to insertion of the trocar device.

FIG. 13 depicts the additional elements of this embodiment as well as the prepared cannula device. As shown, the embodiment includes a trocar device having a handle (1302) with a shaft member (1306) extending from the proximal end to form a tapered distal end (1308). An anti-plunging device (1304) attaches to the shaft member (1306), and the tapered distal end (1308) is inserted into the proximal end of the cannula device lumen. The anti-plunging device (1304) blocks the shaft member distal end (1308) from advancing past a first position as shown in the figure by hidden lines in the body member (1102). This first position prevents the shaft member distal end (1308) from contacting the corrugated feature (1110) in the fins.

Once assembled, this embodiment may be utilized with a patient by inserting the distal end of the fin into an incision in the patient's skin. Once the body member (1102) is fully inserted, the anti-plunging device (1304) is removed from the shaft (1306) and the trocar is further inserted past the first position to a second position. In the second position, the tapered distal end (1308) contacts the corrugated features (1110), applying force to the fins such that the captured fins are dislodged from beneath the locking feature (1106). The bias pressures of the fins then force the fins to return to the initial outward-bias position, compressing the patient's tissue through which the cannula device was inserted (as in FIG. 19).

FIG. 14 is a proximal end view depiction of an embodiment of the cannula invention highlighting penetrations (also alternatively referred to herein as "cavities") into which a biasing device may be inserted. As shown, the cannula device proximal collar (114) features an additional rectangular biasing device penetration (1402) for accepting an insertable biasing device as depicted in FIG. 16. Each penetration (1402) includes a recessed feature (1404) that reduces the amount that the inserted biasing device protrudes above the surface of the proximal collar (114). The embodiment shown includes a plurality of fins (106), each with penetration that runs from the proximal collar surface to an area beyond the outward bend in the outwardly biased flexible fins (106). In this embodiment in which insertable biasing devices are utilized, it is possible that the biasing forces imparted by the bare flexible fins (106) (no biasing device inserted) can be minimal, which reduces the inward force necessary to converge the fins for insertion of the device into an incision in the skin of a patient.

It is also envisioned that another embodiment may have a plurality of fins with less than all fins having a biasing device penetration. The biasing device penetrations (1402) may be formed by drilling, machining, reaming, or molding the cannula device, or by any other process known in the art that is appropriate for the material utilized for construction of the cannula device. Also, although a rectangular-shaped biasing device penetration is shown, other shapes are envisioned. For example, FIG. 15 is a proximal end view depiction of another embodiment of the cannula invention highlighting penetrations into which a biasing device of an alternate shape may be inserted. The biasing device penetration (1502) in this figure is circular, but one of ordinary skill to which the invention pertains will understand and appreciate that other shapes may be utilized. For example, it is envisioned that the biasing device may utilize a triangular, hexagonal, or octagonal cross section. A recessed feature (1504) is again shown, and is a shape that corresponds to the proximal head of the insertable biasing device. Further, it is also envisioned that multiple penetrations may be formed within a flexible fin (106), thereby allowing a given flexible fin (106) with penetrations to accept one or more insertable biasing devices.

Figure 16A:
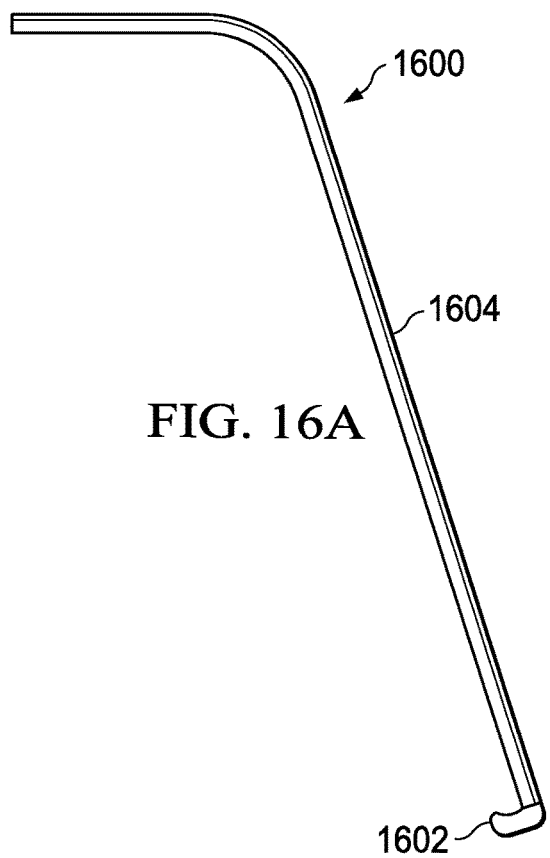
FIG. 16A depicts a side view of a rectangular-shaped embodiment of a biasing device.
Figure 16B:
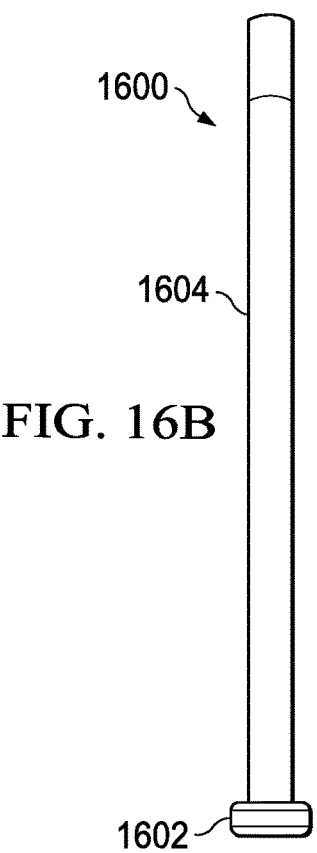
FIG. 16B depicts a front view of the rectangular-shaped embodiment of a biasing device.
Figure 17A:
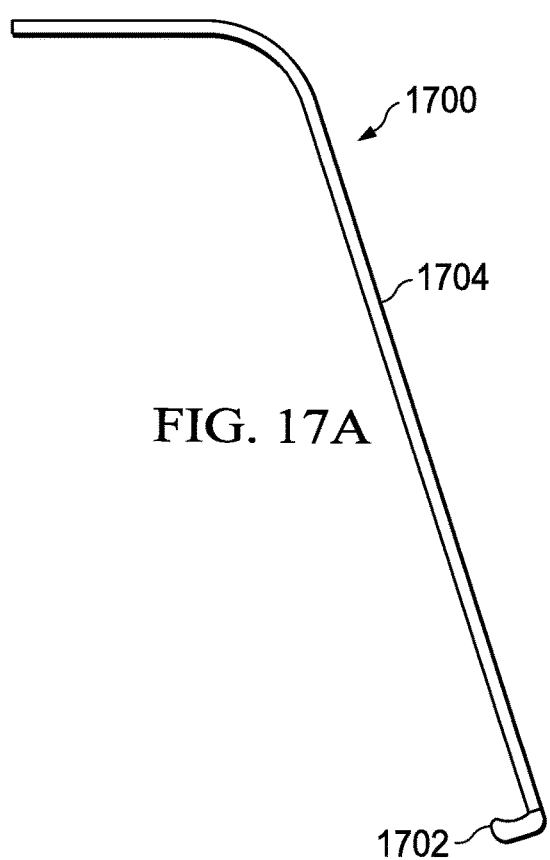
FIG. 17A depicts a side view of a cylindrical-shaped embodiment of a biasing device.
Figure 17B:
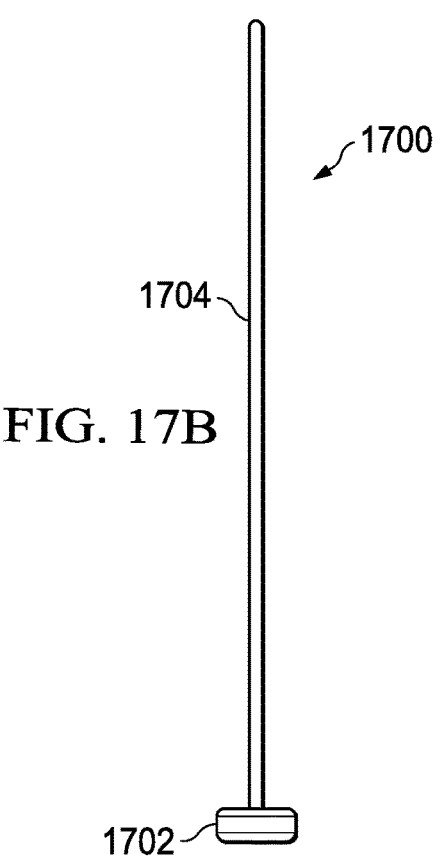
FIG. 17B depicts a front view of the cylindrical-shaped embodiment of a biasing device.

FIGS. 16 and 17 depict two example embodiments of biasing device for the instant invention. FIG. 16A depicts a side view of a rectangular-shaped embodiment of a biasing device, while FIG. 16B depicts a front view of the rectangular-shaped embodiment of the biasing device. Shown is the biasing device (1600) rectangular shaped body (1604) and an attached proximal head (1602). The biasing device features a static bend near the distal end that substantially corresponds to the outwardly biased flexible fin (106) bend into which the biasing device (1600) is to be inserted. The proximal head (1602) provides a feature that allows an operator to apply finger pressure to the device (1600) during insertion and removal. The proximal head (1602) also limits the distance the device (1600) may penetrate into the biasing device penetration (1402/1404). FIG. 17A depicts a side view of a cylindrical-shaped embodiment of a biasing device, while FIG. 17B depicts a front view of the cylindrical-shaped embodiment of the biasing device. The biasing device (1700) cylindrical body (1704) has a circular cross section, with a proximal head (1602) and a static bend near the distal end that substantially corresponds to the outwardly biased flexible fin (106) into which the biasing device (1700) is to be inserted.

Figure 18:
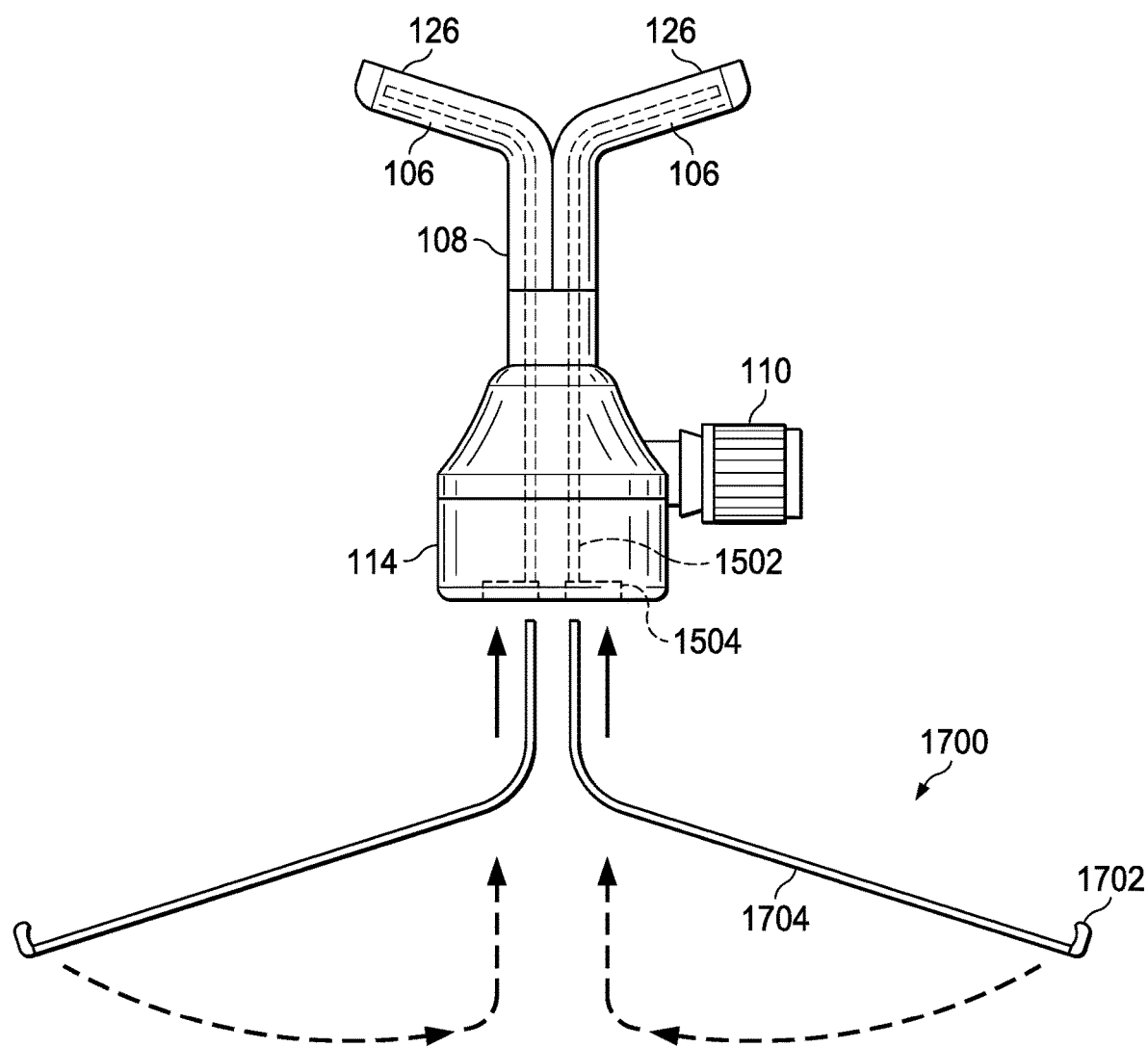
FIG. 18 depicts a side view of an embodiment of the cannula invention highlighting installation of a biasing device.

The cannula device may be prepared by a technician or surgeon prior to use. FIG. 18 is a side view of an embodiment of the cannula invention highlighting installation of the biasing device during device preparation. The cannula device includes biasing device penetrations (1502)—shown in ghosted lines for clarity—extending from the proximal collar (114) surface to substantially the distal tip of the fins (106). The technician or surgeon first converges the fins (106) by finger pressure or trocar and then inserts the distal end of a biasing device (1700) into the penetration (1502) up to the bend and rotates the biasing device body (1704) inward towards the body member (108) lumen while inserting the biasing device (1700) until the proximal head (1702) substantially engages the biasing device recess (1504). Friction between the penetration (1502) wall and the biasing device body (1704) retains the biasing device (1700) or, alternately, a textured body surface may be utilized to cause the biasing device (1700) to be effectively permanently retained within the penetration (1502). Following surgery, the biasing device (1700) may be removed from the disposable cannula and sterilized for reuse in another such cannula. Removal of the alloy biasing device (1700) will also allow for proper recycling/disposal of a polymer cannula. Reuse of the biasing device (1700) will also reduce the overall equipment material costs associated with this cannula device.

The cannula device may also be prepared with additional biasing devices (1700) after the cannula device has been inserted into a patient. In such an instance the surgeon, following insertion of the lumen into an incision in the patient's skin, allows the distal tips of the fins (106) to splay outward as the biasing devices (1700) are inserted as before. Thus, the outward biasing force of the fins (106) may be adjusted inside the patient if necessary. For example, if the retractable cannula fin (106) outward biasing pressure is sufficient without the biasing devices (1700), the biasing devices (1700) may be omitted from the procedure. However, if the patient has an excess of tissue to compress and the fin (106) pressure is inadequate to do so, then one or more biasing devices (1700) may be inserted as above. Further, biasing devices (1700) of differing biasing force (for example, by using different material gauges, cross sectional shapes, compositions, or the like or some combination thereof) may be utilized to allow fine-tuning of the fin (106) compressive force.

Figure 19:
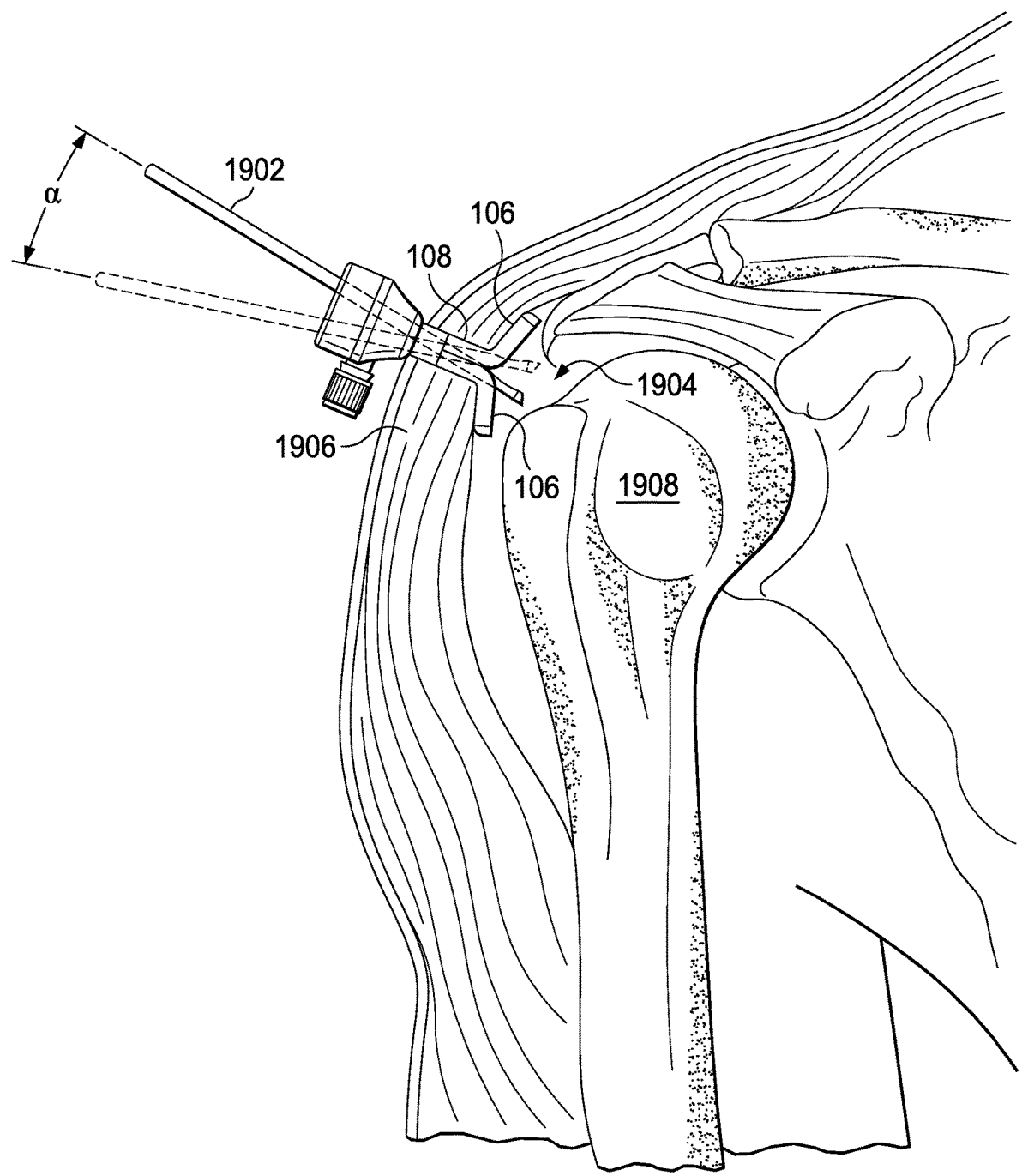
FIG. 19 depicts a cutaway view of an embodiment of the invention in use during shoulder surgery.

Once inside a patient, the trocar is removed from the cannula device and the fins naturally return to their outwardly-biased position. FIG. 19 depicts such an event. As shown, the body member (108) forms a port in the patient's skin and outer tissue (1906) through which surgical instruments (1902) may pass. The outwardly biased flexible fins (106) of the cannula device exert pressure on the tissue (1906) and assist the surgeon in compressing the tissue (1906) to allow for a greater working cavity (1904) and exposure of the surgery site (1908). Because of the compressive effect of the flexible fins (106) on the tissue (1906), the length of the body member (108) may be made relatively short compared to conventional cannula devices. This shortened body member (108) results in a shortened lumen length that, consequently, allows a greater working angle (shown on the figure as the Greek letter "a") for the surgeon's tools (1902), which improves the surgeon's access to the surgery site and reduces the need for physical manipulation of the cannula during surgery. When surgery is complete, the cannula device may be removed by reinserting the trocar device into the lumen such that the trocar raised members engage the slots in the fins and the fins move inward once more. The cannula device may then be withdrawn from the patient with minimal tissue damage. Although the present embodiment is described in use during shoulder arthroscopy, one of ordinary skill will understand that the device may be employed in essentially any arthroscopic, laparoscopic, or other types of endoscopic surgery requiring the surgeon to establish a working port in the tissue of a patient. Moreover, it should be noted that alternate embodiments of the cannula invention may be utilized to perform endoscopic surgery on subjects other than humans such as, for example, animals such as dogs, cats and livestock. Those of ordinary skill in the art will recognize that the dimensions of the cannula invention will require modification depending upon the anatomical structures of the particular subject of the surgery in which the invention is utilized, as wells as the type of endoscopic surgery being performed.

Figure 20:
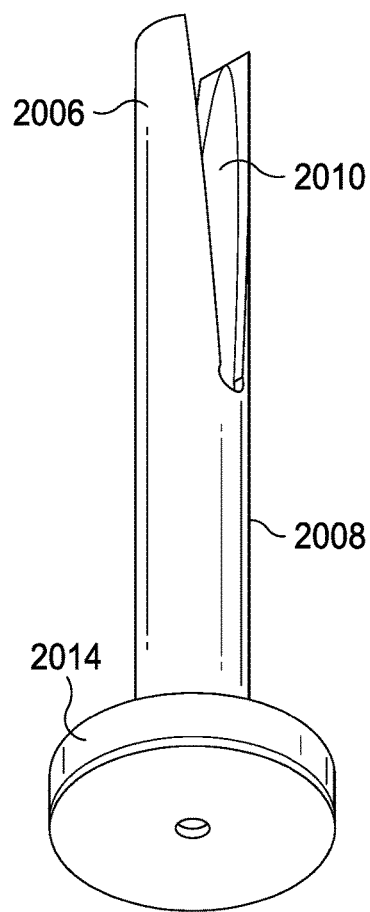
FIG. 20 a perspective view of a further alternate embodiment of a cannula device having cavities formed within to accept insertion of shafts of a biasing device.
Figure 21:
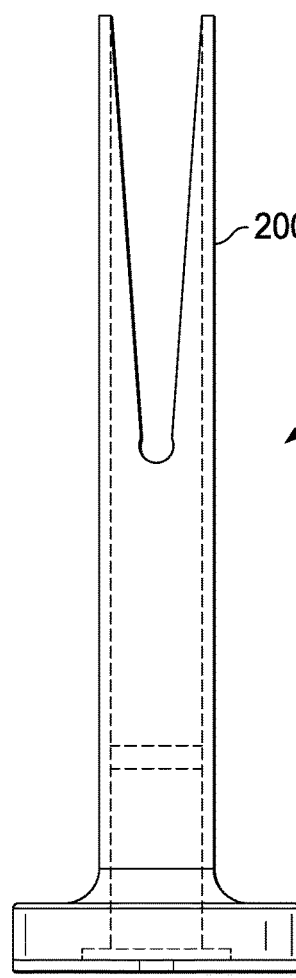
FIG. 21 depicts a side view of the further alternate embodiment of the cannula device as shown in FIG. 20.
Figure 22:
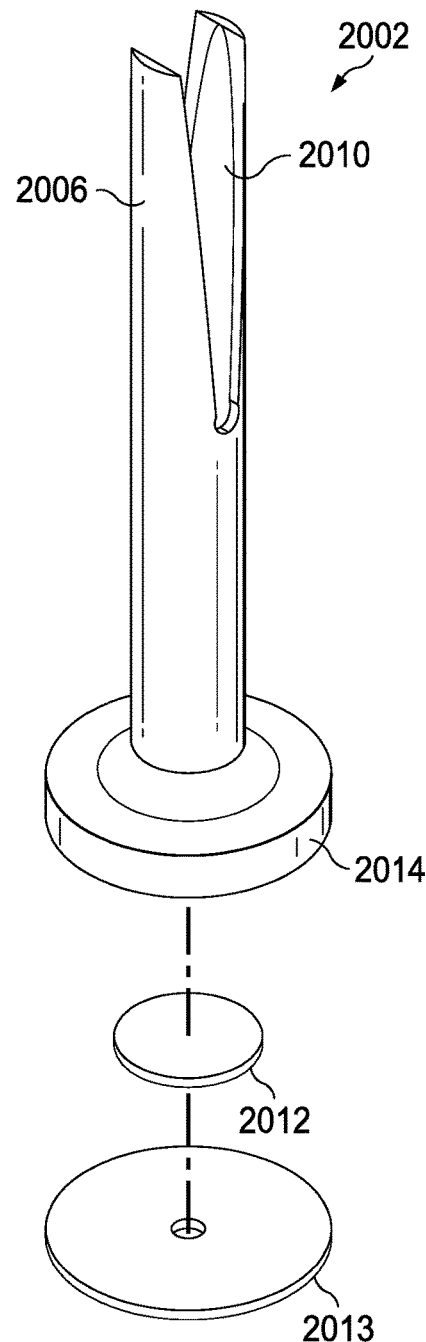
FIG. 22 depicts an exploded view of the alternate embodiment of the cannula device shown in FIG. 20 and FIG. 21.

Referring now to FIG. 20, a perspective view of a further alternate embodiment of a cannula device (2002). The cannula device (2002) comprises a body member (2008), two fins (2006) and a proximal collar (2014). Longitudinal cavities (2010) formed into the fins (2006) provide a passage through which a biasing device (not shown) may be embedded. While the biasing devices of the preferred embodiments described herein are removably insertable into the cannula device, it is contemplated that alternate embodiments may include biasing devices that are integrally embedded into the cannula device. The proximal collar (2014) retains discs used to provide a seal through which surgical instruments may pass. Referring now to FIG. 21, a side view of the further alternate embodiment of the cannula device (2002) as shown in FIG. 20. The cannula (2002) is constructed of medical grade polymer and includes flexible fins (2006) that are neutral with respect to their outward and inward biasing pressure. In even further alternate embodiments, the cannula may be at least partially composed of polymers constructed to provide the fins with an outward biasing pressure at normal temperatures as has been described with respect to the embodiments of the cannula discussed above. Referring now to FIG. 22, an exploded view of the alternate embodiment of the cannula device (2002) shown in FIG. 20 and FIG. 21. A silicone rear gate seal (2012) is attached to the proximal collar (2014) and provides a retaining structure to secure the one or more insertable biasing devices (not shown) within the cannula device (2002) during use. A silicone spacer (2013) is attached to the proximal collar (2014) at a location proximal to the silicone rear gate seal (2012).

Figure 23:
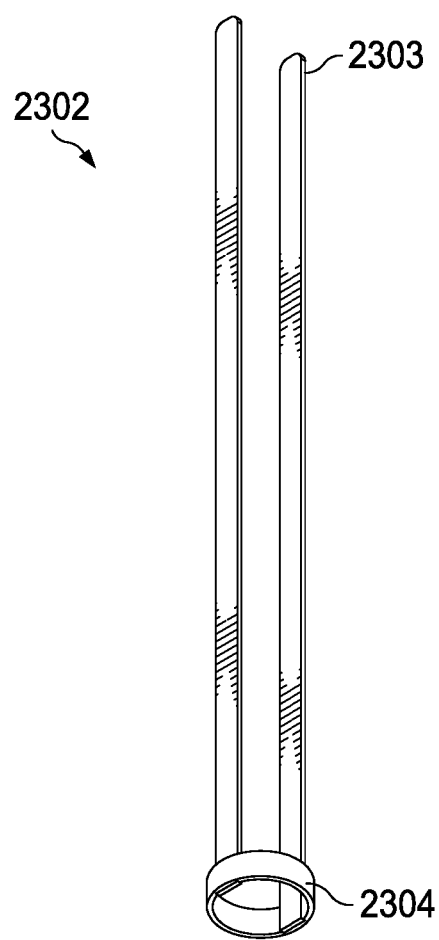
FIG. 23 depicts a perspective view of an alternate embodiment of a biasing device for use insertion into the alternate embodiments of the cannula device shown in FIGS. 20, 21 and 22.

Referring now to FIG. 23, a perspective view of an alternate embodiment of a biasing device (2302) for use in the alternate embodiments of the cannula device shown in FIGS. 20, 21 and 22. The biasing device (2302) is comprised of two elongated shafts (2303) joined at their respective proximal ends by a circular collar (2304). The shafts of the biasing devices shown in FIG. 23 are generally rectangular in the cross-section. However, as has been noted above, alternate embodiments of biasing devices may include shafts having cross sections of various shapes. The biasing device is composed at least partially of a shape memory alloy such as Nitinol, allowing a user to "train" the biasing devices to take on a desired form.

Figure 24:
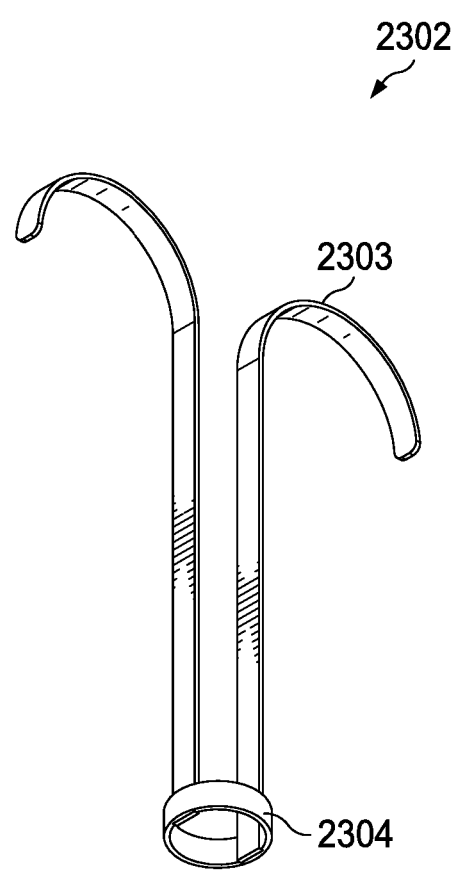
FIG. 24 depicts a perspective view of the alternate embodiment of the biasing device shown in FIG. 23, when such device is in a phase wherein distal portions of the biasing device's shafts are flexed outward.

Referring now to FIG. 24, a perspective view of the alternate embodiment of the biasing device shown in FIG. 23, when such device is in a phase wherein distal portions of the biasing device's shafts are flexed outward. The biasing devices may be composed of materials and "trained" to provide for such outward flexing at desired temperatures. For example, the biasing device may be trained to exhibit such outward flexing upon encountering temperature approximating typical human body temperatures. As previously discussed, biasing devices composed of shape memory alloy(s) may be electrically activated to exhibit such flexing in amounts corresponding to electrical current passed through such biasing devices. While the shafts of the biasing device shown in FIG. 23 and FIG. 24 have shafts with at least portions that are in a substantially parallel configuration with respect to one another, it is contemplated that in alternate embodiments, the biasing devices will include shafts configured to converge towards one another at a predetermined angle, before flexing outwardly. In such embodiments, the convergence of the biasing device shafts may provide, at the convergence point, a fluid retention seal. Such embodiments are discussed below with reference to FIGS. 37-45.

Figure 25:
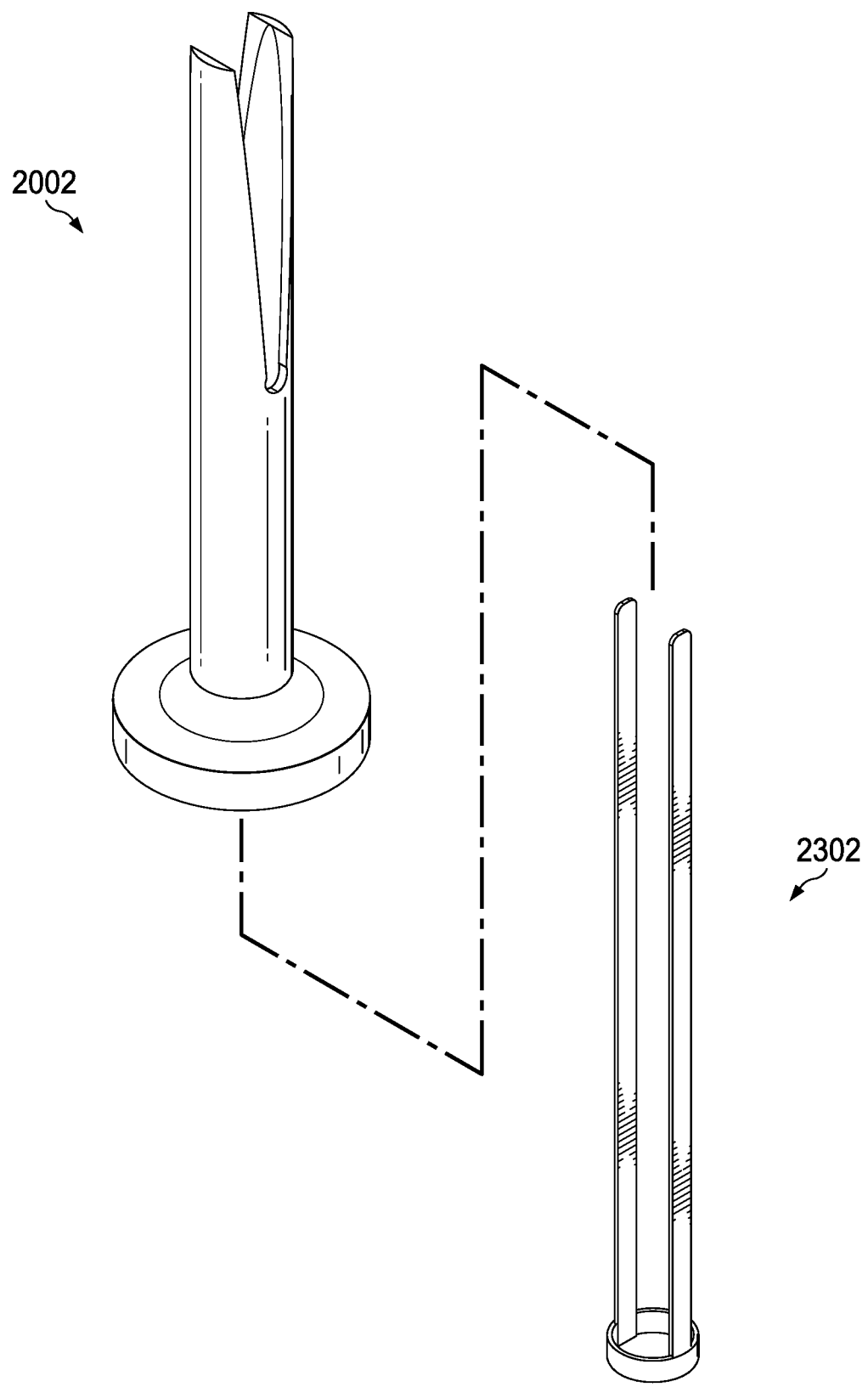
FIG. 25 depicts perspective views of the alternate embodiments of the cannula device and biasing device as shown in FIG. 20 and FIG. 23, respectively.

Referring now to FIG. 25, perspective views of the alternate embodiments of the cannula device (2002) and biasing device (2302) as shown in FIG. 20 and FIG. 23, respectively. Both the cannula device (2002) and biasing device (2302) are configured to mate with one another, allowing a user to insert the biasing device into the cannula device through cavity openings in the cannula device formed into the proximal collar (similar to the penetrations (1504) shown at FIG. 15 and FIG. 18).

Figure 26:
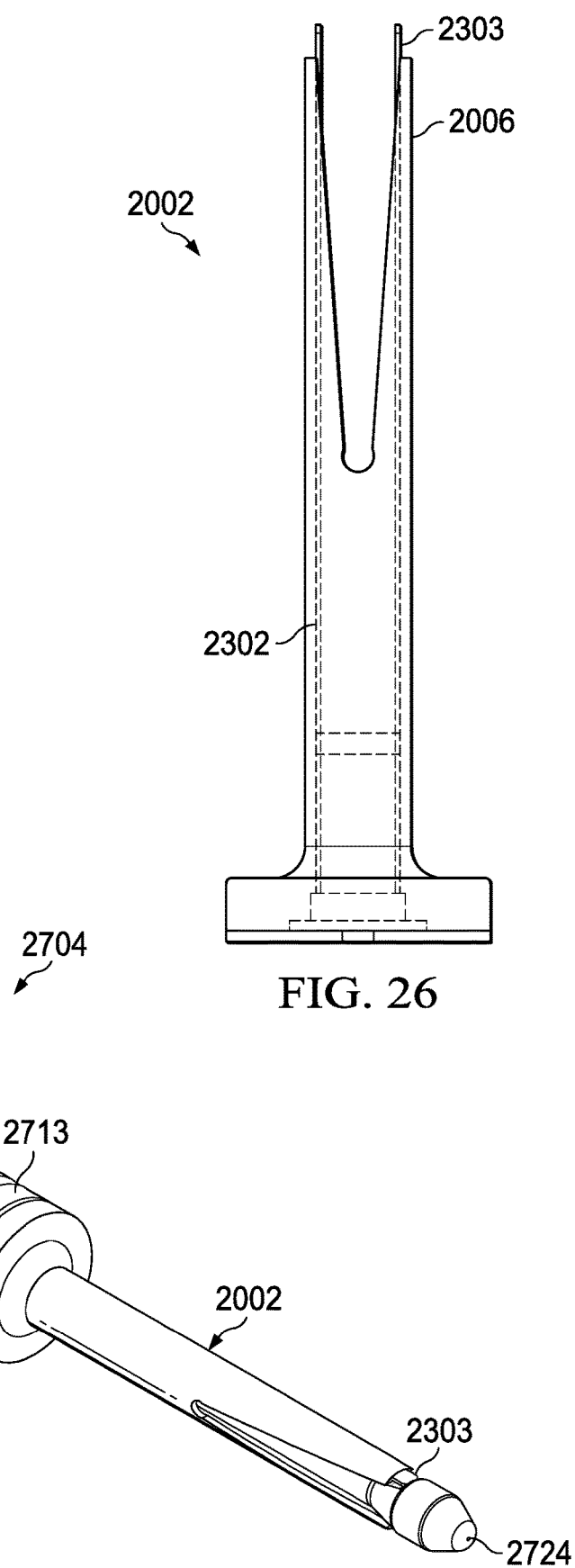
FIG. 26 depicts a side view of the alternate embodiment of the cannula device having an alternate embodiment of a biasing device (shown in broken lines) embedded within cavities formed into the cannula device.

Now referring to FIG. 26, a side view of the alternate embodiment of the cannula device (2002) having an alternate embodiment of a biasing device (2302) (shown in broken lines) embedded within cavities (or "penetrations") formed into the cannula device (2002). The distal ends (2303) of the shafts of the biasing device protrude beyond the distal ends of the cannula device such that when the fins (2006) are released from the trocar device and flex outward, the distal ends (2303) of the biasing device will retreat into the cannula (not protrude as shown in FIG. 26). Further, the protruding nature of the distal ends (2303) of the shafts of the biasing device also provide a structure which may be removably secured to the distal end of a trocar device shaft (via a notch formed onto the distal head of the trocar shaft, said notch shaped to receive and removably secure the distal end of the biasing device shaft), thus keeping the biasing shafts and cannula fins from prematurely flexing outwardly. When activated, through heat, electrical current, or other means, the shafts of the biasing device are configured to flex outwardly, causing the fins (2006) of the cannula to also flex outwardly. Such outward flexing, when the cannula is inserted into the surgical site, assists the surgeon in both compressing the patient's tissue, and further providing a larger working cavity.

Figure 27:
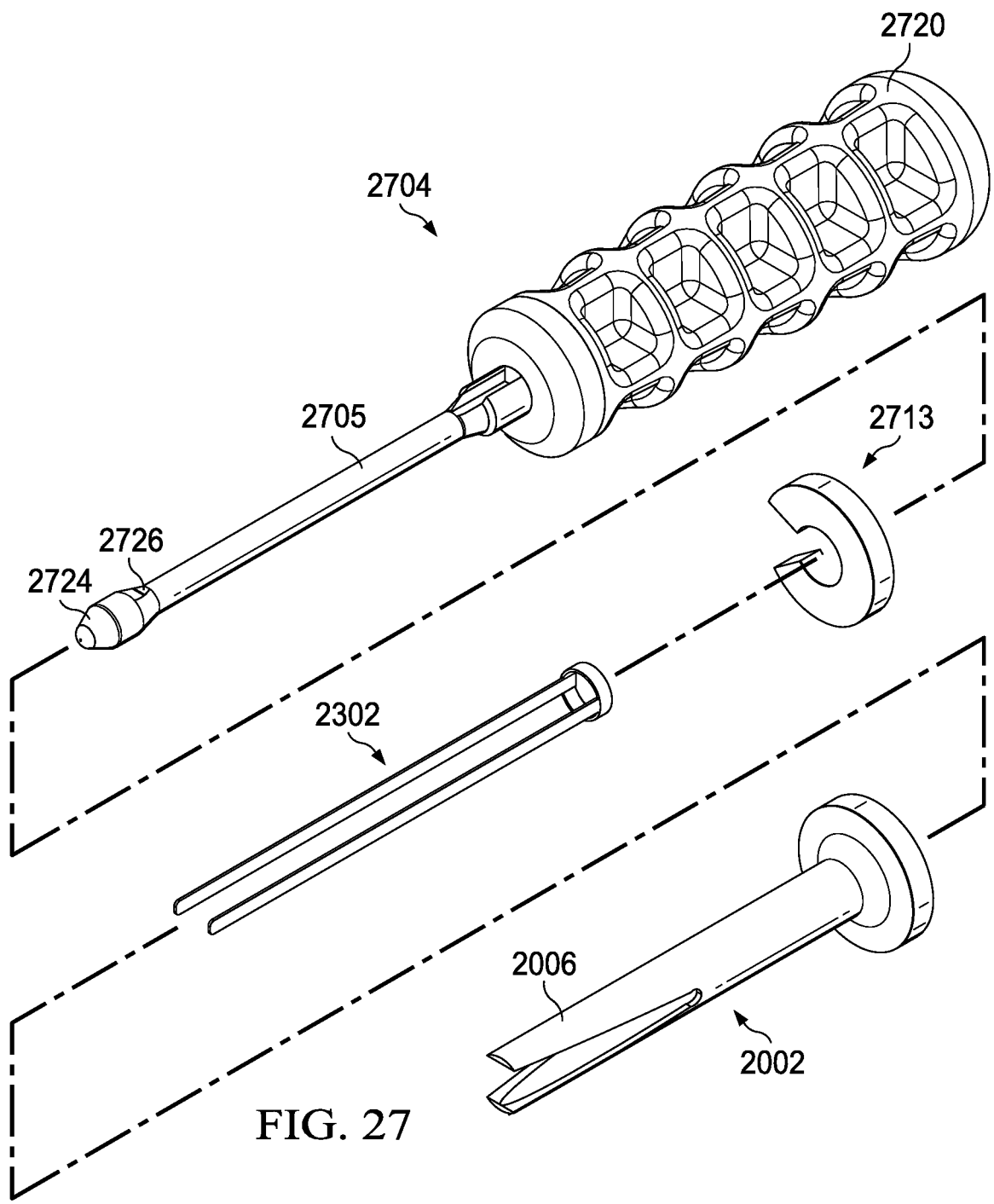
FIG. 27 depicts an exploded view of an alternate embodiment of the cannula device and biasing device as shown in FIG. 26, along with an alternate embodiment of a trocar device for use therewith.

Referring now to FIG. 27, an exploded view of an alternate embodiment of the cannula device (2002) and biasing device (2302) as shown in FIG. 26, along with an alternate embodiment of a trocar device (2704) for use therewith. The trocar device (2704) serves the purpose of both providing a mechanism for physically placing the cannula device (with embedded biasing device) at the surgical site, and also serves to release the biasing device from the inward pressure applied by the shaft (2705) of the trocar device, which is integrally or in some alternate embodiments, removably attached to a distal end of the trocar handle member. Notches (2726) formed on the distal end or "shaft head" (2724) of the trocar device shaft (2705) are shaped to receive and removably secure the distal ends of the shafts of the biasing device (2302). The distal ends of the biasing device shaft may be inserted into the notches (2726) formed on opposite sides of the distal end of the trocar device. It is contemplated that in alternate embodiments of the surgical device deployment tool, other types of receiving member, sized and shaped to receive correspondingly sized and shaped structures of a surgical instrument, may be utilized. For example, in addition to notches, such receiving members may include apertures, latche(s), holes, a hood, and channels. In other alternate embodiments, the receiving members may comprise electromagnets sized to engage and secure biasing members and/or fins having ferrous materials. Embodiments of the trocar device or other surgical device deployment tool may release the fins of the cannula devices and portal holder devices (see below) via a mechanical release mechanism or by an electronic release mechanism. For example, with respect to a mechanical release, a movable spring-loaded release latch located on the distal end of the trocar device may be actuated from a trigger or button located in the trocar device handle (mechanically linked through the trocar shaft) to cause the release of the fins by actuation of the latch. When inserted into the notches, the distal ends of the biasing devices are prevented from flexing outwardly. The trocar device may be constructed of any number of polymers or other materials having rigid or semi-rigid properties. A "c" shaped spacer (2713) is shaped and sized to be removably secured around the proximal end of the trocar device shaft (2705), such that it is located between the distal end of the trocar device handle member (2720) and the proximal collar of the cannula device when the trocar device is attached to said cannula. The spacer (2713) serves to prevent the premature deployment of the biasing device shafts and cannula fins until the time desired by the surgical team. When the spacer (2713) is removed from the space between the distal end of the trocar device handle (2720) and the proximal collar of the cannula, the trocar device may then be moved in a distal direction (generally towards the patient when the cannula has been inserted into a patient), decreasing the gap between said handle and the proximal collar, such that the distal ends of the biasing device shafts are disengaged from the notches (2726), allowing said shafts and the cannula fins to flex outwardly. In this manner, a surgeon may deploy the fins of the cannula at a desired time during a surgical procedure.

Referring now to FIG. 28, a perspective view of the alternate embodiments on the cannula device (2002) and trocar device (2704) shown in FIG. 27. The shaft of the trocar device (2704) is shown inserted into an opening (not shown) in the proximal end of the cannula device such that the distal end (2724) of the trocar shaft protrudes from the distal end of the cannula device. The distal ends (2303) of the biasing device likewise protrude beyond the end of the cannula device. The configuration of the cannula device and trocar device shown in FIG. 28 demonstrate the appearance of such devices prior to insertion into a patient. It should be noted that the distal ends of the biasing device shafts are not shown inserted into the notches (2726) in the drawing shown at FIG. 28. The "c" shaped spacer (2713) is removably secured between the distal end of the trocar device handle and the proximal collar of the cannula. Following completion of the surgery, the biasing device may be returned to its inward phase (through use of thermal or electrical control, or through use of the trocar device) and the trocar device may be used to remove the cannula from the surgical site. The cannula may alternatively be removed without use of a trocar device, utilizing methods discussed above or as known in the art.

Figure 29:
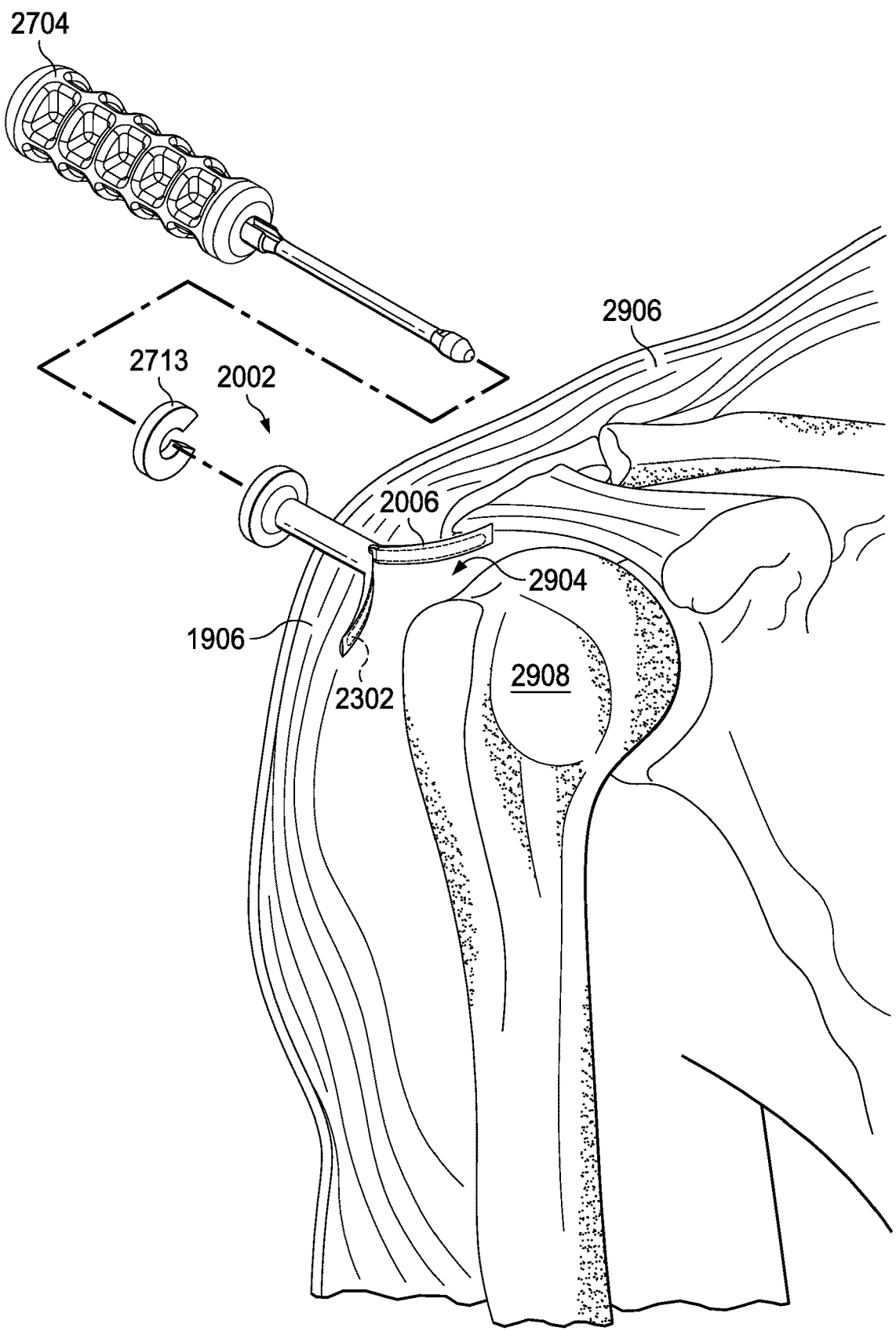
FIG. 29 depicts a cutaway view of the alternate embodiment of the cannula device and trocar device as shown in FIG. 28, in use during shoulder surgery.

Referring now to FIG. 29, showing a cutaway view of the alternate embodiment of the cannula device and trocar device as shown in FIG. 28, in use during shoulder (2906) surgery. The cannula device (2002) has been inserted into the patient's shoulder through use of the trocar device (2704). At the appropriate time, the surgical team may remove the "c" shaped spacer (2713) from the trocar device, allowing the trocar device to be moved distally toward the patient. As the cannula device will remain generally stationary during such movement of the trocar device, the distal ends of the biasing device shafts (2302) will slide out of the notches securing them to the end of the trocar device shaft. Once the distal ends of the biasing device shafts are no longer secured in the notches, said shafts (2302) and the cannula fins (2006) will be free to flex in an outward direction as shown in FIG. 29. The flexible fins (2006) of the cannula device assist the surgical team in compressing the patient's tissue (1906) so that a greater working cavity (2904) is formed, providing better exposure of the surgery site (2908). The outward flexing of the cannula fins also works to put increased pressure on the ports and other cavities inside the cannula. Such increased pressure on the ports and other cavities inside the cannula device aids in creating tighter seals between the cannula device and other surgical instruments passing through the cannula device, leading to less fluid leakage during surgery.

Figure 30:
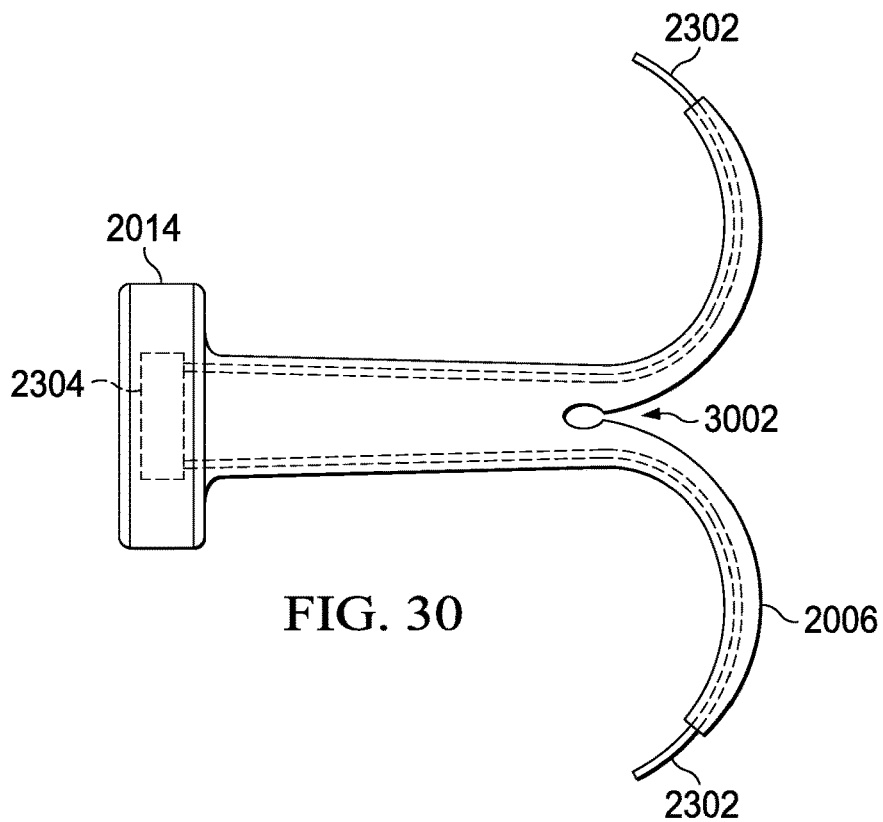
FIG. 30 depicts a side view of an alternate embodiment of the cannula device having a cannula passageway with a flexible distal opening.

Referring now to FIG. 30, showing a side view of a further alternate embodiment of the cannula device with a body member (2002) having a cannula passageway with a flexible distal opening (3002) for aiding in fluid retention during surgical procedures. In the embodiment of the cannula device appearing at FIG. 30, the cannula walls bifurcate approximately halfway between the ends of the cannula. The bifurcated cannula walls serve as flexible fins (2006) that may be outwardly biased with the use of one or more types of biasing devices. In this embodiment, the cannula walls are bifurcated but in other embodiments, the cannula walls could be trifurcated, or split into a plurality of other fins. Also, while the embodiment shown in FIG. 30 illustrates a cannula device bifurcated approximately halfway between the ends of the cannula, the location of the bifurcation (or number of splits) could be located along other points in the length of the cannula, depending on the desired length of fins, which could be based on a number of factors including, but not limited to, the type of surgery, the anatomy of the patient, the type of tissue around the surgical site, and the type of surgical instruments that would need to traverse the cannula opening. In one embodiment, a cannula for surgical procedures comprises a body member having walls forming a lumen along at least a proximal portion of a length of said body member, said walls being bifurcated at two or more points along said length to form a plurality of distally extending flexible fins, wherein said fins are naturally biased in an outward direction, and wherein said walls are flexible such that, following insertion into a patient during a surgical procedure, at least a portion of said walls are compressed inwardly to form a substantially impermeable seal of said lumen.

Outwardly flexing fins (2006) of the cannula device exert a biasing pressure that provides for a more favorable surgical environment. Specifically, as previously described, the outwardly biased flexible fins (2006) of the cannula device exert pressure on the tissue and assist the surgeon in compressing the tissue to allow for a greater working cavity and exposure of the surgery site. In one embodiment, one or more biasing devices are embedded within at least a portion of each of the fins of the cannula device. In one embodiment, the distal tips of the one or more biasing devices protrude from distal ends of each of the flexible fins. In one alternate embodiment, a biasing device (2302) (shown in broken lines) is embedded within cavities formed into the cannula device (2002). The biasing device may be integrally formed within the cannula device so as to be non-removable. Alternatively, the biasing device may be configured to be removable, allowing for the utilization of biasing devices having different material properties or having been "trained" in various manners to perform certain tasks more efficiently for certain procedures, or for certain patient body types and tissue dimensions. As previously discussed, the biasing devices may be composed of any number of materials but are preferably, in this alternate embodiment, composed of a shape memory alloy such as Nitinol. When activated, through heat, electrical current, or other means, the shafts of the biasing device composed of a shape memory alloy, are configured to flex outwardly, causing the fins (2006) of the cannula to also flex outwardly and provide the aforementioned favorable surgical site in that it provides for enhanced visualization of the site for the surgeon.

Still referring to FIG. 30, a flexible opening (3002) is positioned on the cannula device (2002) at approximately the convergence of the cannula fins (2006) with the main cannula body. A substantially tubular aperture which in one embodiment, is approximately 4 millimeters in diameter, and runs longitudinally down a portion of the shaft of the cannula body, having a proximal opening adjacent the proximal collar (2014) or "base" of the cannula, and terminating at the flexible opening (3002). The flexible opening (3002) serves as a substantially impermeable seal for fluid retention during surgical procedures involving the use of irrigation fluid or gases pumped into the surgical site. The flexible opening provides for such a substantially impermeable seal by preferably maintaining a substantially closed state such that the inner walls of the cannula opening are compressed upon one another. Although the term "seal" is used herein, it is contemplated that such seal will allow for the passage of surgical instruments and other tools used in surgery. As used herein, the terms "substantially impermeable" or "substantial fluid retention" do not mean absolute impermeability or sealing effect, but instead means that while some leakage is possible and expected, such leakage does not substantially interfere with the surgical procedure being undertaken with such cannula device. Further, the term "fluid" is not only intended to encompass traditional fluid materials (saline solution, blood, etc.), but also gases and other materials used in surgical procedures or that may otherwise emanate from a patient during surgery. As used herein, the terms "substantially impermeable seal" further contemplates that some acceptable amount of fluid leakage may occur with the traversing of surgical instruments through such seal.

Although the flexible opening (3002), which is located at convergence point of the plurality of fins, preferably naturally maintains a closed configuration, it is also capable of expansion into an open state (as shown in FIG. 30) or semi-open state, allowing for the passage of surgical instruments or other devices used during surgical procedures, while still providing for sufficient fluid retention. In one embodiment, the flexible opening is positioned along the length of the shaft of the cannula body at a location that, when a portion of the cannula is inserted into a patient during a surgical procedure, will be inside the patient near the surgical site itself. This positioning of the flexible opening within the patient at the surgical site, provides fluid retention related advantages not realized in prior art cannula devices. Namely, such a configuration provides for enhanced fluid/gas retention in that the substantially impermeable seal provided by the flexible opening, prevents the leakage of fluids/gases outside of the surgical site itself, and substantially decreases the amount of fluid/gas that can enter into the proximal portions of the cannula body. In one embodiment, the substantially impermeable seal is located distal to the points at which the walls of the cannula bifurcate to form the flexible fins. In alternate embodiments, the substantially impermeable seal is formed proximal to the points at which the walls of the cannula bifurcate to form the flexible fins.

Figure 31:
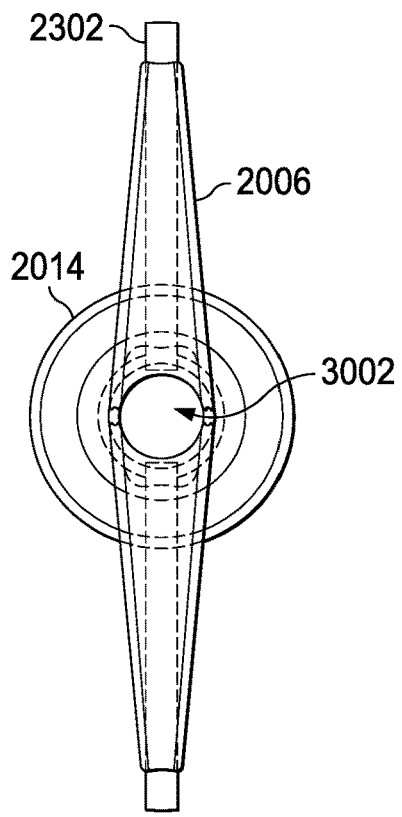
FIG. 31 depicts a top view of the alternate embodiment of the cannula device shown in FIG. 30, showing the flexible distal opening of the cannula passageway in a substantially open position.

Referring now to FIG. 31, depicting a top view of the alternate embodiment of the cannula device (2002) shown in FIG. 30, showing the flexible distal opening of the cannula passageway in a substantially open position. As noted above, although the flexible opening (3002) preferably maintains a naturally closed position, the walls of the opening are flexible in that the material used to construct the opening, which may or may not be in alternate embodiments the same material used to construct the main cannula body, is capable of being opened to varying diameters (although the opening is not necessarily shaped in a circular manner). By providing for this capability, the flexible opening provides for the passage, through the cannula body, of surgical instruments and other devices used in surgical procedures. In contrast to prior art cannula devices, the cannula configuration described herein advantageously provides for the passage of surgical instruments of various sizes, through a relatively small opening that maintains sufficient fluid retention at the surgical site.

Figure 32:
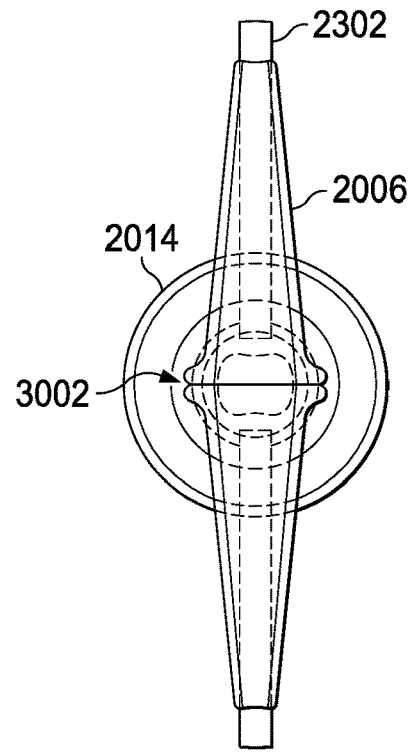
FIG. 32 depicts a top view of the alternate embodiment of the cannula device shown in FIG. 30, showing the flexible distal opening of the cannula passageway in a substantially closed position.

Referring now to FIG. 32, depicting a top view of the alternate embodiment of the cannula device shown in FIG. 30, showing the flexible distal opening (3002) of the cannula passageway in a substantially closed position. In the substantially closed position shown in FIG. 32, the inner walls of the cannula are compressed upon one another at such a force that an adequate seal is created so as to provide for fluid/gas retention during surgery, but not so much force so as to prevent the relatively easy insertion and removal of surgical instruments through the flexible opening. In one embodiment, the cannula body, including the flexible opening, may be constructed of a polymer material that provides for sufficient rigidity and flexibility to be utilized in the manner described herein. In other embodiments, the flexible opening may be composed of a different material than that which is used for other portions of the cannula body, providing for a more flexible material to be used for the flexible opening.

In other alternate embodiments of the cannula device, the flexible opening may be modular in nature and comprise a removable insert for installing and positioning inside the lumen of a cannula device. A flexible opening, configured for removable insertion into a cannula body, would provide further advantages over the prior art in that flexible openings of different dimensions, different shapes, and having different fluid retention properties, could be selected by a surgeon based on a particular surgical application. In one alternate embodiment, the removable flexible opening may be configured having an outer body in a substantially circular shape for insertion in a cannula device having a correspondingly shaped inner shaft, and abutting inner walls providing a seal for substantial fluid retention. In such an alternate embodiment, the removable flexible opening may be configured to be installed via the distal end of the cannula device such that the outwardly flexing fins (2006) may provide space for easy insertion into the main cannula shaft. In one such embodiment, grooves may be formed on the outer walls of the flexible opening, configured to engage corresponding raised members on the inner wall of the cannula lumen intended to engage the modular flexible opening. It is contemplated, with respect to the alternate embodiment discussed in this paragraph and throughout this specification, that structures other than the abutting inner walls described herein, could be utilized to provide for the substantial fluid retention sought during surgical procedures.

Figure 33:
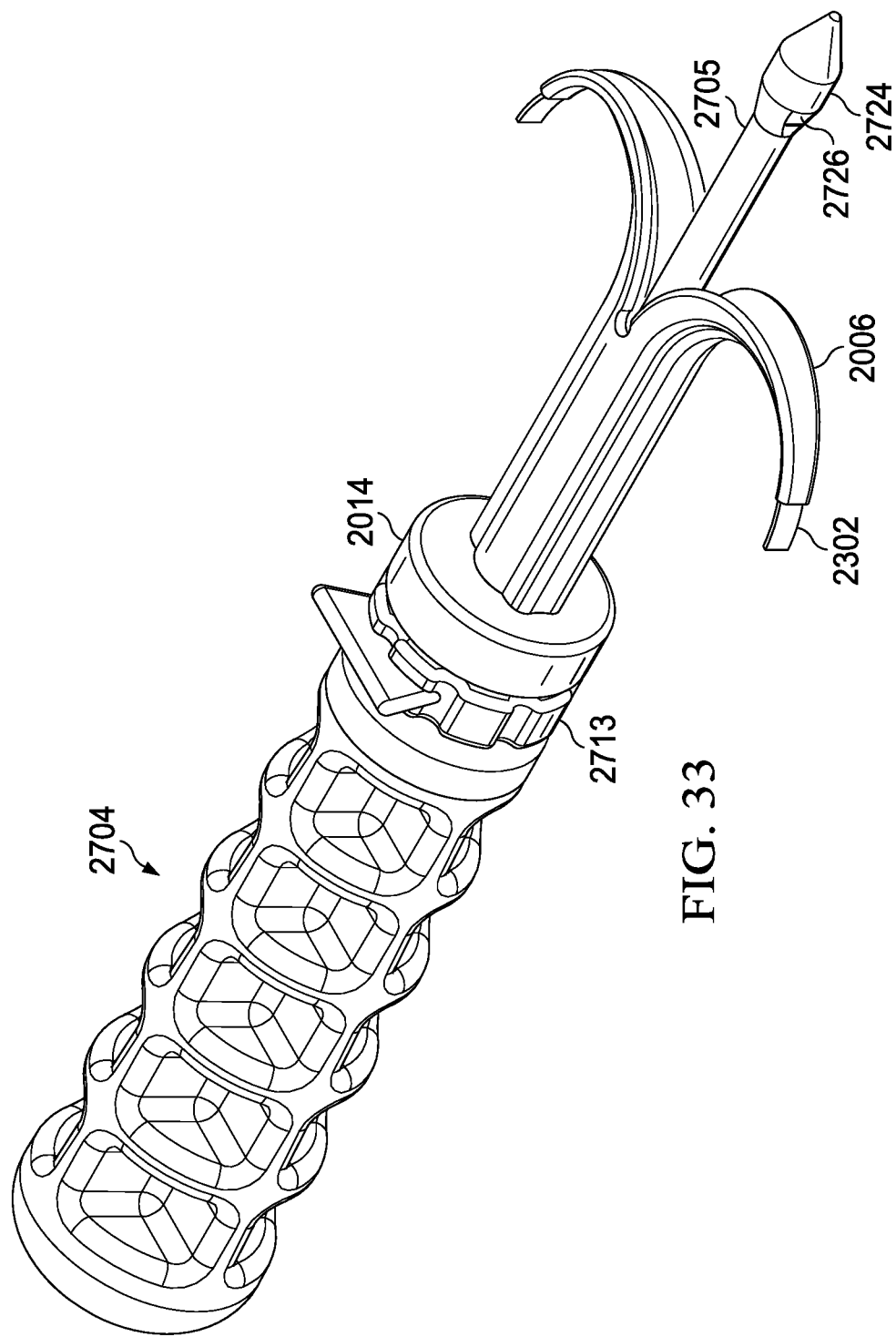
FIG. 33 depicts a perspective view of the alternate embodiments of the cannula device of FIG. 30 mounted to a trocar device.

Referring now to FIG. 33, depicting a perspective view of the alternate embodiments of the cannula device (2002) of FIG. 30 mounted to a trocar device (2704). The shaft of the trocar device is shown inserted into an opening (not shown) in the proximal end of the cannula device (2002) such that the distal end (2724) of the trocar shaft protrudes from the distal end of the cannula device. The distal ends of the biasing device protrude beyond the end of the cannula device. The configuration of the cannula device and trocar device shown in FIG. 33 demonstrate the appearance of such devices prior to insertion into a patient. It should be noted that the distal ends of the biasing device shafts are not shown inserted into the notches (2726) in the drawing shown at FIG. 33. A "c" shaped cannula removal tool (2713) is removably secured between the distal end of the trocar device handle and the proximal collar (2014) of the cannula.

Figure 34:
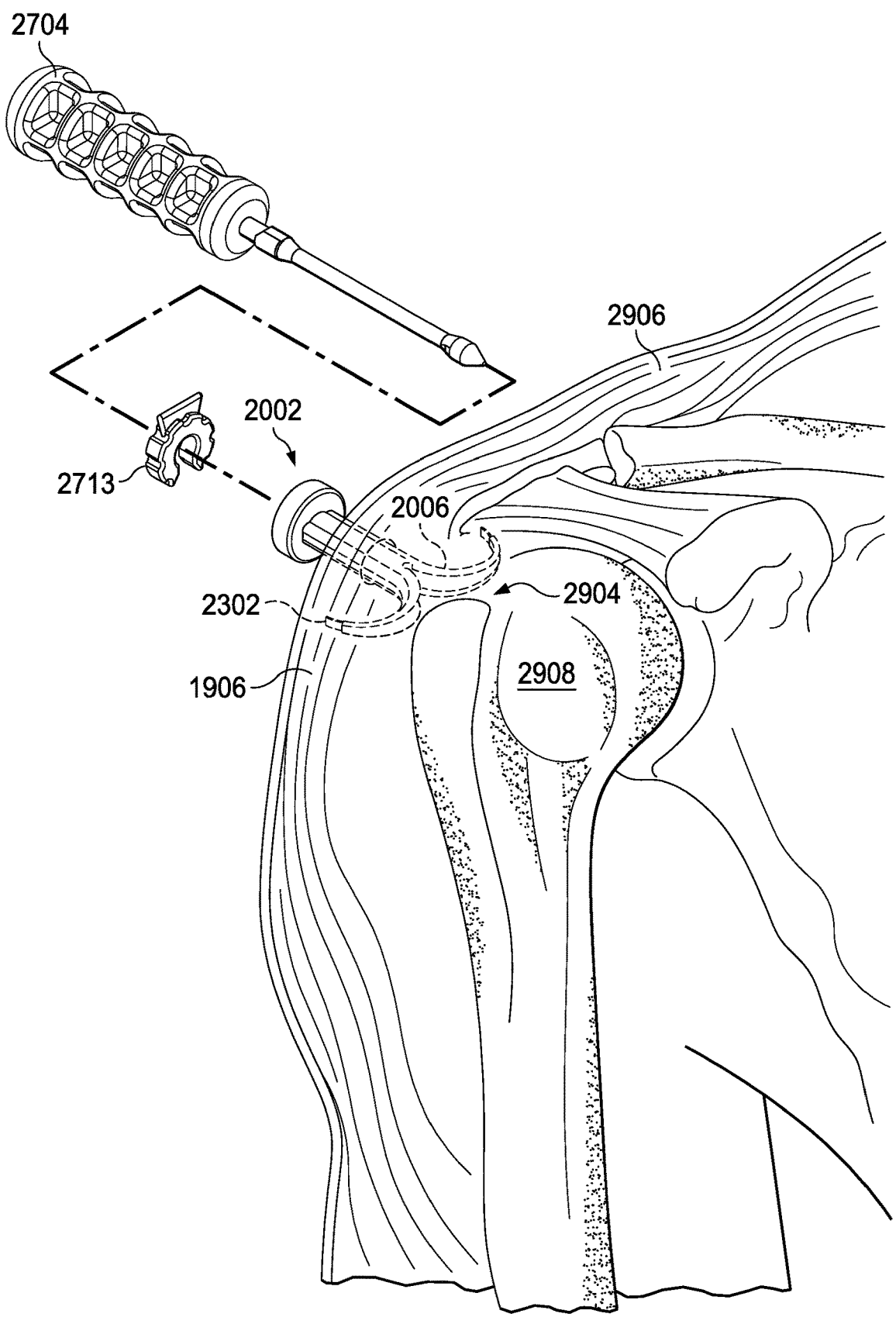
FIG. 34 depicts a cutaway view of the alternate embodiment of the cannula device and trocar device as shown in FIG. 33, in use during shoulder surgery.

Referring now to FIG. 34, depicting a cutaway view of the alternate embodiment of the cannula device and trocar device as shown in FIG. 33, in use during shoulder surgery. The cannula device (2002) has been inserted into the patient's shoulder through use of the trocar device (2704). At the appropriate time, the surgical team may remove the "c" shaped spacer and cannula removal tool (2713) from the trocar device, allowing the trocar device to be moved distally toward the patient. As the cannula device will remain generally stationary during such movement of the trocar device, the distal ends of the biasing device shafts (2302) will slide out of the notches securing them to the end of the trocar device shaft. Once the distal ends of the biasing device shafts are no longer secured in the notches, said shafts (2302) and the cannula fins (2006) will be free to flex in an outward direction as shown in FIG. 34. The flexible fins (2006) of the cannula device assist the surgical team in compressing the patient's tissue (1906) so that a greater working cavity (2904) is formed, providing better exposure of the surgery site (2908). The flexible opening (not shown), positioned during surgery within the patient and directly adjacent to the surgical site, provides for enhanced fluid/gas retention during the surgical procedure.

Figure 35:
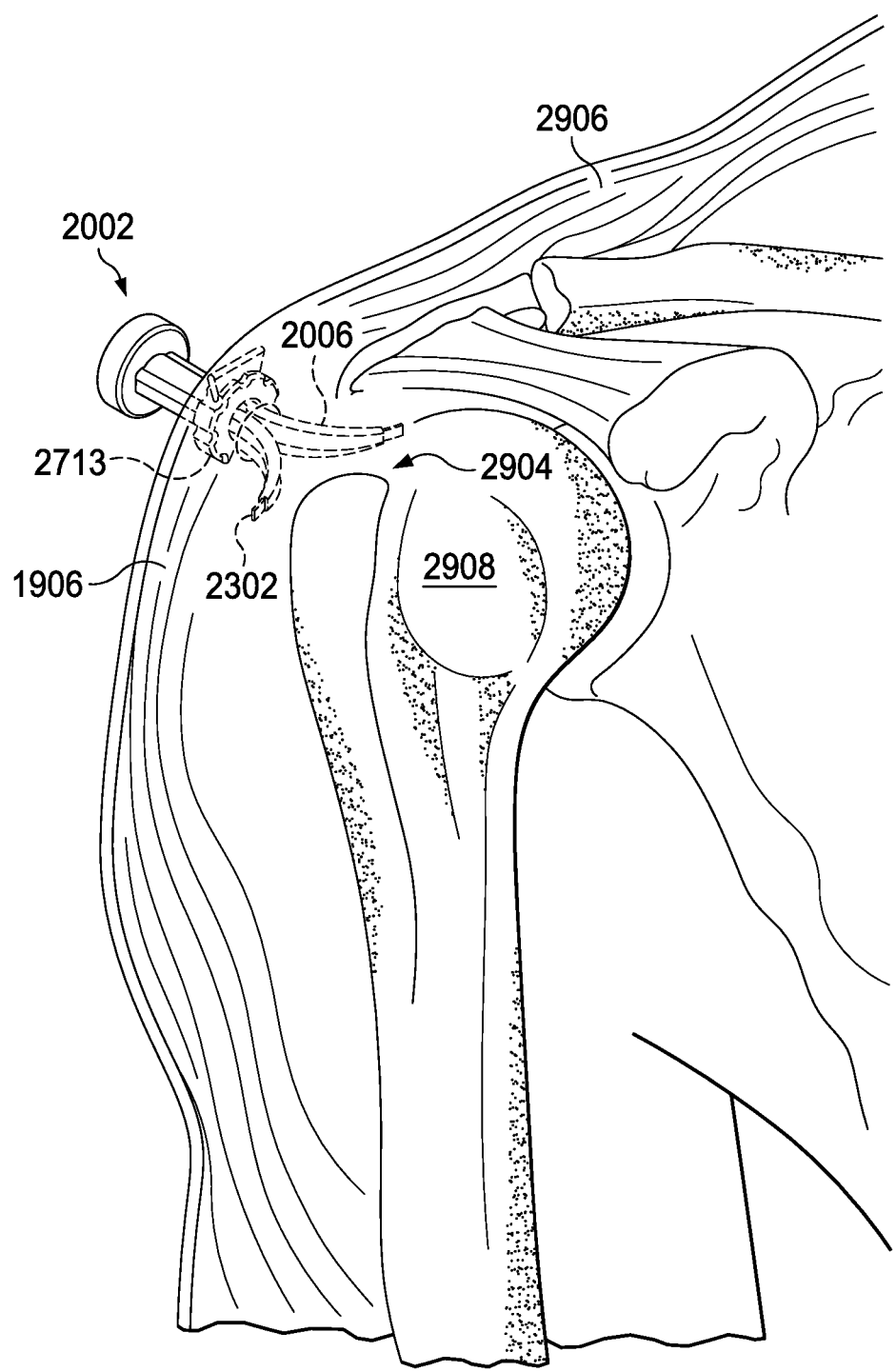
FIG. 35 depicts a cutaway view of the alternate embodiment of the cannula device as shown in FIG. 34, having a cannula removal tool mounted around the shaft of the cannula to aid in removal of the cannula from a patient following shoulder surgery.

Referring now to FIG. 35, depicting a cutaway view of the alternate embodiment of the cannula device (2002) as shown in FIG. 34, having a "c" shaped cannula removal tool (2713) mounted around the shaft of the cannula to aid in removal of the cannula from a patient following shoulder surgery. At the termination of surgery, or at any time it is desirable to remove the cannula device, the cannula removal tool may be mounted on the outer body of the cannula device and used to apply inward pressure on the biasing fins (2006) to aid in removal from the patient. In one embodiment, the cannula removal tool (2713) is configured in a "c" shape to engage the proximal end of the shaft of the trocar device and, as previously described herein, to be employed during the deployment of the cannula device from the trocar so as to release the outwardly biased fins. In one embodiment, the cannula removal tool (2713) includes an integrally attached handle for aiding in the removal of the tool from the trocar device, and also to aid in the removal of the cannula device from the patient.

Figure 36:
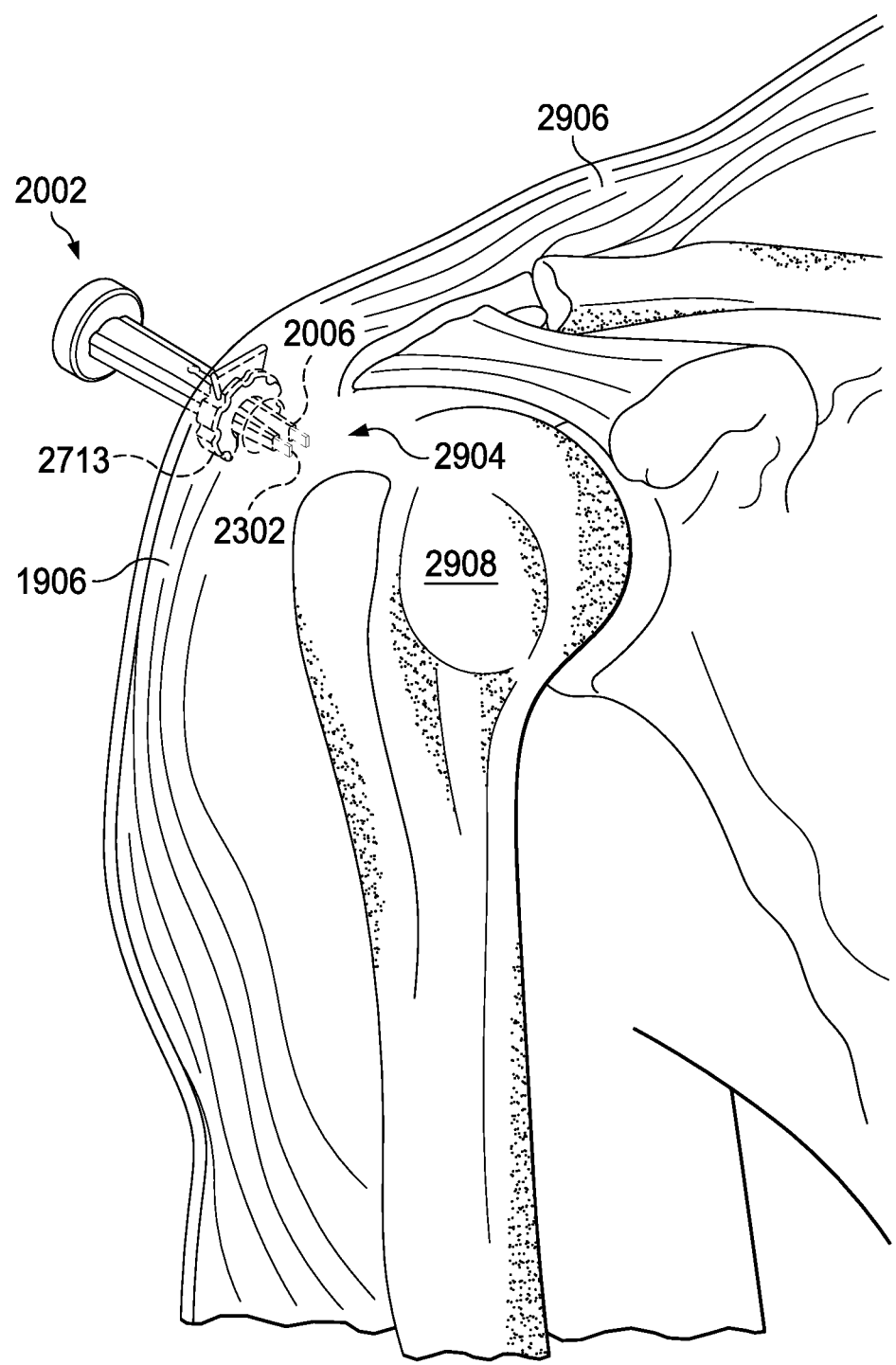
FIG. 36 depicts a cutaway view of the alternate embodiment of the cannula device being used in shoulder surgery as shown in FIG. 34, in which the cannula removal tool mounted around the shaft of the cannula aids in straightening the biasing device fins during removal of the cannula from the patient.

Referring now to FIG. 36, depicting a cutaway view of the alternate embodiment of the cannula device (2006) being used in shoulder surgery as shown in FIG. 34, in which the cannula removal tool (2713) is mounted around the shaft of the cannula as it aids in straightening the cannula fins (2006) during removal of the cannula from the patient. In one embodiment, the cannula device (2006) may be removed from the patient, utilizing the cannula removal tool (2713), by mounting the tool on the outer cannula body, grasping and gently pulling the cannula away from the patient, while at the same time sliding the tool in a distal direction down the cannula body towards the patient. The tool thus depresses against the patient's skin as the cannula is slowly removed, and at the same time causes the fins (2006) to be inwardly biased, which further eases the removal of the cannula device. It is contemplated that in other alternate embodiments, the cannula removal tool may be shaped and sized in various alternate forms that will further enhance the ability of the tool to assist in removal of the cannula.

Figure 37:
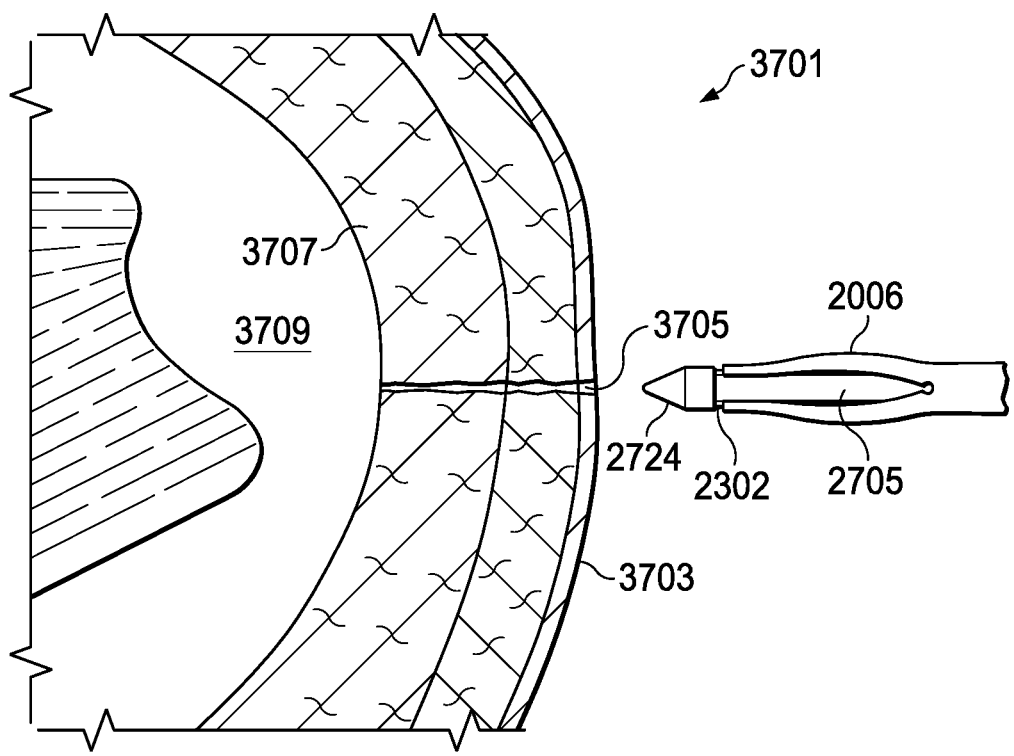
FIG. 37 depicts a side view of the alternate embodiment of the cannula device and trocar device as shown in FIG. 33, in use during shoulder surgery, and more specifically, at a time just prior to insertion into a shoulder tissue structure.

Referring now to FIGS. 37-46, shown are side views of the alternate embodiment of the cannula device and trocar device as shown in FIG. 33, in use during shoulder surgery. In particular, FIG. 37 depicts a partial side view of the alternate embodiment of the cannula device and trocar device as shown in FIG. 33, in use during shoulder surgery, and more specifically, at a time just prior to insertion into a shoulder tissue structure. In FIG. 37, the fins (2006) of the cannula (bifurcated cannula walls) and embedded biasing devices (2302) are mounted on a trocar, although here only the trocar shaft (2705) and distal head (2724) are shown. In its non-deployed state, the distal tips of the biasing device are secured within notches in the head (2724) that are sized to receive them until the time of deployment. Still referring to FIG. 37, a cross-sectional view of a patient (3701) is shown adjacent to the distal end of the cannula device and trocar. Various layers of patient tissue (3707) is shown adjacent to a surgical site (3709). An incision point (3705) in the patient is shown, which forms one end of a passageway the cannula/trocar device must pass to access the surgical site.

Figure 38:
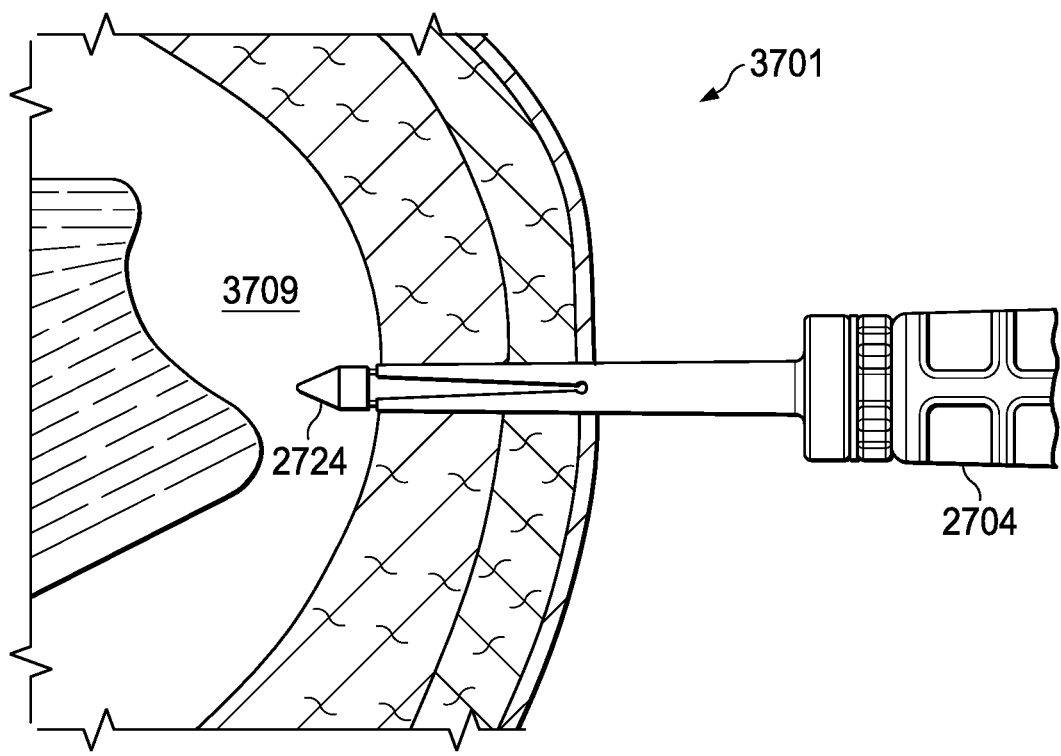
FIG. 38 depicts a side view of the alternate embodiment of the cannula device and trocar device as shown in FIG. 37, in use during shoulder surgery, and more specifically, at a time just following insertion of the cannula device and trocar device shaft into a shoulder tissue structure.
Figure 39:
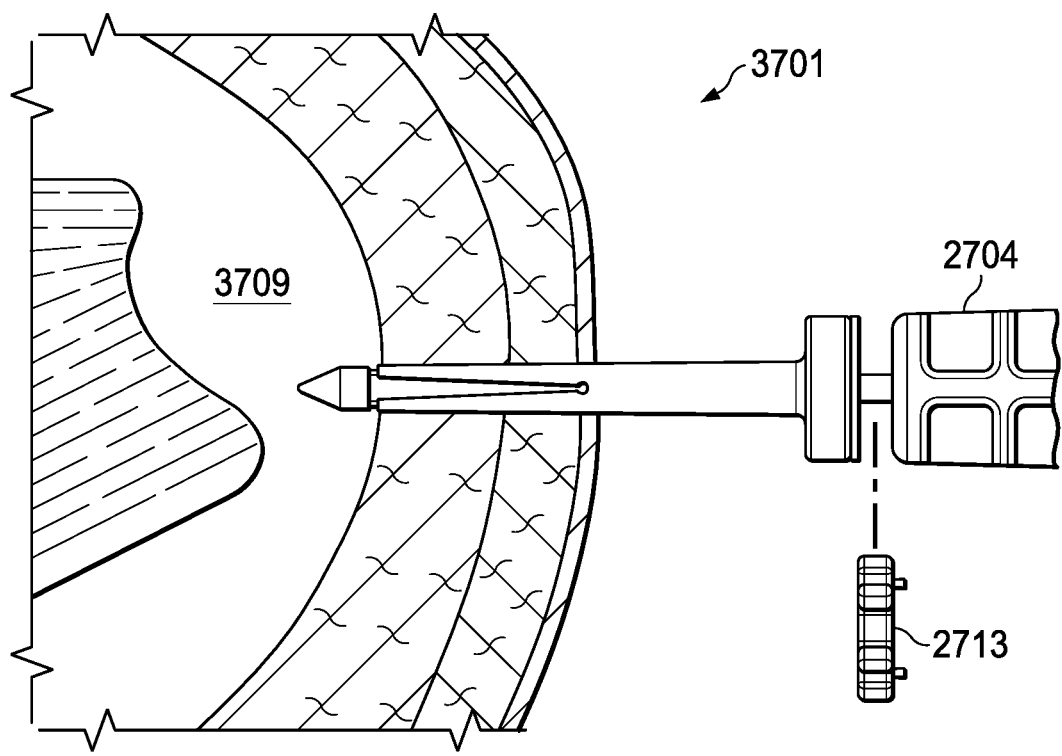
FIG. 39 depicts a side view of the alternate embodiment of the cannula device and trocar device as shown in FIG. 37, in use during shoulder surgery, and more specifically, at a time just following insertion of the cannula device and trocar device shaft into a shoulder tissue structure, the cannula removal tool being removed to allow for deployment of the cannula biasing fins.

FIG. 38 depicts a side view of the alternate embodiment of the cannula device and trocar device (partial view) as shown in FIG. 37, in use during shoulder surgery, and more specifically, at a time just following insertion of the cannula device and trocar device shaft into a shoulder tissue structure. The cannula device remains in its non-deployed state during such insertion. FIG. 39 depicts a side view of the alternate embodiment of the cannula device and trocar device (partial view) as shown in FIG. 37, in use during shoulder surgery, and more specifically, at a time just following insertion of the cannula device and trocar device shaft into a shoulder tissue structure, the cannula removal tool being removed to allow for deployment of the cannula biasing fins. The removal of the c-shaped tool (2713) from the trocar shaft (2705) leaves a space between the proximal end of the cannula device and the distal end of the trocar handle. This space provides for rearward movement (away from the patient) of the cannula device along the trocar shaft (2705), while the head of the trocar (2724) remains substantially unmoved, allowing for the deployment of the fins. As the cannula moves rearward during the deployment process, so do the distal tips of the biasing devices, allowing them to free themselves from the notches to which they were secured in the non-deployed state. Once the distal tips of the biasing devices are no longer secured within the notches on the head of the trocar device, the fins naturally flex outward away from the trocar shaft.

Figure 40:
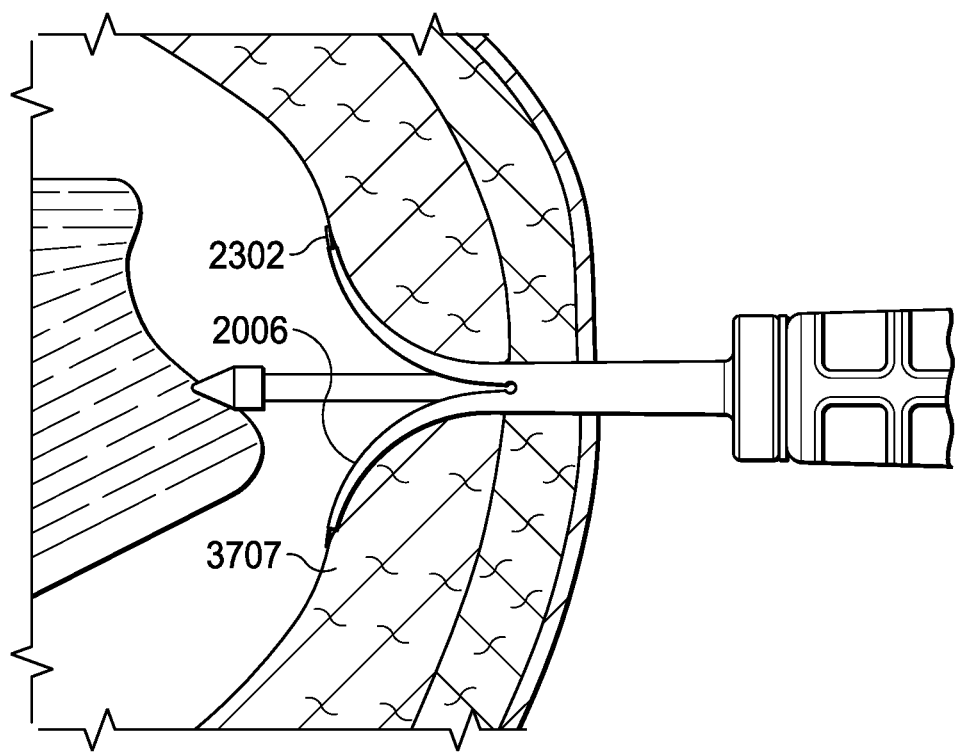
FIG. 40 depicts a side view of the alternate embodiment of the cannula device and trocar device as shown in FIG. 37, in use during shoulder surgery, and more specifically, at a time just following deployment of the cannula biasing fins.
Figure 41:
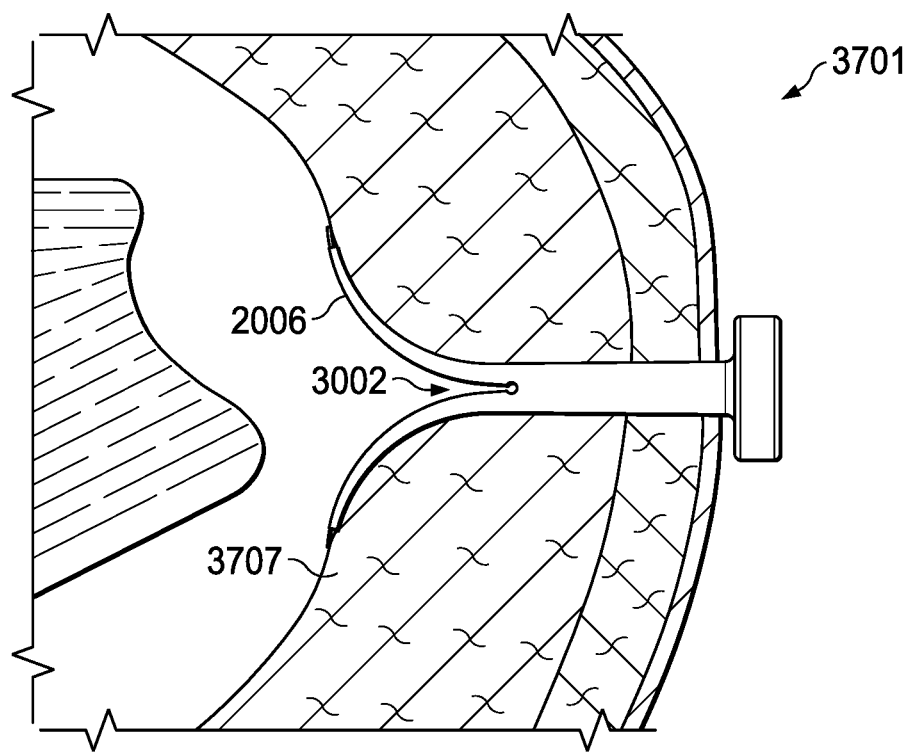
FIG. 41 depicts a side view of the alternate embodiment of the cannula device and trocar device as shown in FIG. 37, in use during shoulder surgery on a patient having a higher than average body mass index, and more specifically, at a time just following deployment of the cannula biasing fins.

FIG. 40 depicts a side view of the alternate embodiment of the cannula device and trocar device as shown in FIG. 37, in use during shoulder surgery, and more specifically, at a time just following deployment of the cannula biasing fins. Once deployed, the fins of the cannula device work to compress the patient's tissue, allowing for a shorter lumen length of the cannula. FIG. 41 depicts a side view of the alternate embodiment of the cannula device and trocar device as shown in FIG. 37, in use during shoulder surgery on a patient having a higher than average body mass index, and more specifically, at a time just following deployment of the cannula biasing fins. The flexible fins (2006) act to compress the additional tissue of the patient, resulting in a shortened lumen length. As discussed elsewhere herein, this is an advantage not seen in surgical cannulas of the prior art because this shortened lumen length allows a greater working angle for the surgeon's tools, which in turn provides for better access to the surgery site, and reduces the need for physical manipulation of the cannula during surgery. Because the non-bifurcated portion of the cannula is shorter, hence a shorter lumen length, the advantage discussed above is most substantial when performing surgery on patients having a greater amount of fat tissue, as the flexible fins work to compress such tissues that would otherwise lead to a lessened range of movements during surgery (because a greater lumen length would be required). The patient's tissue also acts to compress the flexible opening (3002) of the cannula, which allows the inner walls of the cannula to act as a barrier to fluid movement, providing a substantially impermeable seal for fluid retention during surgery. This ability of the flexible opening to serve as a substantially impermeable seal during surgery provides an additional advantage not provided by prior art cannulas.

Figure 42:
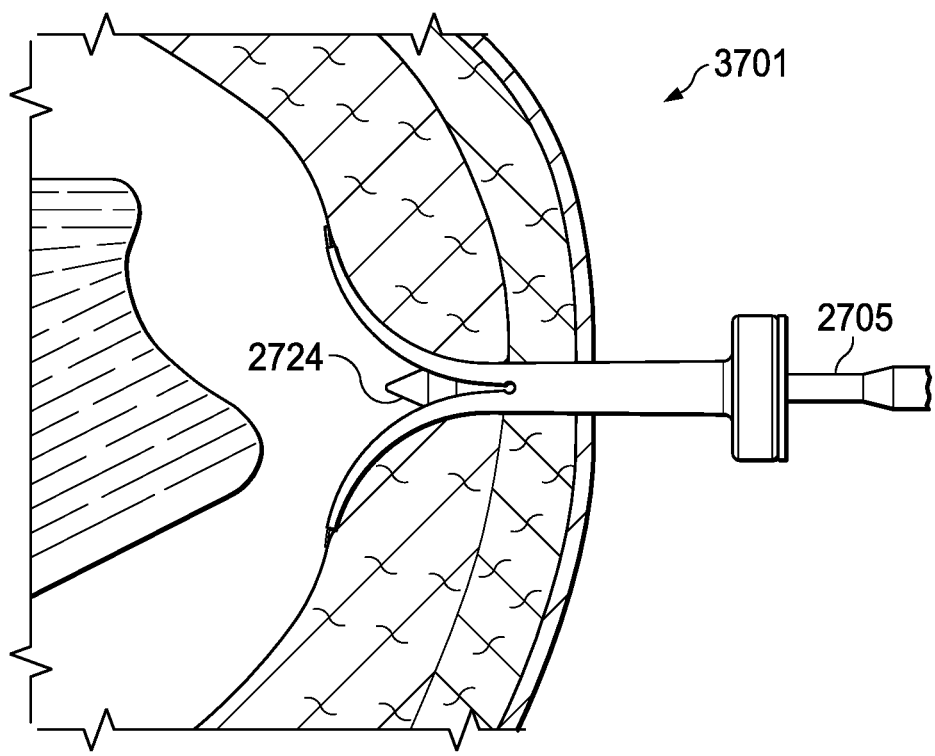
FIG. 42 depicts a side view of the alternate embodiment of the cannula device and trocar device as shown in FIG. 37, in use during shoulder surgery, and more specifically, at a time during retraction of the trocar device.
Figure 43:
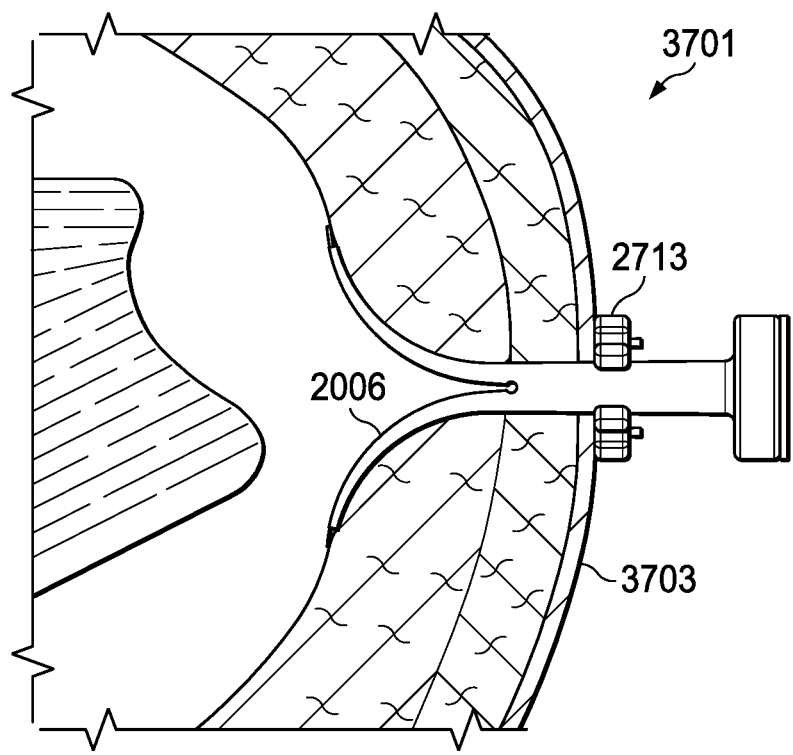
FIG. 43 depicts a side view of the alternate embodiment of the cannula device and trocar device as shown in FIG. 37, in use during shoulder surgery, the cannula device distal opening being compressed by tissue structures.
Figure 46:
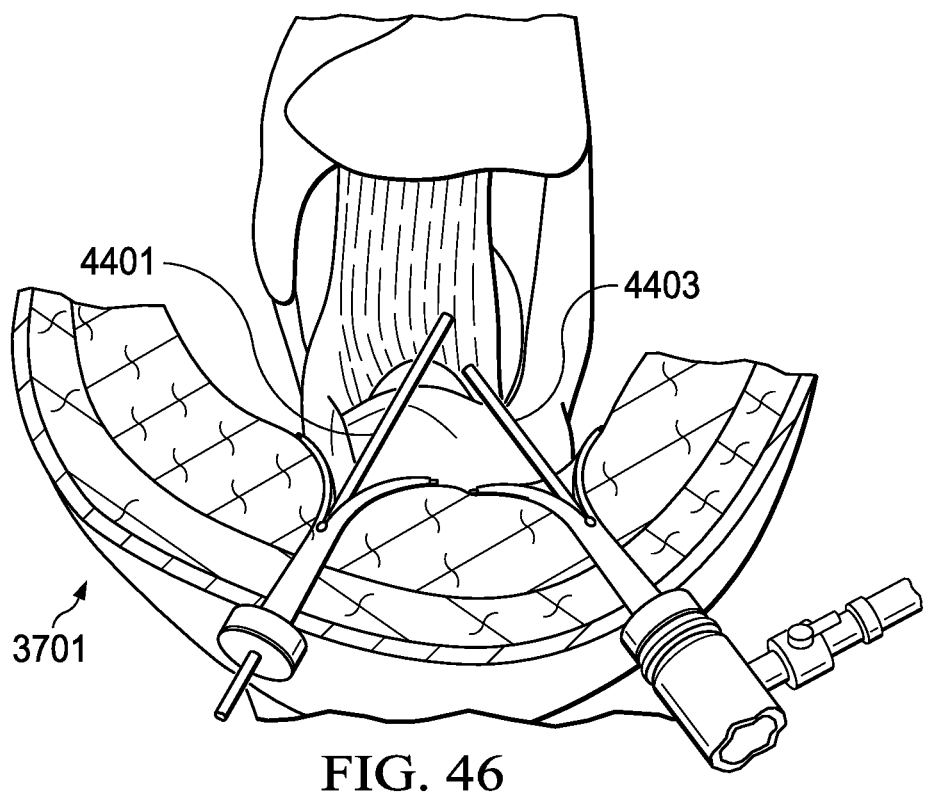
FIG. 46 depicts a side view showing two alternate embodiments of the cannula device and trocar device as shown in FIG. 37, in use during shoulder surgery, said cannula devices providing for a wide range of movements by the surgeon using surgical instruments.

FIG. 42 depicts a side view of the alternate embodiment of the cannula device and trocar device (partial view) as shown in FIG. 37, in use during shoulder surgery, and more specifically, at a time during retraction of the trocar device. Following deployment of the cannula fins, the trocar device may be extracted in a rearward movement (away from patient), allowing for the insertion of other surgical instruments/tools into the cannula. FIG. 43 depicts a side view of the alternate embodiment of the cannula device and trocar device as shown in FIG. 46, in use during shoulder surgery, the cannula device distal opening being compressed by tissue structures. The c-shaped tool (2713) may be used by the surgeon to remove the cannula device from the patient by using it to compress the tissue and the fins as the cannula is being removed.

Figure 44:
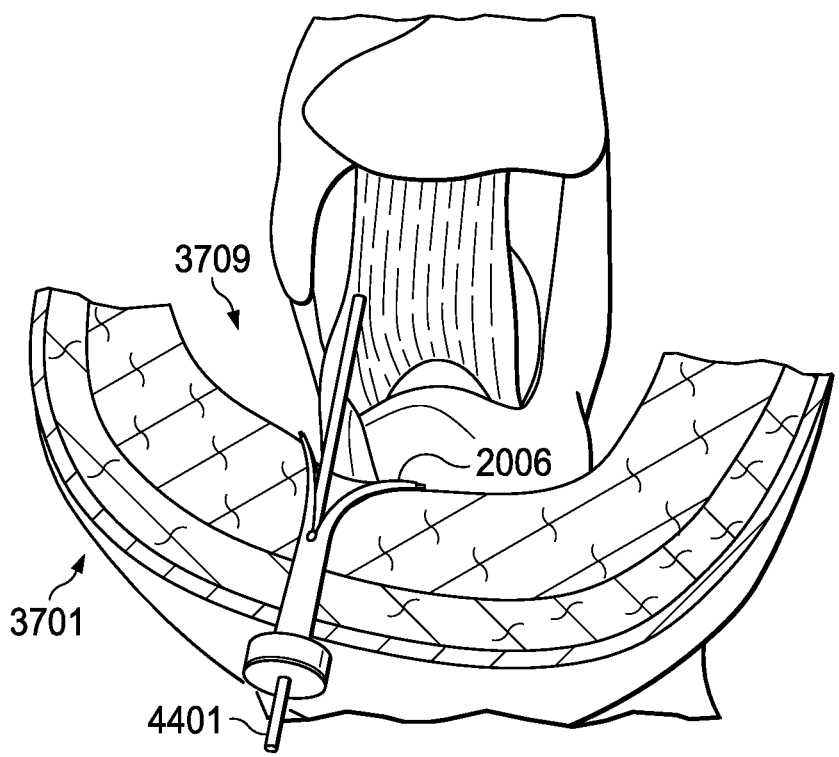
FIG. 44 depicts a side view of the alternate embodiment of the cannula device and trocar device as shown in FIG. 37, in use during shoulder surgery, a surgical instrument passing through the cannula device, said cannula device providing for a wide range of movements by the surgeon using said instrument.
Figure 45:
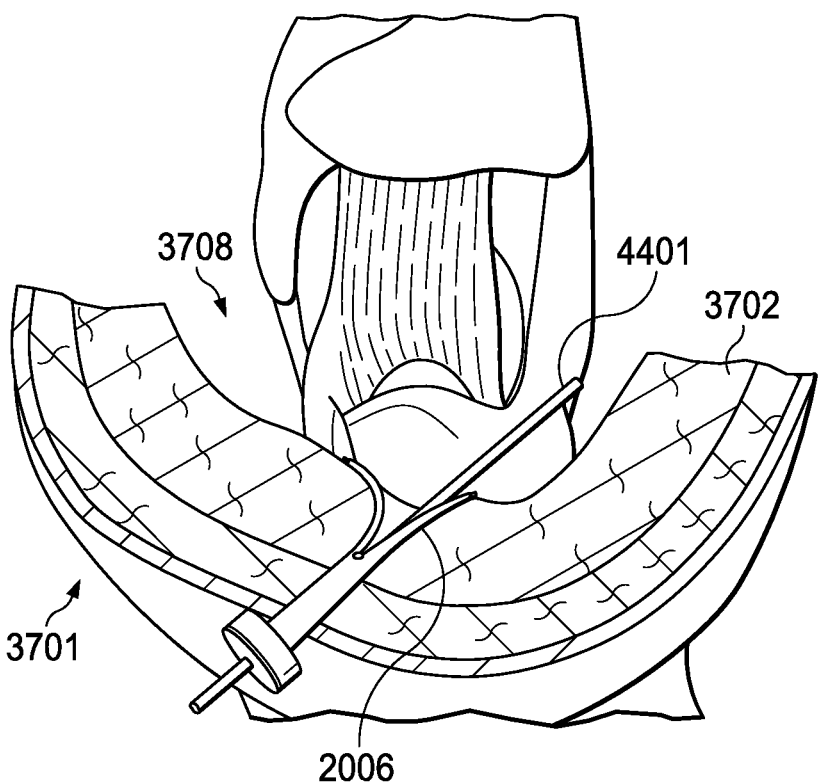
FIG. 45 depicts a side view of the alternate embodiment of the cannula device and trocar device as shown in FIG. 37, in use during shoulder surgery, a surgical instrument passing through the cannula device, said cannula device providing for a wide range of movements by the surgeon using said instrument.

Referring now to FIG. 44, depicted is a side view of the alternate embodiment of the cannula device and trocar device as shown in FIG. 37, in use during shoulder surgery, a surgical instrument (4401) passing through the cannula device, said cannula device providing for a wide range of movements by the surgeon using said instrument. FIG. 45 depicts a side view of the alternate embodiment of the cannula device and trocar device as shown in FIG. 37, in use during shoulder surgery, a surgical instrument (4401) passing through the cannula device, said cannula device providing for a wide range of movements by the surgeon using said instrument. Referring now to FIG. 46, depicted is a side view showing two alternate embodiments of the cannula device and trocar device as shown in FIG. 37, in use during shoulder surgery, said cannula devices providing for a wide range of movements by the surgeon using multiple surgical instruments (4401; 4403).

The features of the cannula device discussed above allow the cannula device to be constructed with an outer diameter less than prior art cannulas and thus, decreased cross-sectional area. In one embodiment, the outer diameter of the cannula device is approximately eight millimeters. The reduced cross-sectional area of the cannula devices provides several advantages as compared to prior art cannula devices. For example, one advantage of a decreased cross-sectional area is a reduction in tissue trauma during surgery. Another advantage of the cannula device invention is that such cannulas do not require exterior threading for retaining the cannula as do many prior art cannulas—primarily because they are unnecessary because the cannula fins secure the cannula to the patient's tissue. An even further advantage of the cannula device invention is that it provides for increased visualization during surgery as compared to prior art cannula devices.

Referring now to FIGS. 47-59, depicted are views of several embodiments of portal holder devices (and associated trocar and other devices which aid in deployment during surgery) which, in many respects, serve functions similar in nature to the cannula devices discussed herein above, but consist only of one or more flexible fins or shafts that alone or in combination with other fins/shafts, act to serve as both a conduit for surgical instruments during surgery, and also provide for adequate fluid retention during surgery. Various different embodiments of the portal holder device are shown and described herein.

Figure 47:
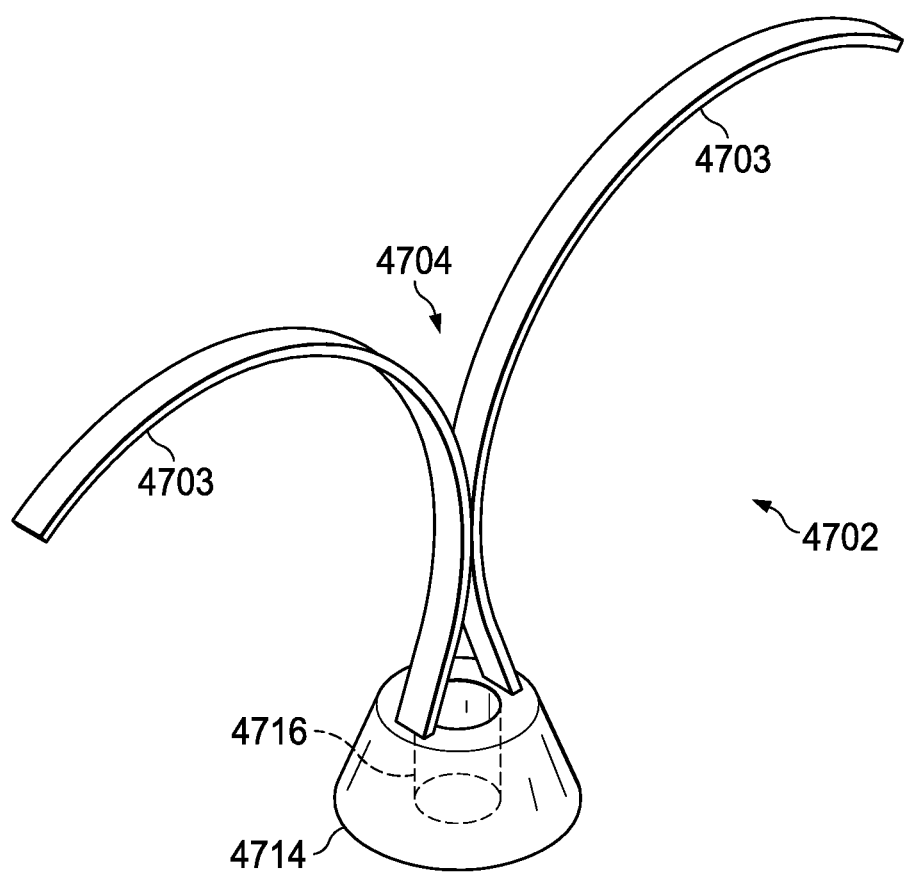
FIG. 47 depicts a perspective view of a portal holder device having a passageway with a flexible distal opening.

Referring now to FIG. 47, depicted is a perspective view of a portal holder device (4702) having a passageway with a flexible distal opening. In one embodiment, the portal holder device (4702) comprises two flexible fins (4703) joined by a conical like collar (4714) at a proximal end. The flexible fins, in one mode when not secured by a trocar device, naturally flex outwardly in an arc-like fashion, converging at a point (4704) distal to said collar. In one embodiment of the portal holder device, the flexible fins are constructed of a shape memory alloy such as Nitinol and, as explained above, may be trained (shape memory) to take on various shapes at predetermined temperature ranges. In other embodiments, the fins of the portal holder device may be constructed of other materials having flexible properties while also providing spring-like/biasing properties in the sense that they cause the fins to provide an outwardly projecting force for tissue retraction. In one embodiment, a hole (4716) formed in the collar (4714) provides a conduit or passageway through which surgical instruments and other tools used during surgery may pass during surgery. The aforementioned collar hole (4716) also provides a conduit through which a trocar device shaft may pass for engaging the distal ends of the portal device holder fins as discussed further below. Although the collar is conical in shape in the figures described herein, it is contemplated that other embodiments of the portal holder device will incorporate collars have other shapes such as, for example, a collar having an oval shaped cross-section. Other alternate embodiments of the portal holder device may also incorporate two or more fins of various lengths, depending upon the particular surgical application for which the device will be intended. Alternate embodiments of the portal holder device may employ alternate geometries by which the two or more fins may converge to provide for both fluid retention and tissue retraction. In alternate embodiments of the portal holder device, as described below, the collar hole may be threaded to receive a correspondingly threaded deployment plug which may aid in deploying the fins when at the surgical site.

Figure 48:
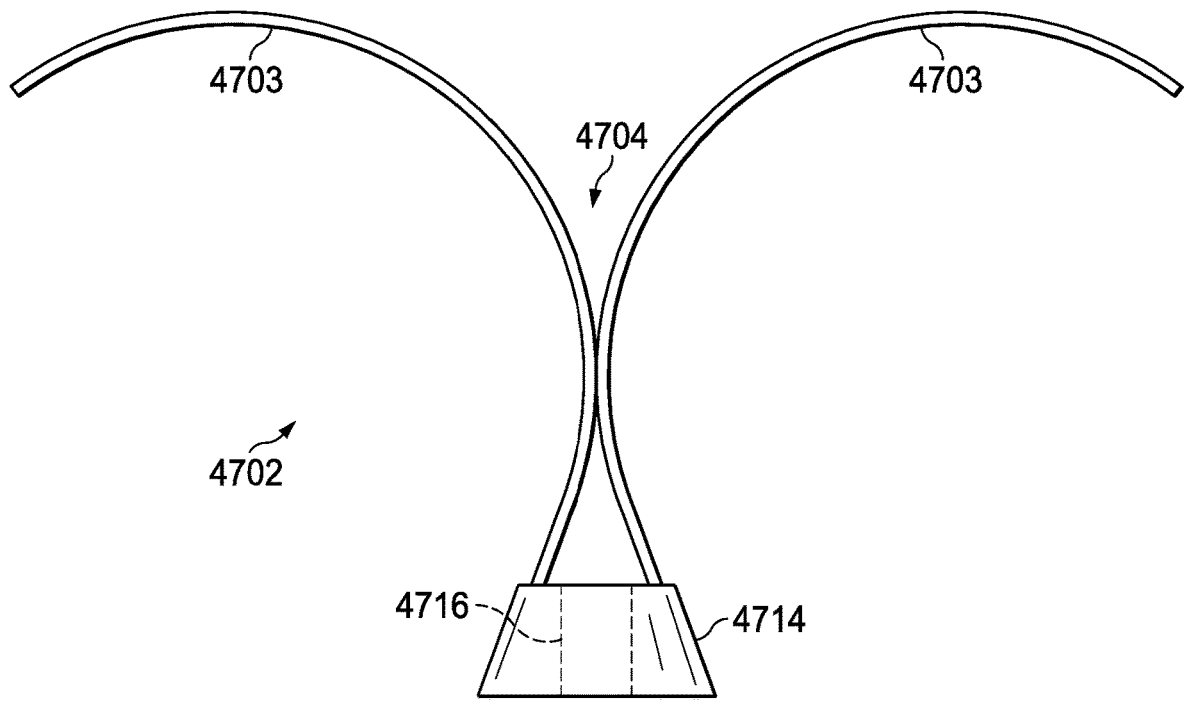
FIG. 48 depicts a side view of the portal holder device shown in FIG. 47, showing the flexible distal opening of the portal holder device in a substantially closed position.

Referring now to FIG. 48, depicted is a side view of the portal holder device (4702) shown in FIG. 47, showing the flexible distal opening of the portal holder device in a substantially closed position. In one embodiment, the portal device holder fins converge at a point (4704) distal to the collar (4714), approximately a third of the way along the length of the fins, as measured from the collar to the distal tips of said fins. The length of the fins in alternate embodiments may vary, depending upon the particular surgical application and the particular anatomy of the patient. Likewise, the fins of the portal holder device may be configured to converge at other locations along the length of the fins, and at different distances from the collar and/or distal tips of the fins—again such modifications will depend on the type of surgical application and the patient's anatomy, as well as the types of surgical instruments and other tools that are intended to pass through the portal holder device. Still referring to FIG. 48, the convergence point (4704) serves as a barrier to fluid leakage during surgical procedures and like embodiments of the cannula device discussed herein, creates a substantially impermeable seal when patient tissues further compress the convergence point once the device is deployed. The fins are configured (through shape memory training techniques or otherwise) to maintain an inwardly directed force against one another, providing such fluid leakage barrier. The principals discussed with reference to FIGS. 37-46, showing a patient's tissue bearing upon the cannula convergence point to provide a fluid seal, are equally applicable with respect to the operation and advantages of the portal device holder. Specifically, it is contemplated that during surgery, a patient's tissue will assist the portal device holder in pressing inwardly to provide a fluid barrier. Although the embodiment of the portal holder device depicted and discussed herein includes two fins, as noted above, it is contemplated that alternate embodiments of the portal device holder will include two or more fins of various geometries, various fin lengths, and connection configurations, to provide both a conduit for surgical instruments, as well as fluid retention and tissue retraction during surgery. For example, one alternate embodiment of the portal device holder may include three fins intertwined in a helical shaped configuration, wherein the twisting nature of the helical configuration can, at certain portions of the device, converge to provide for a fluid retention barrier. Utilization of shape memory alloys in constructing and "training" the fins allows for such alternate fin geometries and interconnectedness.

Figure 49:
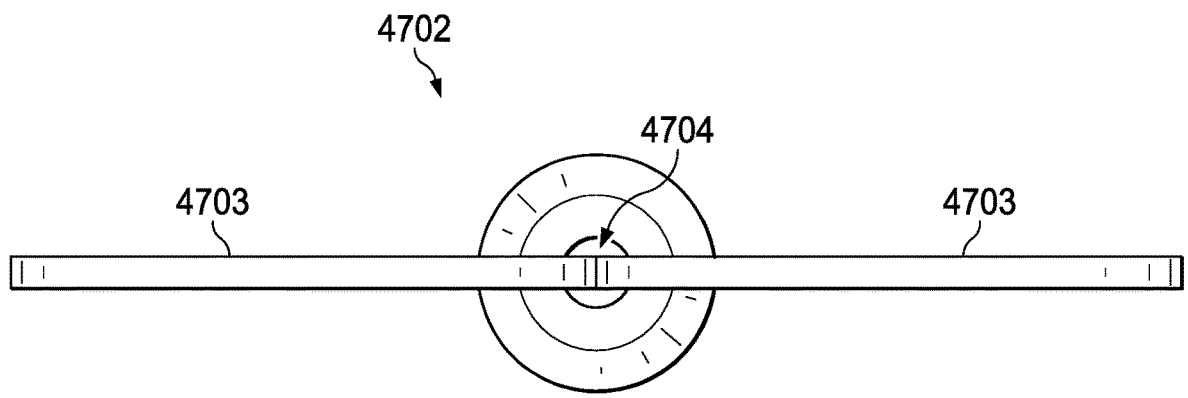
FIG. 49 depicts a top view of the portal holder device shown in FIG. 47, showing the flexible distal opening of the portal holder device in a substantially closed position.

Referring now to FIG. 49, depicted is a top view of the portal holder device (4702) shown in FIG. 47, showing the flexible distal opening (4704) of the portal holder device in a substantially closed position. While the convergence point (4704) of the portal holder device (4702) is closed in the embodiment of the device shown at FIG. 49, those of skill in the art will understand that the fins (4703) are flexible, allowing for surgical instruments and other tools to pass forward and rearward between the fins as needed with minor application of force by the surgeon. The flexibility of the fins of the portal holder device allow for a wide range of movements of instruments by the surgeon, in the same manner depicted in FIGS. 44-46 with respect to the cannula device taught herein.

Figure 50:
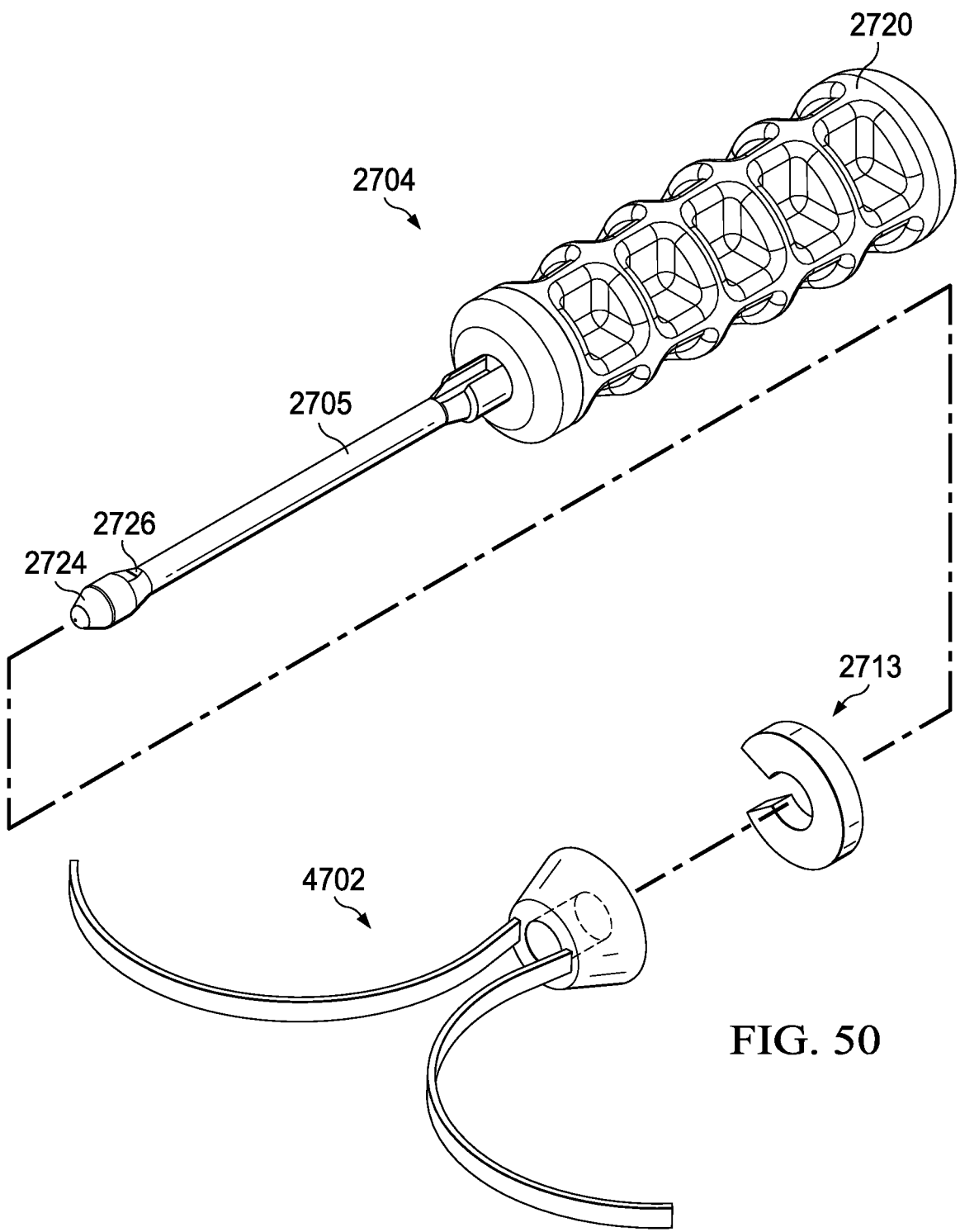
FIG. 50 depicts an exploded view of the portal holder device as shown in FIG. 47, along with an alternate embodiment of a trocar device for use in device deployment during surgery.

Referring now to FIG. 50, depicted is an exploded view of the portal holder device (4702) as shown in FIG. 47, along with an alternate embodiment of a trocar device (2704) for use in device deployment during surgery. The trocar device (2704) serves the purpose of both providing a mechanism for physically placing the portal holder device at the surgical site, and also serves to release the fins of portal holder device. Notches (2726) formed on the distal end (2724) of the trocar device shaft (2705) are shaped to receive and removably secure the distal ends of the fin shafts of the portal holder device (4702). The distal ends of the fins of the portal holder device may be inserted into the notches (2726) formed on opposite sides of the distal end of the trocar device. When inserted into the notches, the distal ends of the portal holder device are prevented from flexing outwardly. The trocar device may be constructed of any number of polymers or other materials having rigid or semi-rigid properties. A "c" shaped spacer/removal tool (2713), which also serves as a removal device, is shaped and sized to be removably secured around the proximal end of the trocar device shaft (2705), such that it is located between the distal end of the trocar device handle (2720) and the proximal collar of the cannula device when the trocar device is attached to said cannula. The spacer/removal device (2713) serves to prevent the premature deployment of the fins (4703) until the time desired by the surgical team. When the spacer (2713) is removed from the space between the distal end of the trocar device handle (2720) and the collar of the portal holder device, the trocar device may then be moved in a distal direction (generally towards the patient when the portal holder device has been inserted into a patient), and/or the portal device may be moved in a rearward direction (away from patient) while keeping the trocar device unmoved, decreasing the gap between said handle and the proximal collar, such that the distal ends of the portal holder device fins are disengaged from the notches (2726), allowing said fins to flex outwardly. In this manner, a surgeon may deploy the fins of the portal device holder at a desired time during a surgical procedure.

Figure 51:
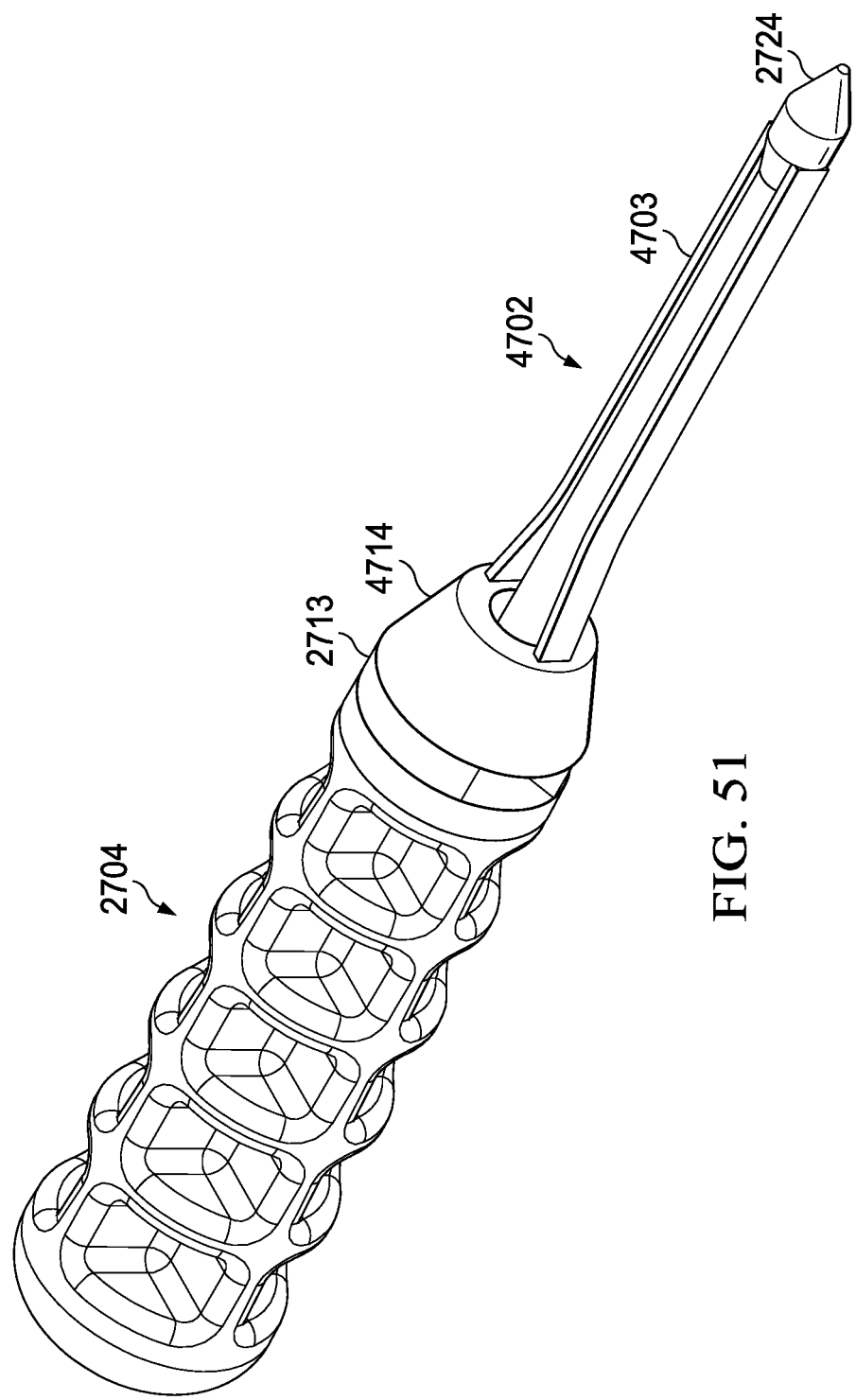
FIG. 51 depicts a perspective view of the portal holder device as shown in FIG. 47, along with an alternate embodiment of a trocar device for use in device deployment during surgery, the ends of the shafts of the portal holder device secured within notches formed on the end of the trocar device shaft.

Referring now to FIG. 51, depicted is a perspective view of the portal holder device (4702) as shown in FIG. 47, along with an alternate embodiment of a trocar device for use in device deployment during surgery, the ends of the shafts of the portal holder device secured within notches formed on the end of the trocar device shaft. The shaft of the trocar device (2704) is shown inserted into an opening (not shown) in the proximal end of the portal holder device such that the distal head (2724) of the trocar shaft protrudes from the distal end of the portal holder device. The configuration of the portal holder device and trocar device shown in FIG. 51 illustrate the appearance of such devices prior to insertion into a patient and deployment of the portal holder device. The "c" shaped spacer/removal device is removably secured between the distal end of the trocar device handle and the collar (4714) of the portal holder device.

Figure 52:
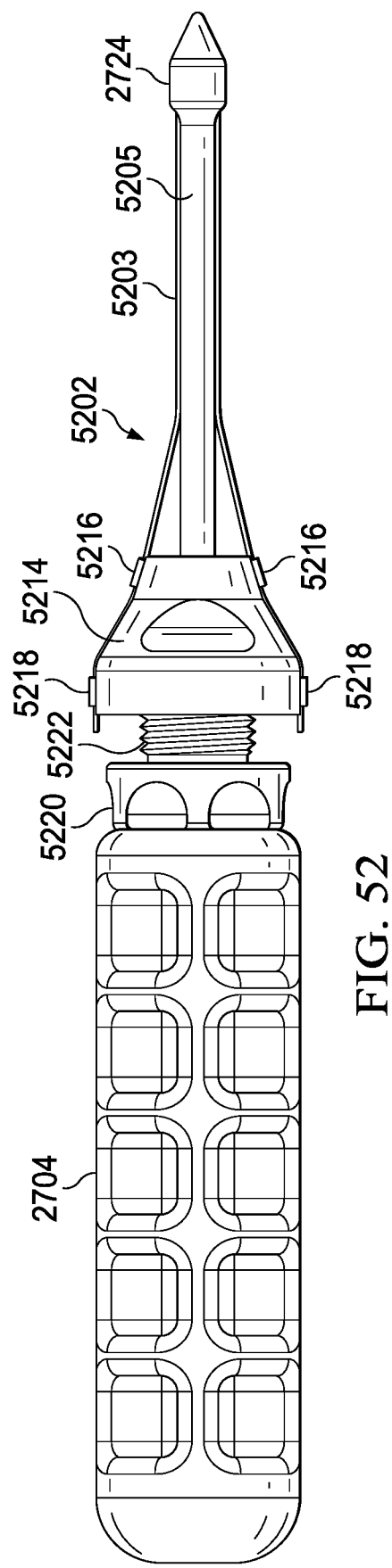
FIG. 52 depicts a side view of an alternate embodiment of the portal holder device removably mounted to a trocar device.

Referring now to FIG. 52, a further alternate embodiment of the portal holder device (5202), removably mounted to a trocar device (2704), is shown. While other embodiments of the portal holder device discussed above included flexible fins having proximal ends secured to a collar, in the alternate embodiment shown in FIG. 52, the proximal portions of the flexible fins are movably secured to the base (or "collar"), distally and proximally, allowing for the working lengths of the fins (the length of the fins from the proximal end of the collar to the distal tips of the fins) to be varied by the surgeon as desired. In the embodiment shown in FIG. 52, the proximal portions of the fins (adjacent to the collar (5214)) are secured to the collar by relatively short slots (5216, 5218) formed on outer walls of both sides of the collar. The slots (5216, 5218) are sized to receive the fins and allow them to pass through, such that the proximal portions of the fins can protrude past the proximal end of the collar. The slots are sized to provide enough friction that the fins will not move while experiencing forces typical during surgery. However, the slots are sized such that a surgeon can apply enough force to extend and retract the fins, allowing the surgeon to choose not only the working length of the fins, but the convergence point of the fins. This feature provides an additional advantage (beyond fluid retention and tissue compression) not seen in prior art cannulas in that a surgeon can make such modifications to the dimensions of the portal holder device on the fly during surgery as conditions warrant. It will be recognized that the distance between the distal end of said base member and a convergence point between said shafts, may be varied by a user by increasing or decreasing the working length of said biasing devices. Likewise, it will also be recognized that the width of a gap between the shafts of the biasing devices, at a convergence point (where the gap between the shafts is narrowest) may be varied by a user by increasing or decreasing the working length of said biasing devices.

Still referring to FIG. 52, the alternate embodiment of the portal holder device shown is in many respects similar to the embodiment shown in FIG. 51. A shaft (5205) and distal head (2724) of a trocar device (2704) is configured to pass through the collar or "base member" (5214) and fins (5203) of the portal holder device (5202). Notches (not shown) formed on the distal head of the trocar device (2724) are sized to receive the distal tips of the portal holder device prior to being deployed during surgery. A deployment plug or tool (5220) having a hole through which the shaft (5205) passes, is removably mounted to the trocar device. The deployment tool (5220) has a distal end that is threaded and sized to be received in a correspondingly sized and threaded aperture formed on the inner wall of the collar. A user of the device may rotate the deployment tool, causing the portal holder device to move rearward (away from distal head of trocar device) and ultimately, allow the distal tips of the fins to disengage from the notches securing them to the trocar device. In this manner, the fins may be deployed and flex outward. In one embodiment, the portal holder device is a surgical device for providing soft tissue compression and fluid retention during surgical procedures, said device comprising a base member having an aperture extending from a proximal end to a distal end; and a plurality of flexible biasing devices attached to said base (or "collar"), said biasing devices having shafts distally extending from said base, wherein said shafts are naturally biased in an outward direction, wherein said biasing devices are flexible such that, following insertion into a patient during a surgical procedure, at least a portion of said shafts are compressed inwardly to form a substantially impermeable seal.

Figure 53:
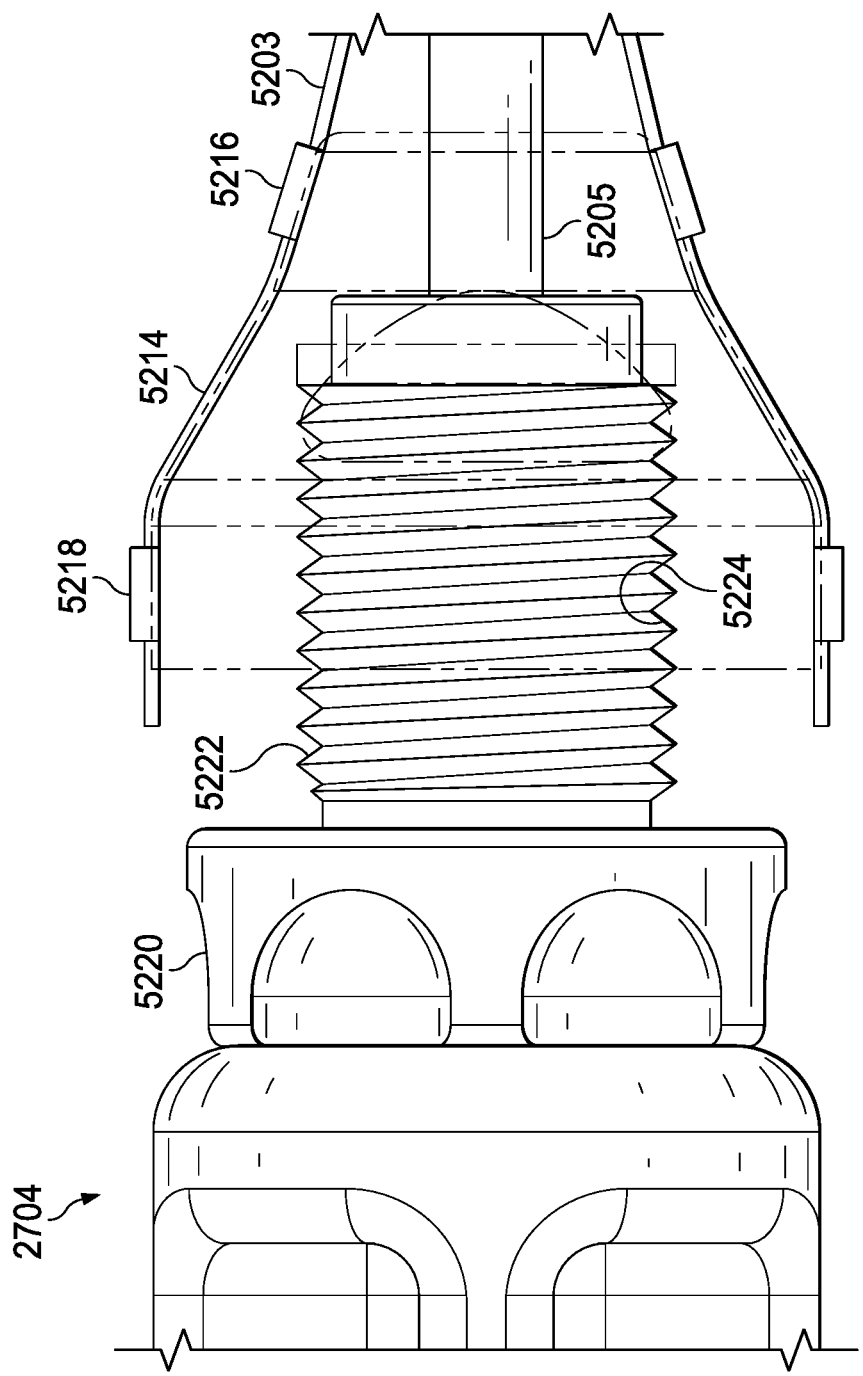
FIG. 53 depicts a side partial view of the alternate embodiment of the portal holder device, deployment plug, and trocar device as shown in FIG. 52.

Referring now to FIG. 53, a side partial view of the alternate embodiment of the portal holder device, deployment tool, and trocar device as shown in FIG. 52. In this embodiment, the fins (5203) (in one embodiment, comprising a shape memory alloy) of the portal device can be more easily seen to pass through the notches (5216, 5218) formed on the outer walls of the collar (5214) through which passes the shaft (5205) of the trocar device (2704). As previously described herein, the slots serve to secure the fins to the collar while allowing movement (extension and retraction) with an application of the requisite amount of force by the surgeon (or other person such as, for example, a nurse or physician's assistant prepping the device for surgery). In alternate embodiments, the proximal ends of the fins may be coated with a soft material such as rubber or other polymer to prevent any damage from inadvertent contact with the tips of said fins. Those of skill in the art will recognize that structures, other than notches, may be used to movably secure the fins to the collar in alternate embodiments of the portal holder device. Likewise, in other alternate embodiments, the proximal portions of the fins may pass through the body of the collar instead of remaining on the outside of the collar as shown in FIG. 53. The collar may also be constructed in various other shapes in alternate embodiments of the portal holder device. In one embodiment, the deployment tool (5220) mounted to the trocar device but is free to rotate about the axis of the trocar shaft (5205). A structural obstruction (not shown) may be placed on the threads (5222) of the deployment tool to act as a stop limiting the travel of the deployment tool (5220).

Figure 54:
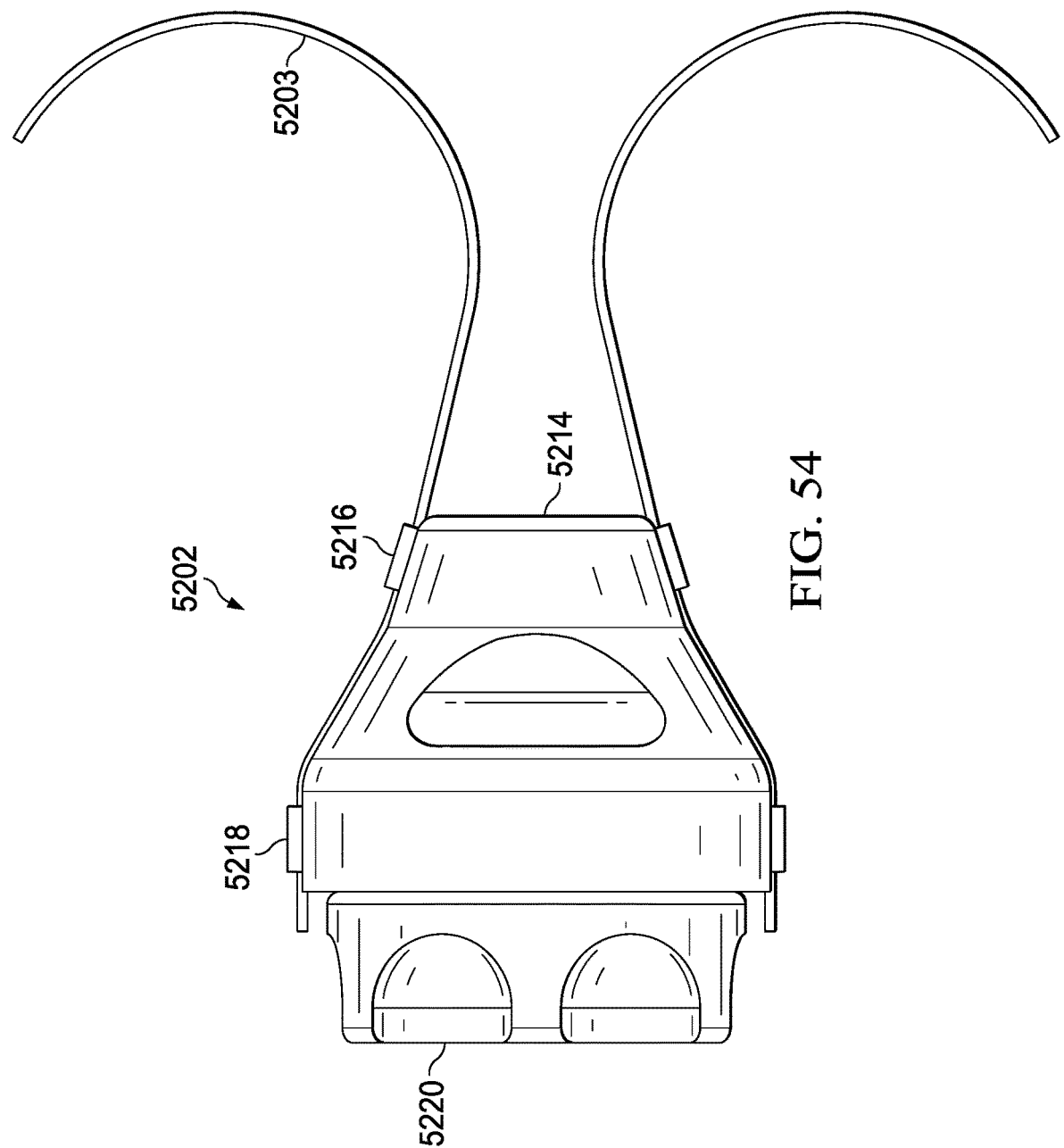
FIG. 54 depicts a side view of the alternate embodiment of the portal holder device as shown in FIG. 52.

Referring now to FIG. 54, shown is a side view of the alternate embodiment of the portal holder device (5202) that appears in FIG. 52. The flexible fins (5203) of the portal holder device (5202) have a naturally outward curve and are, in one embodiment, constructed of a shape memory alloy. While a sizable gap exists between the fins (5203) of the portal holder device shown in FIG. 54, it is contemplated that the fins may be formed such that the gap can be of greater or lesser width than what is shown. Further, because the fins are capable of being extended and retracted, the working length of the fins may be modified and the gap width likewise modified. Both of the foregoing modifications may be desired, depending on a number of factors such as the type of surgery being performed, the anatomy of the patient (for example, width of tissue to traverse to access surgical site), and the types of instruments and other tools which are intended to pass through the gap between the fins.

Figure 55:
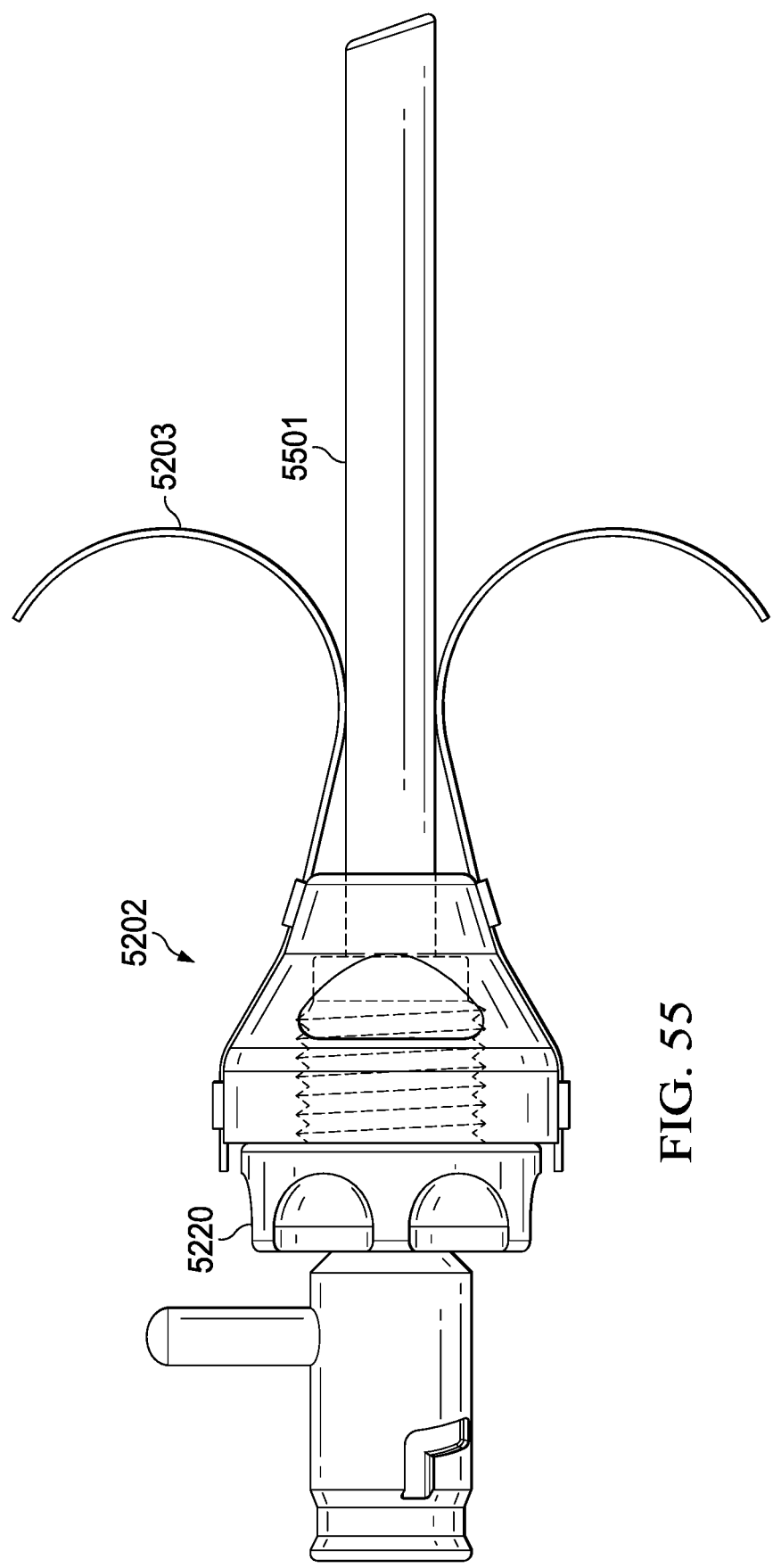
FIG. 55 depicts a side view of the alternate embodiment of the portal holder device as shown in FIG. 52, said device being removably mounted to a cannula.

Referring now to FIG. 55, a side view of the alternate embodiment of the portal holder device as shown in FIG. 52, said device being removably mounted to a scope cannula (5501), is shown. This figure is shown to illustrate that in alternate embodiments of the portal holder device, the device may be mounted on device other than the trocar devices previously discussed herein. Now referring to FIG. 56, shown is a partial perspective view of the alternate embodiment of the portal holder device, deployment plug, and trocar device as shown in FIG. 52. The distal tips of the fins (5203) of the portal holder device, when in a non-deployed state, may be temporarily secured within a hood formed on the distal head of the trocar device (2726). As previously discussed here in connection with other embodiments of cannula devices and portal holder devices, the fins are deployed when movement of the portal holder device with respect to the trocar device, cause the distal tips of the portal holder device to be dislodged from the distal end of the trocar device. Referring to FIG. 57, an alternate embodiment of a trocar device usable to deploy embodiments of the portal holder device during surgery.

Referring now to FIG. 58, a side view of a further alternate embodiment of a portal holder device (5802) and deployment tool (5820) mounted to an alternate embodiment of a trocar device for use during surgery. In this alternate embodiment, the proximal end of the collar (5814) tapers outward, away from the axis defined by the trocar device shaft (5805). This outward tapering, adjacent to the most proximal notch (5818), causes the proximal portion of the fin to be deflected away from the proximal opening (not shown) of the collar. In this manner, the degree of possible unwanted contact by the fins (for example, with the hands of the surgeon and/or surgical instruments) is decreased. Referring now to FIG. 59, shown is a side view of further alternate embodiments of portal holder devices removably mounted to opposing sides of an alternate embodiment of a trocar device, for use during surgery. It may be desirable, in some surgical procedures, to deploy portal holder devices on opposite sides of the surgical site. Portal holder devices mounted on opposing sides of a modified trocar device may be used in such situations.

Figure 60:
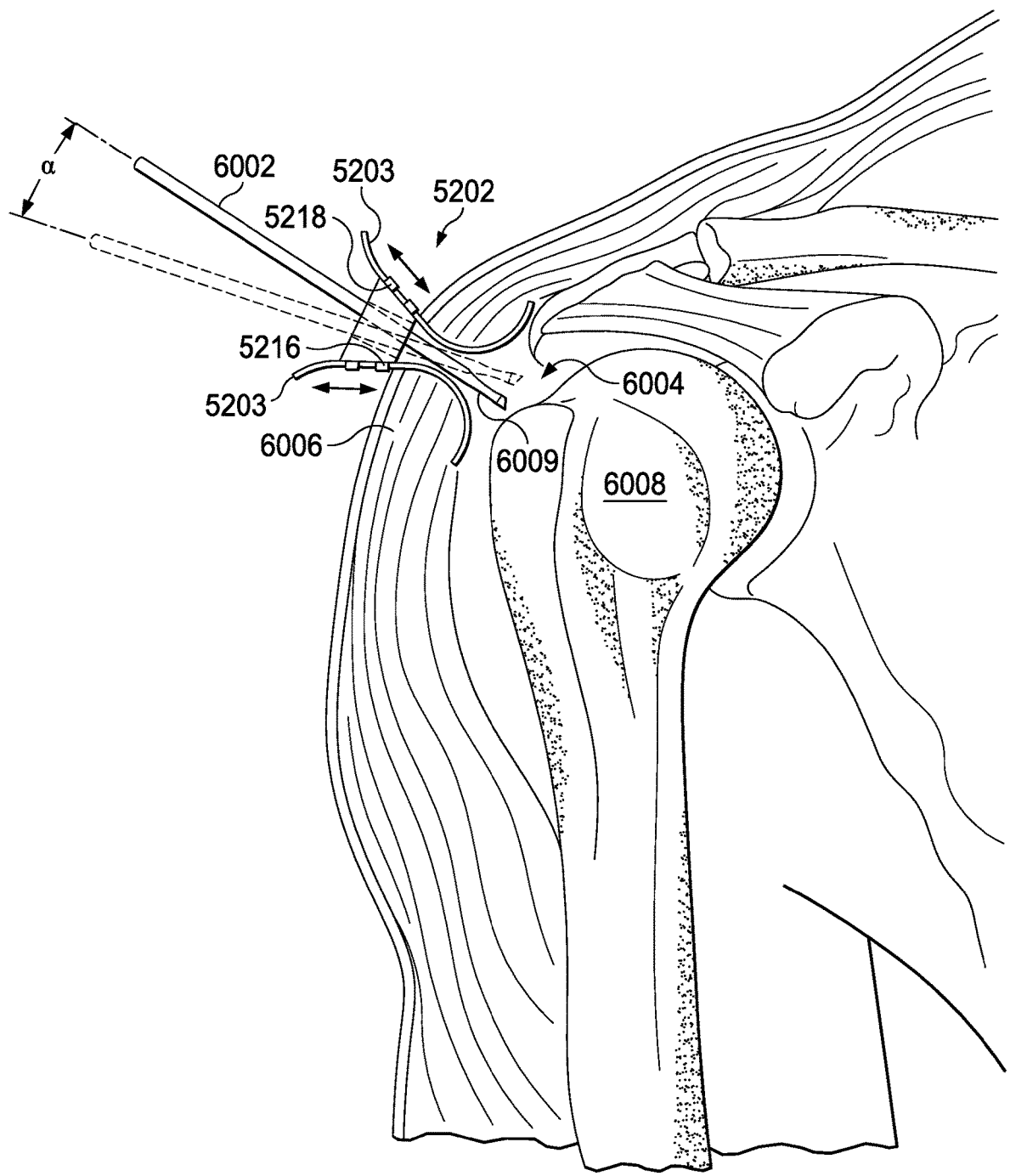
FIG. 60 depicts a cutaway view of the alternate embodiment of the portal holder device invention as shown in FIG. 52, demonstrating how the shafts may be extended and retracted as desired during shoulder surgery.

Referring now to FIG. 60, depicted is a cutaway view of an embodiment of the portal holder device invention in use during shoulder surgery. Once inside a patient, the trocar is removed from the portal holder device and the fins naturally flex to their outwardly-biased position. FIG. 42 depicts such an event. As shown, the portal holder device (5202) forms a portal in the patient's skin and outer tissue (6006) through which surgical instruments (6002) may pass. The outwardly biased flexible fins (5203) of the portal holder device exert pressure on the tissue (2006) and assist the surgeon in compressing the tissue (2006) to allow for a greater working cavity (6004) and exposure of the surgery site (6008). Because of the compressive effect of the flexible fins (5203) on the tissue (6006), the length of the portal holder device may be made relatively short compared to conventional cannula devices. This shortened working length of the fins results in a shortened passage way through the portal holder device that, consequently, allows a greater working angle (shown on the figure as the Greek letter "a") for the surgeon's tools (6002), which improves the surgeon's access to the surgery site and reduces the need for physical manipulation of the cannula during surgery. Incisions may vary in size from a quarter of an inch to an inch depending upon the application. This device also has larger scale applications for "mini-open" surgery. This would utilize the same concept without the arthroscope or laparoscope. Although the present embodiment is described in use during shoulder arthroscopy, one of ordinary skill will understand that the device may be employed in essentially any arthroscopic, laparoscopic, or other types of endoscopic surgery requiring the surgeon to establish a working port in the tissue of a patient. Moreover, it should be noted that alternate embodiments of the portal holder device invention may be utilized to perform endoscopic surgery on subjects other than humans such as, for example, animals such as dogs, cats and livestock. Those of ordinary skill in the art will recognize that the dimensions of the portal holder device invention will require modification depending upon the anatomical structures of the particular subject of the surgery in which the invention is utilized, as wells as the type of endoscopic surgery being performed. The devices in methods described herein may be utilized in numerous types of surgeries including, but not limited to, surgeries associated with the knee, hip, and elbow, as well as the spine and anywhere surgeons are accessing the body. In spine surgery, the minimally invasive instruments currently used generally utilize a guidewire which is a metallic small-diameter pin. A cannulated obturator could be obtained inserted over the guide pin with the attached biasing fins in a very similar fashion. Similar benefits of the devices and methods taught herein exist for open surgery. Using an obturator with or without a guidepin for localization to insert the retraction device allows for very low-profile insertion and enhanced retraction. It should be noted that while the portal holder device is not shown in FIGS. 37-46, the concepts illustrated in such figures, including the means by which the portal holder device is inserted, deployed, works to retract and compress tissue once deployed to provide better access to the surgical site and a wider range of movement by the surgeon, and provides fluid retention, are equally applicable to the embodiments of the portal holder device described herein.

Figure 61:
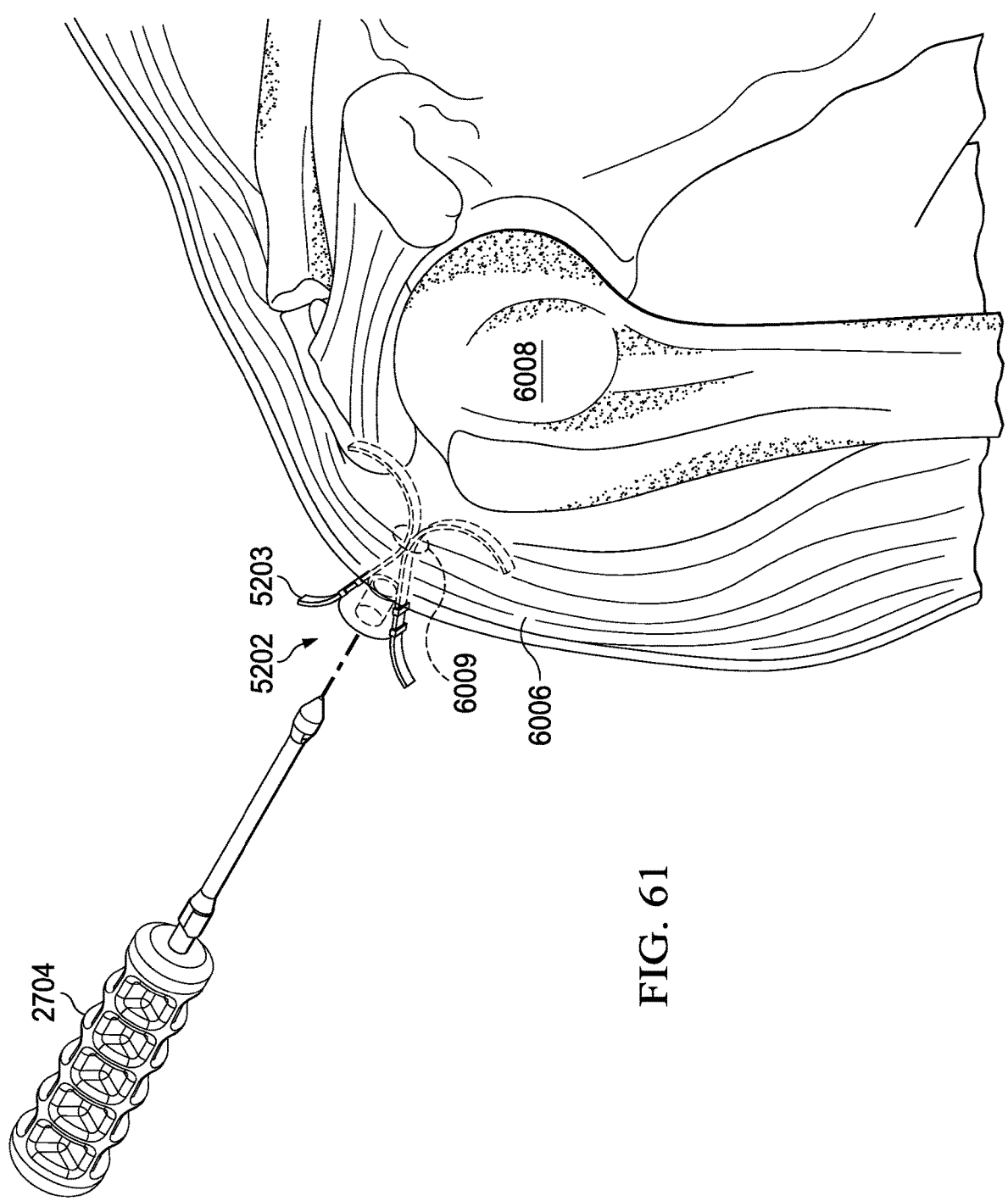
FIG. 61 depicts a cutaway view of the alternate embodiment of the portal holder device as shown in FIG. 60, as well as a trocar device used to deploy the device during surgery.
Figure 62:
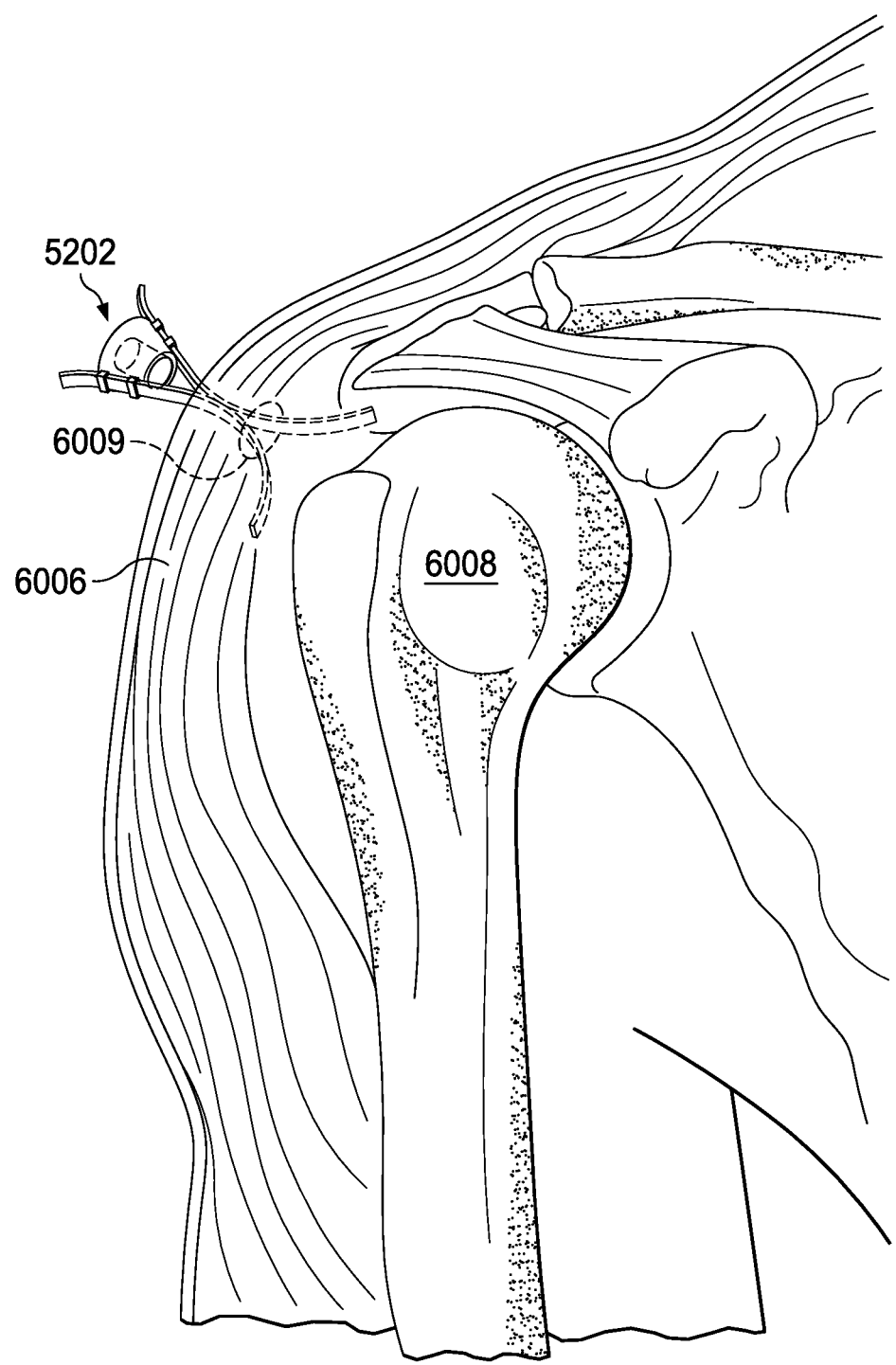
FIG. 62 depicts a cutaway view of the alternate embodiment of the portal holder device as shown in FIG. 60, having shafts that may be extended and retracted as desired during shoulder surgery.

Once the distal ends of the fins/shafts are no longer secured in the notches, said fins (5203) will be free to flex in an outward direction as shown in FIG. 61 and FIG. 62. The flexible fins of the portal holder device assist the surgical team in compressing the patient's tissue (6006) so that a greater working cavity is formed, providing better exposure of the surgery site (6008). The flexible opening, positioned during surgery within the patient and directly adjacent to the surgical site, provides for enhanced fluid/gas retention during the surgical procedure.

Referring now to FIG. 61, depicting a cutaway view of the embodiment of the portal holder device (5202) as shown in FIG. 54. At the termination of surgery, or at any time it is desirable to remove the portal holder device, a c-shaped removal tool (not shown) may be mounted on the outer body of the portal holder device and used to apply inward pressure on the fins (5203) to aid in removal from the patient. In one embodiment previously described, the removal tool is configured in a "c" shape to engage the proximal end of the shaft of the trocar device and, as previously described herein, to be employed during the deployment of the portal holder device from the trocar so as to release the outwardly biased fins.

Referring now to FIG. 62, depicting a cutaway view of the embodiment of the portal holder device (5202) being used in shoulder surgery as shown in FIG. 60. In one embodiment, the portal holder device (5202) may be removed from the patient, utilizing a c-shaped removal tool (not shown) by mounting the tool on the outer surface of the portal holder device, grasping and gently pulling the device away from the patient, while at the same time sliding the tool in a distal direction down the portal holder device body towards the patient. It is contemplated that the fins may also be retracted, as previously described herein and thereby aid in removal of the portal holder device from the patient.

Figure 63:
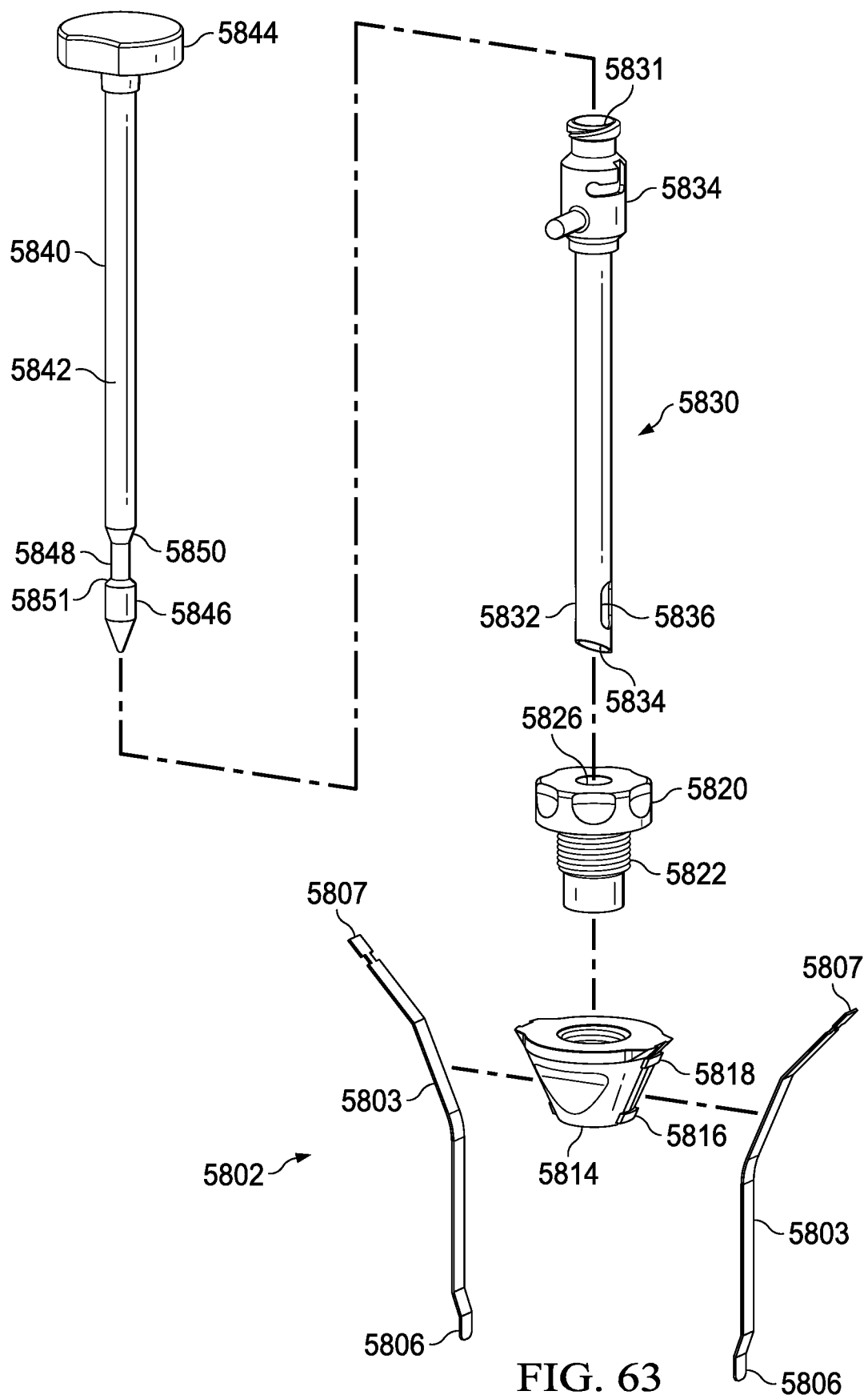
FIG. 63 depicts an exploded view of the alternate embodiment of the portal holder device as shown in FIG. 58, said portal holder configured for mounting on an embodiment of a surgical device deployment apparatus.
Figure 68:
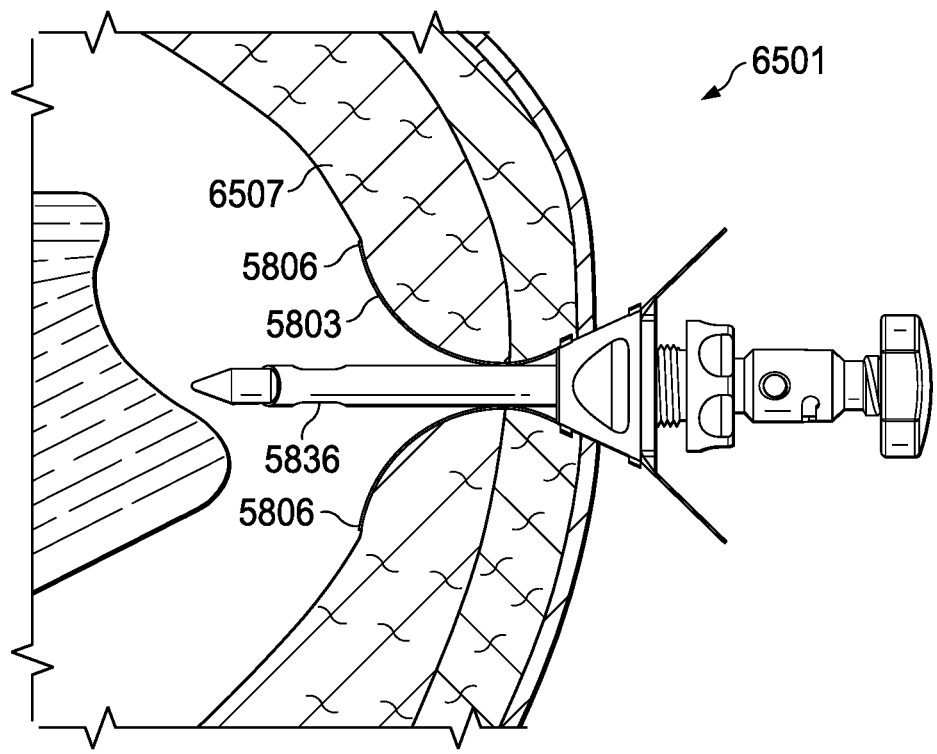
FIG. 68 depicts a side view of the alternate embodiment of the portal holder device, obturator, and cannula as shown in FIG. 65, in use during shoulder surgery, and more specifically, at a time just following deployment of the shafts of the flexible fins of the portal holder device.
Figure 69:
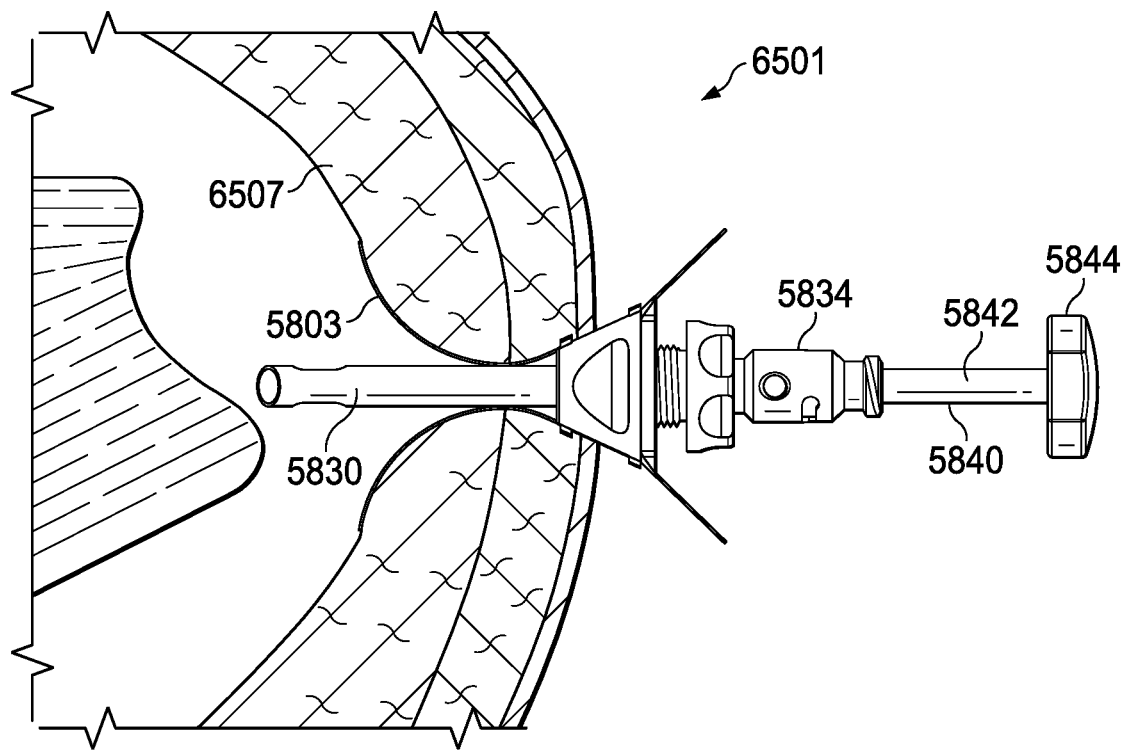
FIG. 69 depicts a side view of the alternate embodiment of the portal holder device, obturator, and cannula as shown in FIG. 65, in use during shoulder surgery, and more specifically, at a time following deployment of the shafts of the flexible fins of the portal holder device as the obturator is moved proximally (towards surgeon) and is being removed from the portal holder device and cannula.
Figure 70:
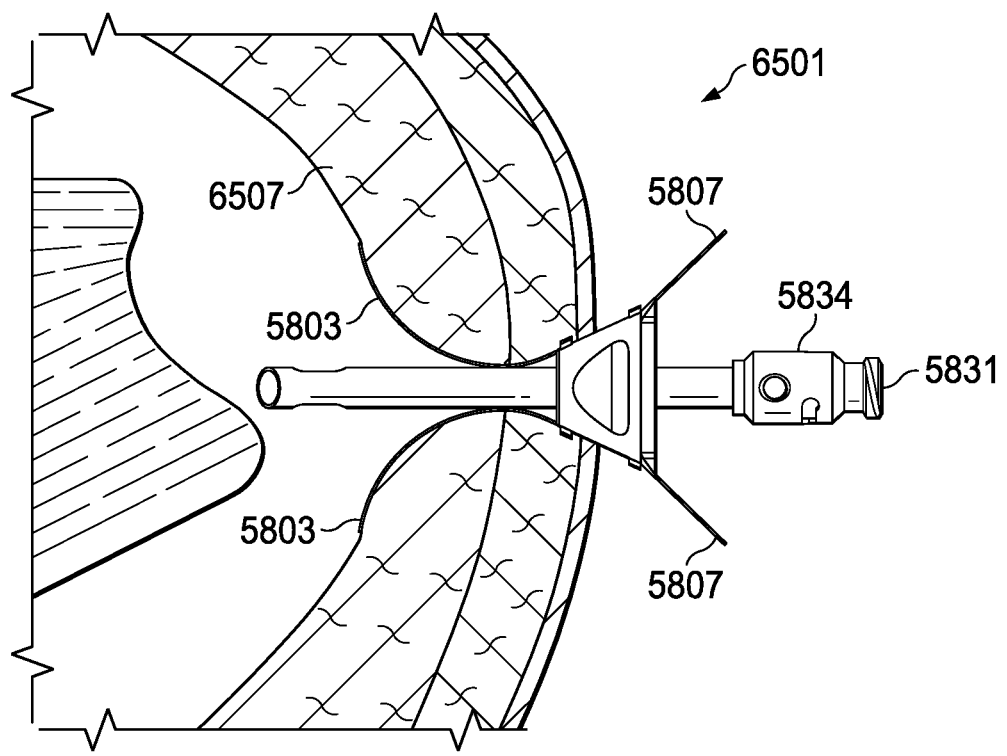
FIG. 70 depicts a side view of the alternate embodiment of the portal holder device, obturator, and cannula as shown in FIG. 65, in use during shoulder surgery, and more specifically, at a time following removal of obturator from the portal holder device and cannula.

Referring now to FIG. 63, depicting an exploded view of the alternate embodiment of the portal holder device (5802) as shown in FIG. 58, said portal holder device configured for mounting on an embodiment of a surgical device deployment apparatus comprising, in one embodiment, an improved obturator device (5840) and an improved cannula device (5830). The portal holder device (5802) comprises a plurality of flexible fins (5803) preferably composed of a shape memory alloy such as Nitinol. The flexible fins (sometimes referred to herein as "biasing devices") are naturally biased, due to the properties of the shape memory alloy that can be "tuned" or "trained" to take a certain shape at certain temperatures, to flex outwardly away from an axis defined by the shafts of the obturator (5840) and cannula (5830). Although not shown in FIG. 63, it is distal ends (5806) of the flexible fins (5803) that flexed in an outward direction when deployed (see FIGS. 68-70 showing the flexible fins outwardly flexed following deployment of the portal holder device). The proximal ends (5807) of the flexible fins (5803) are also naturally biased in an outward direction so as to conform to the conically shaped exterior surface of the collar (5814) on which the flexible fins are mounted when in use (the flexible fins are removable from the collar when not in use). As discussed above, the flexible fins may be mounted to the collar (5814), in one embodiment, by sliding the fins through the proximal notches (5818) and distal notches (5816) formed on the exterior surface of the collar. The "working length" of the flexible fins, referring to the length of the flexible fins from the proximal end of the collar to the distal tips of the fins (5806), may be selectively increased and decreased by a user (for example, by a surgeon or assistant) by sliding the flexible fins distally and proximally in the notches (5816, 5818) as described above.

It should be noted that although FIGS. 63-72, showing various embodiments of surgical device deployment apparatuses, have embodiments of portal holder devices mounted thereon, it is contemplated that cannula devices of the type shown in FIGS. 26 and 30 may likewise be mounted on the surgical device deployment apparatuses described herein. The distal ends (2302) of the biasing devices of such cannula devices being formed to be removably mounted for deployment within the distal apertures (5836) of the embodiments of the improved cannula (5830) as shown in FIGS. 63-72. Indeed, other types of surgical devices, including types of devices not characterized as cannulas or portal holder devices, may in alternate embodiments, be mounted upon and deployed on the surgical device deployment apparatuses described herein. It is contemplated that the surgical device deployment apparatuses herein, with only minor modifications in to the size and shape of the cannula and obturator (as well as possible necessary modifications to the size/shape/ and number of cannular apertures), may be utilized to deploy other types of surgical devices in all types of surgeries.

Still referring to FIG. 63, a deployment tool or "plug" (5820) has a threaded shaft (5822) for removably engaging a correspondingly threaded interior surface of the collar (5814). The deployment plug is not essential and may be absent in alternate embodiments. A hole (5826) is formed through the center of the deployment plug as shown, the hole being sized to allow for the passage of the cannula shaft (5832) and obturator shaft (5842). The improved cannula (5830) of the surgical device deployment apparatus has, in one embodiment, a generally cylindrical shaft having an exterior surface. On the inside of the cannula shaft, an interior surface defining a lumen runs the length of the cannula from a proximal end (5831) to a distal end (5834). Formed on a distal portion of the cannula are a plurality of apertures (5836), the apertures being formed on an exterior surface of the cannula shaft and into the cannula lumen. It is contemplated that the distal portion of the cannula on which the plurality of apertures are formed may vary in distance from the distal end of the cannula, depending on the particular surgical application and the particular type of surgical device being mounted on the surgical device deployment apparatus. As discussed below, the distal tips of the portal holder device are intended to protrude through the cannula apertures and into the cannula lumen where they are secured in a pre-deployment configuration. The lumen of the cannula allows for the passage of the obturator (5840), and also provides a space into which the distal ends (5806) of the flexible fins (5803) may be lodged prior to being deployed (discussed further below in connection with FIG. 64). In one embodiment of the cannula, a "J-Lock" interlock structure may be used for attachment of scope devices and other devices. An improved obturator (5840) with a shaft having a distal end (5846) is configured for insertion into the proximal end (5831) of the cannula lumen, protrudes through the distal end (5834) of the cannula, and further passing through the hole (5826) on the deployment plug (if present) and hole formed in the collar (5814). Indeed, the obturator shaft is sized for and insertable into the lumen of the correspondingly sized cannula lumen such that in one pre-deployment mode of operation of said surgical device deployment apparatus, the reduced diameter portion of the obturator is aligned with the plurality of apertures of said cannula.

The obturator also includes a reduced diameter portion (5848) on a distal portion of the obturator shaft (5842). As explained in detail below, the reduced diameter portion (5848), which is configured to be aligned with or adjacent to the distal apertures (5836) of the improved cannula prior to portal holder device deployment (one mode of operation of the surgical device deployment apparatus occurs in a pre-deployment configuration), provides a space for the distal ends (5806) of the flexible fins to be lodged and secured prior to deployment of the fins. In one embodiment of the obturator, a distal deployment surface (5851) of the obturator may exist between the surface of the distal end of the obturator (5846) and the surface of the reduced diameter portion (5848) of the obturator. The distal deployment surface of the obturator may, in various embodiments, have a surface that is perpendicular to the exterior surface of the distal end of the obturator and reduced diameter portion. In other embodiments, the distal deployment surface (5851) of the obturator may taper more gradually between the surface of the distal end of the obturator and the reduced diameter portion. In one embodiment of the obturator, a proximal deployment surface (5850) may exist between the obturator shaft (5842) and the reduced diameter portion (5848). Like the distal deployment surface, the proximal deployment surface may be perpendicular to the surface of the obturator shaft and the reduced diameter portion or, as shown in FIG. 63, more gradually taper between the two foregoing surfaces. In one embodiment, the distal deployment surface of the obturator, when the obturator is moved rearward/proximally by a user while keeping the cannula and collar of the portal holder device relatively stationary, abuts the distal ends of the flexible fins, causing said fins to be moved in the proximal direction (away from the patient in a surgical setting), which ultimately with continued rearward movement of the obturator causes the dislodgement of such fins from the reduced diameter portion and cannula apertures. In particular, the distal deployment surface (5851) of the obturator pushes the distal ends of the flexible fins proximally away from the distal end of the cannula such that the natural outward biasing of the fins causes the fins to be dislodged from the cannula apertures. The notches (5818, 5816) securing the flexible fins of the portal holder device, as noted above, allow for the distal and proximal movement of the flexible fins or in other words, for the adjustment of the working length of the fins. In alternate embodiments, the proximal deployment surface (5850) of the obturator adjacent to the reduced diameter portion may also be shaped to facilitate dislodgement of the flexible fins. The obturator includes, in one embodiment, a proximally mounted handle (5844) for facilitating the movement of the obturator by a user.

Figure 64:
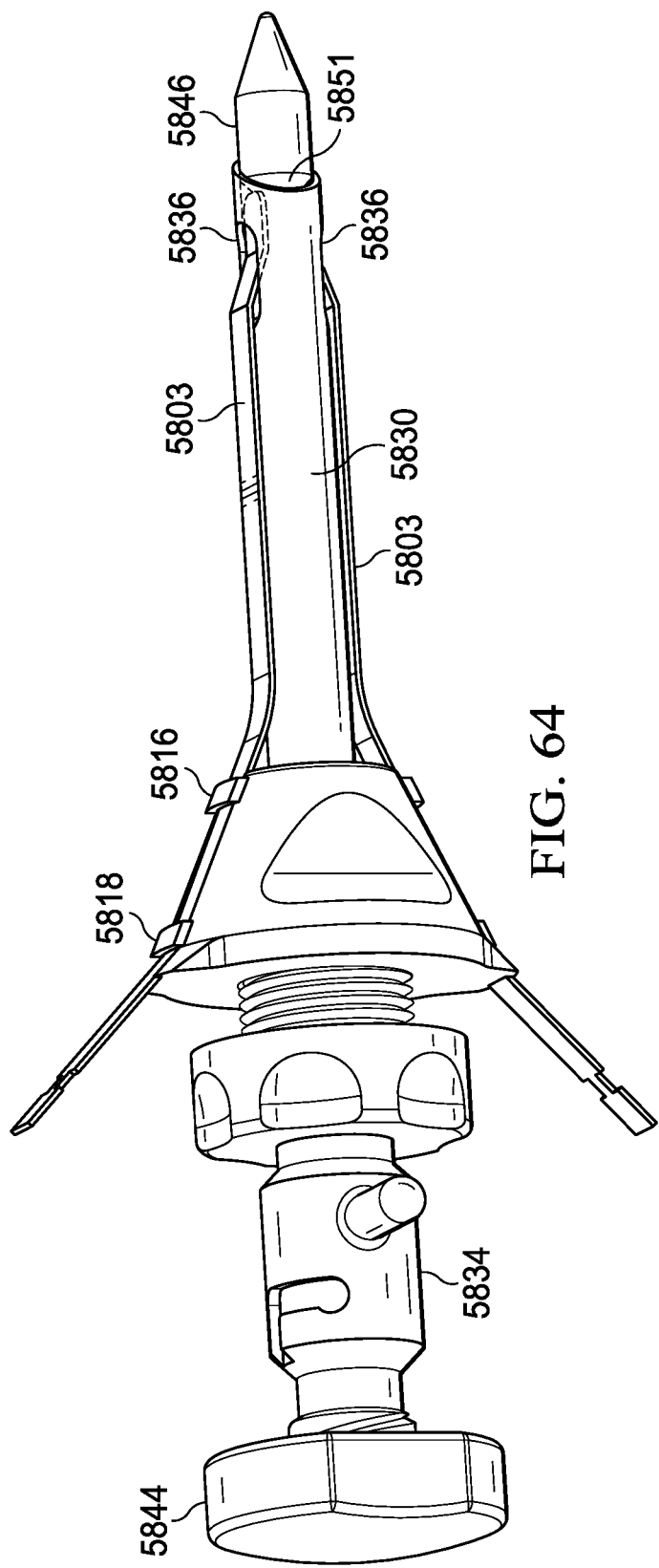
FIG. 64 depicts a perspective view of the portal holder device mounted for deployment onto the surgical device deployment apparatus as shown in FIG. 63.

Referring now to FIG. 64, depicting a perspective view of an embodiment of the portal holder device mounted for deployment onto the embodiment of the surgical device deployment apparatus as shown in FIG. 63. When the improved obturator (5840) is positioned inside the improved cannula (5830) of the surgical device deployment apparatus, the distal end of the obturator (5846) is preferably located distally (towards the patient during surgery) of the plurality of apertures (5836) formed on the cannula (5830). In one embodiment, the apertures (5836) of the cannula (5830) are oblong in shape, having an increased length along the length of the cannula, as compared to the width of the apertures. The oblong shape of the cannula apertures (5836) allows for easy insertion of the distal tips (5806) of the flexible fins of the portal holder device or other surgical devices (for example, a cannula with flexible fins as discussed above). In one embodiment, the size of the cannula apertures (5836) are sized to receive correspondingly sized distal tips (5806) of the flexible fins of the portal holder device or other surgical device intended for mounting on the cannula.

As discussed above, in the pre-deployment configuration as shown in FIG. 64, the cannula apertures are aligned with or adjacent to the reduced diameter portion (5848) of the obturator shaft such that the distal ends of the flexible fins of the portal holder (or in other embodiments, distal ends (2302) of the cannula biasing devices) may be inserted or lodged through the apertures (5836) and into the reduced diameter portion (5848) of the obturator shaft. In this manner, the distal ends of the flexible fins are secured at least temporarily such that the fins are prevented from prematurely, prior to the time of intended deployment, flexing outwardly. The temporary lodging of the distal ends of the flexible fins within the lumen of the cannula also prevents the distal ends from inadvertently coming into contact with human tissue or other objects prior to deployment and as they traverse through the incision to the surgical site. This compact manner of device mounting and deployment is an advantage over prior art designs in that it reduces the cross-sectional area of the overall apparatus, reducing the amount of tissue damage caused during insertion of the surgical device. As shown in the embodiment of the surgical device deployment apparatus depicted in FIG. 64, the distal ends of the portal holder device abut the distal deployment surface (5851) of the obturator. Proximal movement of the obturator, while keeping the cannula and collar of the portal holder device relatively stationary, causes the distal deployment surface of the obturator to begin pushing the flexible fins (5803) rearward/proximally (away from the patient in a surgical setting) until the distal tips of the flexible fins are able to become dislodged from the cannula through the apertures (5836) and subsequently flex outwardly as a result of the natural outward biasing of the fins.

Referring now to FIGS. 65-70, shown are side views of the alternate embodiment of the portal holder device, and the embodiments of the obturator and cannula of the surgical device deployment apparatus as shown in FIGS. 63-64, in use during shoulder surgery. To be clear, embodiments of the surgical device deployment apparatus are shown in the context of an arthroscopic surgical procedure, but it is contemplated that the surgical device deployment apparatus may be utilized in other types of surgeries as well.

Figure 65:
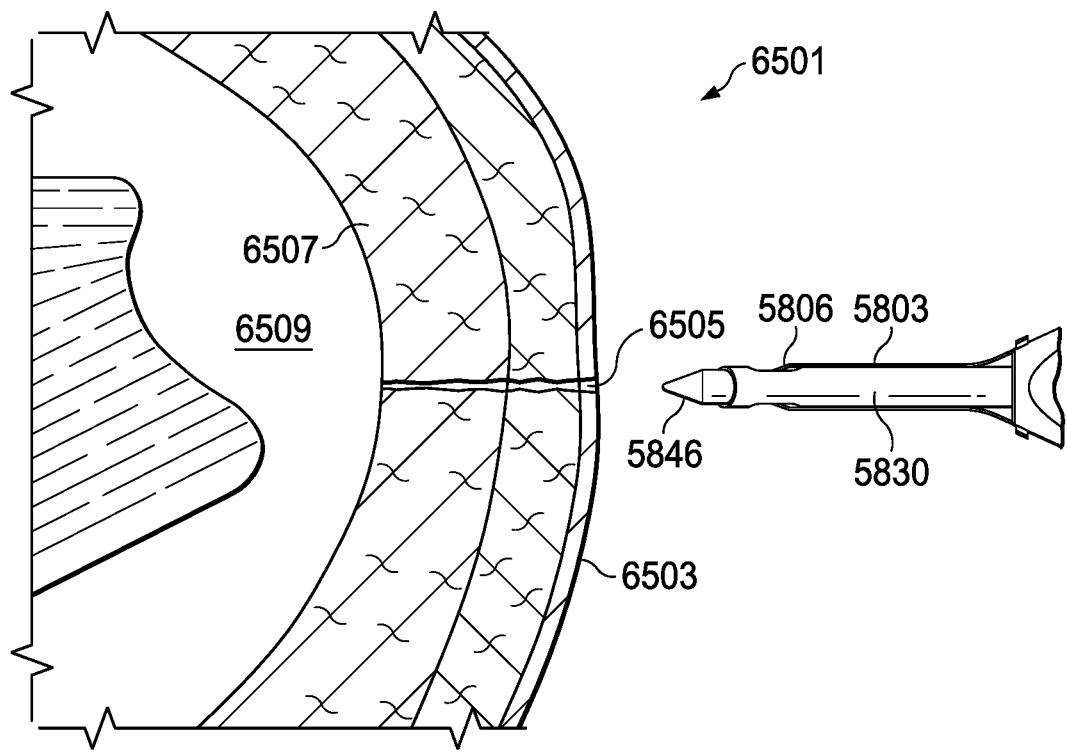
FIG. 65 depicts a side view of the alternate embodiment of the portal holder device, obturator, and cannula as shown in FIG. 64, in use during shoulder surgery, and more specifically, at a time just prior to insertion into a shoulder tissue structure.

Referring to FIG. 65, depicted is a partial side view of the alternate embodiment of the portal holder device, as well as the obturator and cannula of the surgical device deployment apparatus as shown in FIG. 64, in use during shoulder surgery, and more specifically, at a time just prior to insertion into a shoulder tissue structure. In FIG. 64, the fins (5803) of the portal holder device (5802) are mounted within the cannula (5830). In particular, the distal ends (5806) of the flexible fins protrude through the apertures of the cannula and into the reduced diameter portion (not shown) of the obturator. Still referring to FIG. 65, a cross-sectional view of a patient (6501) is shown adjacent to the distal end of the obturator (5846). Various layers of patient tissue (6507) are shown adjacent to a surgical site (6509). An incision point (6505) in the patient is shown, which forms one end of a passageway the obturator, cannula, and distal ends of the portal holder device's flexible fins must pass to access the surgical site.

Figure 66:
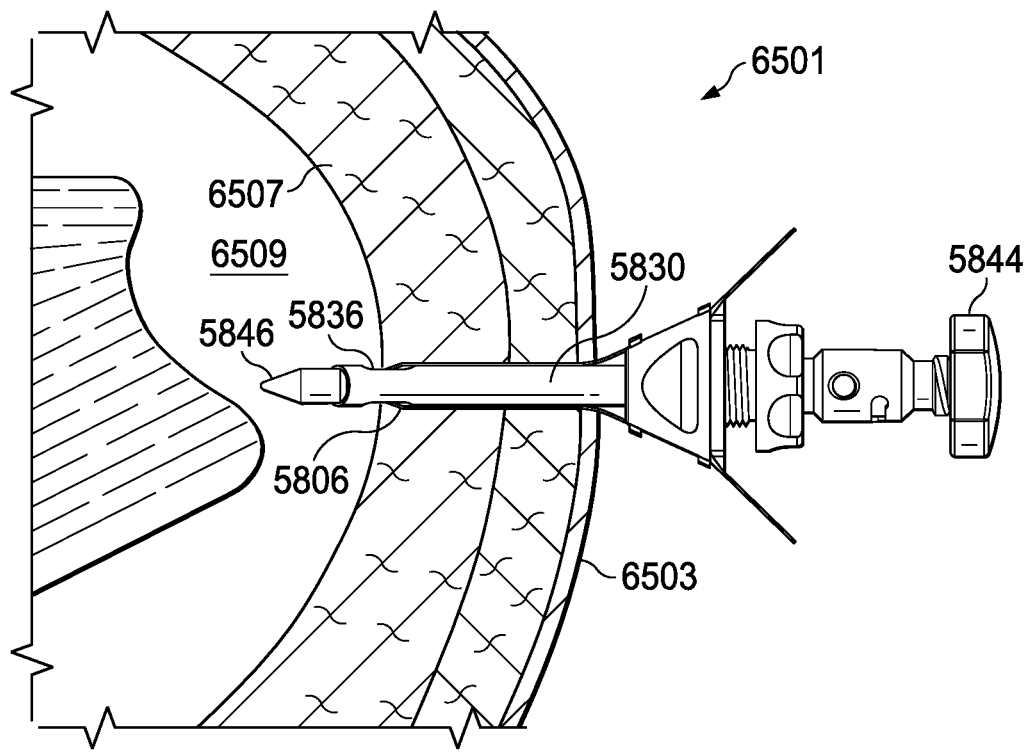
FIG. 66 depicts a side view of the alternate embodiment of the portal holder device, obturator, and cannula as shown in FIG. 65, in use during shoulder surgery, and more specifically, at a time just following insertion of the portal holder device, obturator, and cannula into a shoulder tissue structure.

FIG. 66 depicts a side view of the alternate embodiment of the portal holder device, and the embodiments of the obturator and cannula of the surgical device deployment apparatus as shown in FIGS. 63-64, in use during shoulder surgery, and more specifically, at a time just following insertion of the obturator, cannula, and distal ends of the portal holder device's flexible fins into a shoulder tissue structure. The portal holder device remains in its non-deployed state during such insertion.

Figure 67:
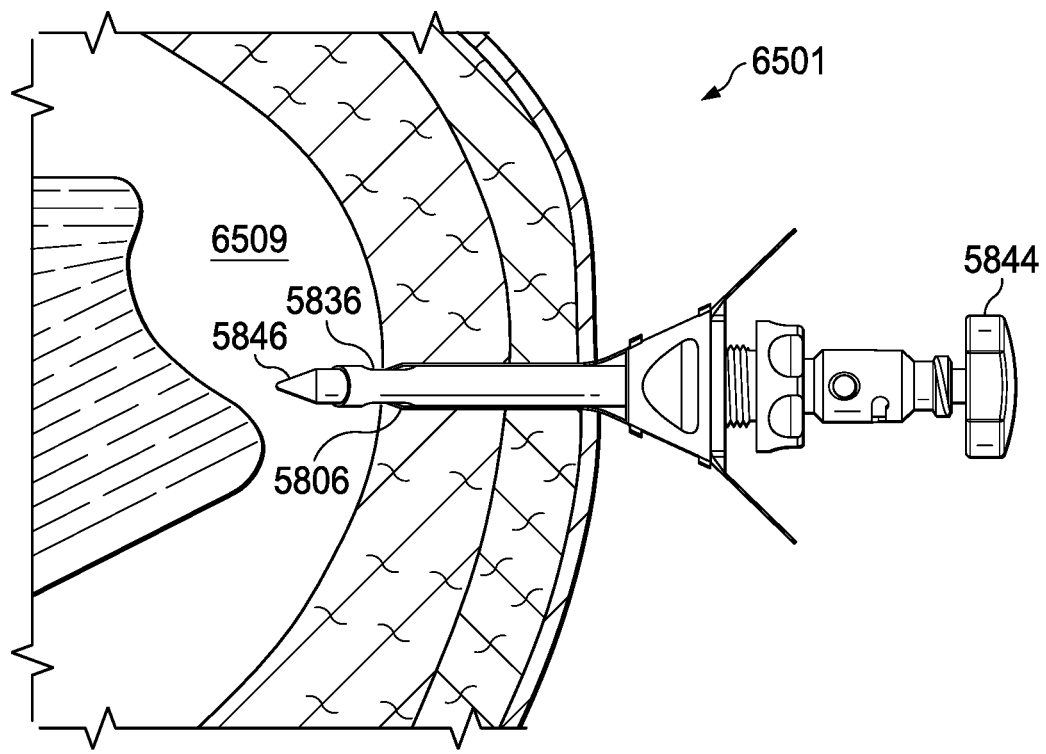
FIG. 67 depicts a side view of the alternate embodiment of the portal holder device, obturator, and cannula as shown in FIG. 65, in use during shoulder surgery, and more specifically, at a time just following insertion of the portal holder device, obturator, and cannula into a shoulder tissue structure, the obturator being moved proximally (towards surgeon) to allow for deployment of the shafts of flexible fins of the portal holder device.

FIG. 67 depicts a side view of the alternate embodiment of the portal holder device, and the embodiments of the obturator and cannula of the surgical device deployment apparatus as shown in FIGS. 63-64, in use during shoulder surgery, and more specifically, at a time following the rearward/proximal movement of the obturator away from the patient, while keeping the cannula and the collar of the portal holder device relatively stationary. As discussed above, in one embodiment this rearward movement of the obturator causes the deployment surface of the obturator to push the distal ends of the flexible fins of the portal device in a proximal direction. As the notches securing the flexible fins to the collar of the portal holder device allow the flexible fins to move in a rearward direction, such movement, coupled with the naturally outwardly biased flexible fins, ultimately causes the distal tips of the flexible fins to become dislodged from the cannula.

FIG. 68 depicts a side view of the alternate embodiment of the portal holder device, and the embodiments of the obturator and cannula of the surgical device deployment apparatus as shown in FIGS. 63-64, in use during shoulder surgery, and more specifically, at a time just following deployment of the flexible fins of the portal holder device. Once deployed, the fins (5803) of the portal holder device work to compress the patient's tissue, allowing for a shorter lumen length of the cannula. As discussed elsewhere herein, this is an advantage not seen in surgical devices of the prior art because this shortened lumen length allows a greater working angle for the surgeon's tools, which in turn provides for better access to the surgery site and reduces the need for physical manipulation of the portal holder during surgery. The advantage discussed above is most substantial when performing surgery on patients having a greater amount of fat tissue, as the flexible fins work to compress such tissues that would otherwise lead to a lessened range of movements during surgery.

Referring now to FIG. 69, depicting a side view of the alternate embodiment of the portal holder device, obturator, and cannula as shown in FIG. 65, in use during shoulder surgery, and more specifically, at a time following deployment of the flexible fins of the portal holder device as the obturator is moved proximally (away from patient and towards surgeon) while keeping the cannula and portal holder device relatively stationary. The obturator may be removed from the cannula to provide for the insertion of other surgical instruments into the cannula so as to access the surgical site. The obturator handle (5844), which may be shaped or textured to provide enhanced gripping properties, may be used by a surgeon to facilitate movement of the obturator.

Referring now to FIG. 70, depicting a side view of the alternate embodiment of the portal holder device, obturator, and cannula as shown in FIG. 65, in use during shoulder surgery, and more specifically, at a time following removal of obturator from the portal holder device and cannula. The obturator may be removed from the cannula to provide for the insertion of other surgical instruments into the cannula so as to access the surgical site. Likewise, the cannula may also be removed from the portal holder device. Once the cannula is removed from the portal holder device, the flexible fins of the portal holder device may provide a substantially impermeable seal, reducing fluid loss during surgery as previously described above.

Figure 71:
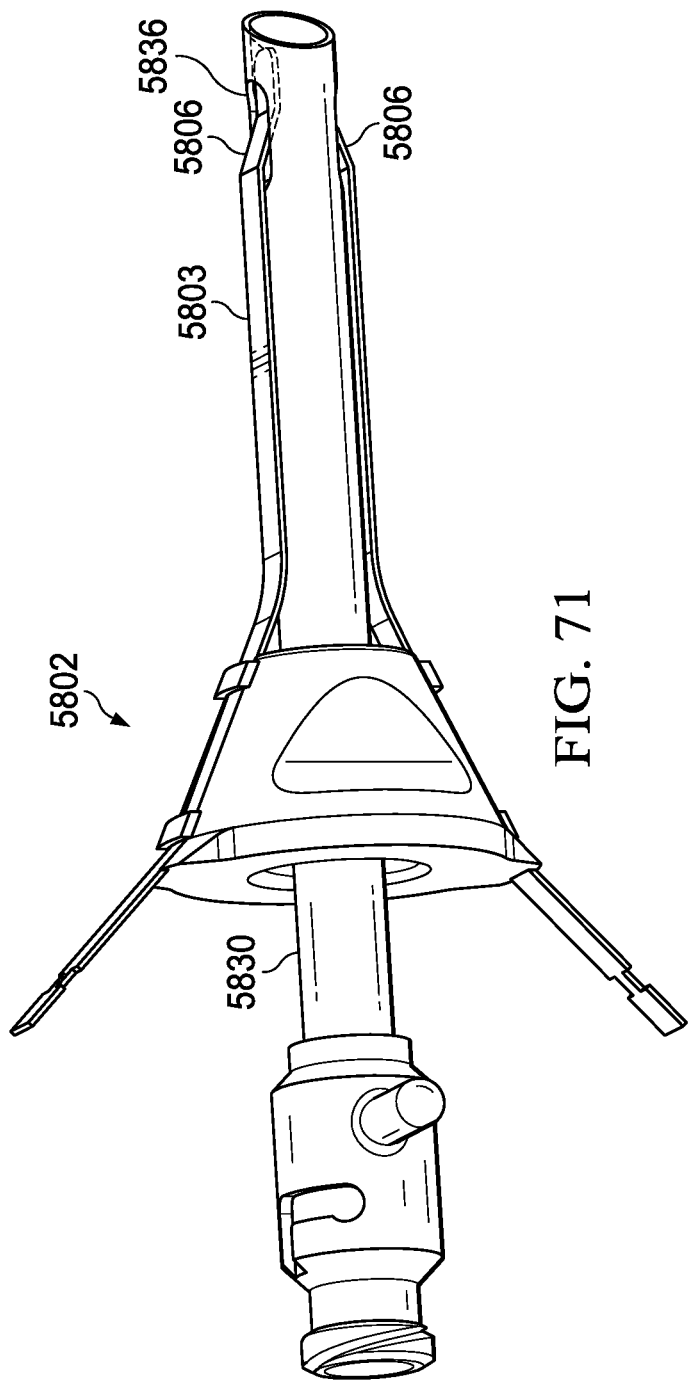
FIG. 71 depicts a perspective view of the portal holder device as shown in FIG. 63, mounted to a cannula as shown in FIG. 63 and ready for deployment.

Referring now to FIG. 71, depicting a perspective view of the portal holder device as shown in FIG. 63, mounted to a cannula as shown in FIG. 63 and ready for deployment. In alternate embodiments of the surgical device deployment apparatus, an obturator may be absent. In such alternate embodiments of the surgical device deployment apparatus, the distal tips (5806) of the flexible fins (5803) of the portal holder device may be insertable into the apertures (5836) of the cannula (5830), the distal tips being secured to the inner wall of the lumen of the cannula at a location distal to the cannula apertures. The flexible fins may be deployed by moving the portal holder device (including the fins) rearward until the distal tips (5806) become dislodged from the cannula apertures (5836). Alternatively, the flexible fins may be deployed by a user by moving the flexible fins rearward by grasping the proximal ends (5807) of the fins and pulling rearward.

Figure 72:
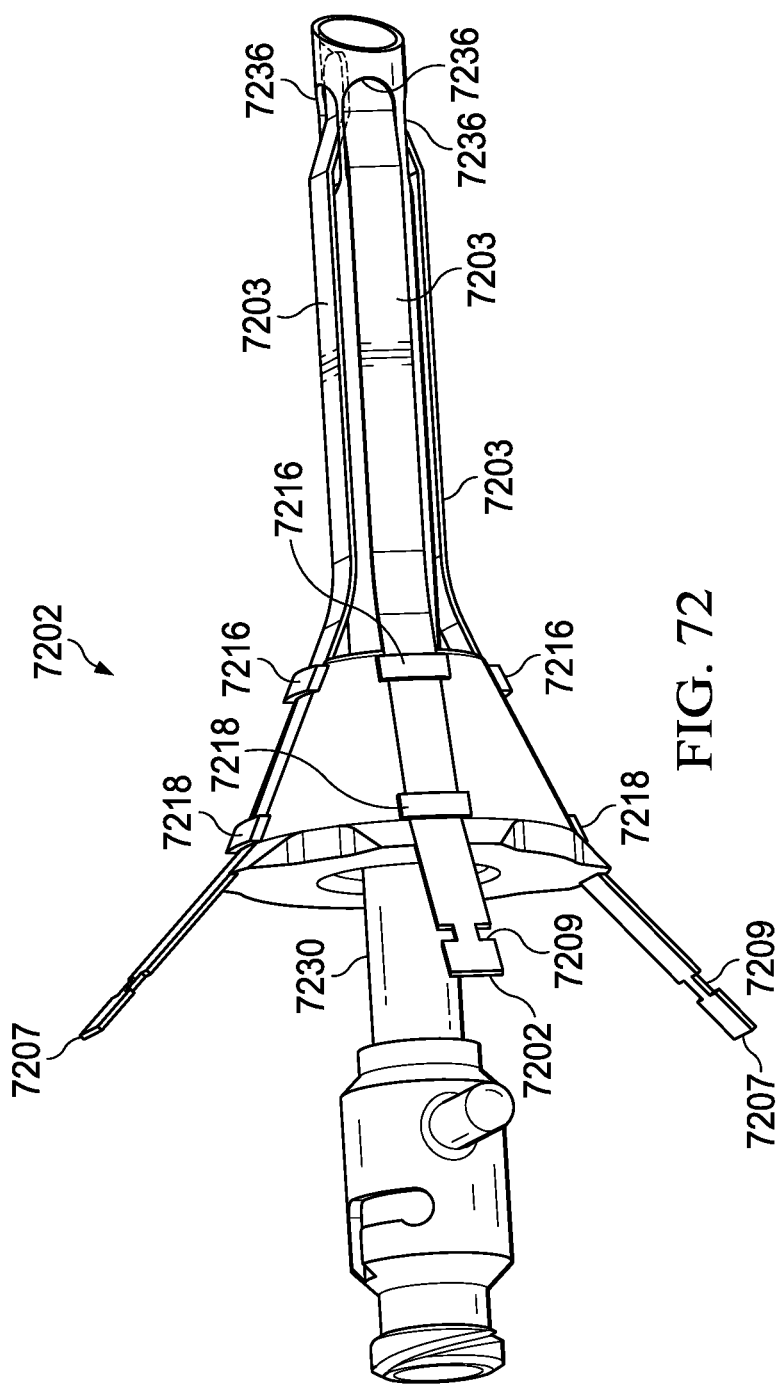
FIG. 72 depicts a perspective view of alternate embodiment of a portal holder device having three flexible fin shafts mounted to an alternate embodiment of a cannula and ready for deployment.

Referring now to FIG. 72, depicting a perspective view of alternate embodiment of a portal holder device having three flexible fins (7203) mounted to an alternate embodiment of a cannula and ready for deployment. In the alternate embodiment of the cannula shown in FIG. 72, a plurality of apertures are formed on the distal end of the cannula such that a correspondingly sized distal tip of a portal holder device flexible fin may be inserted into each cannula aperture. One advantage realized by utilizing multiple flexible fins is increased tissue compression during surgery, thus providing for greater flexibility in manipulating instruments at the surgical site.

Figure 73:
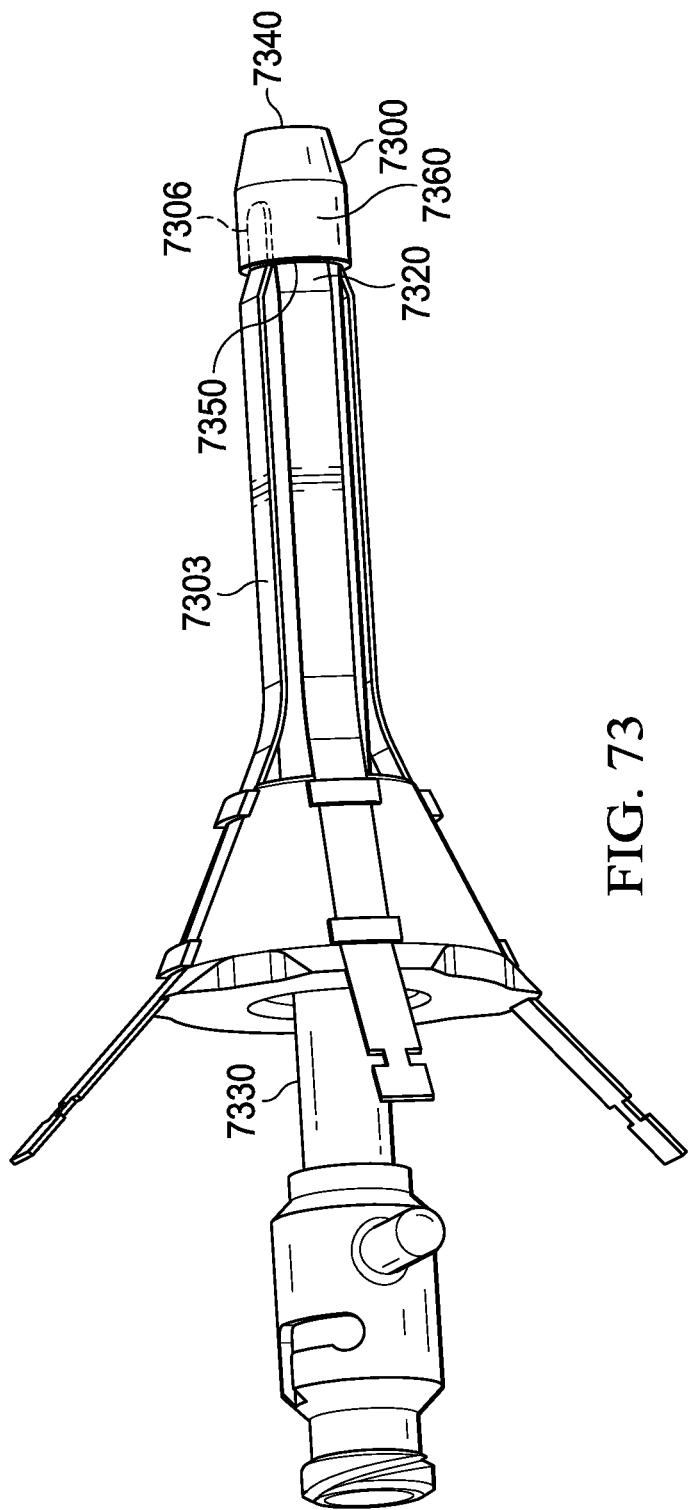
FIG. 73 depicts a perspective view of an embodiment of a removable nose "ring" mounted to the distal end of an embodiment of an arthroscopic cannula device, the distal ends of shafts or other biasing devices of an embodiment portal holder device may be inserted and secured under a hood of the nose ring prior to deployment of such shafts.

Referring now to FIG. 73, depicted is a perspective view of an embodiment of a removable nose "ring" or "hood" mounted to the distal end of an embodiment of an arthroscopic cannula device, the distal ends of shafts or other biasing devices of an embodiment portal holder device may be inserted and secured under a hood (space between outer wall of ring and inner wall of ring, or space between outer wall of ring and outer surface of cannula shaft) of the nose ring prior to deployment of such shafts. FIGS. 63-72 discussed above contemplate embodiments of a cannula having cannula apertures for receiving the distal tips of a portal holder flexible fin shafts to prevent outer movement of such flexible fins prior to the intended deployment within the patient during surgery. However, it is contemplated that it may desirable in some situations to utilize an unmodified surgical cannulas, in other words, not having the cannula apertures, but rather attaching an attachable and removable nose ring (7300) shown in FIG. 73. The nose ring has a body having a hollow lumen having an inner wall (7320) and an outer wall (7360). In one embodiment as shown in FIG. 73, the outer wall (7360) comprises a top portion of the nose ring body that extends past the upper end of the inner wall, and the inner wall (7320) comprises a bottom portion of the nose ring body that extends below a bottom end of the outer wall, a top end of the inner wall nests within a lower and intermediate portion of the outer wall. In one embodiment of the nose ring, the top end (7340) of the outer wall tapers inwardly towards the lumen as shown in FIG. 73, while the bottom end of the outer wall has an inner diameter that is greater than the outer diameter of the outer wall, creating a space between the inner and outer walls. This space between the outer wall and the inner wall of the nose ring, sometimes referred to herein as a "hood," is where one or more distal tips of biasing device shafts (of a portal holder or cannula device) may be inserted and secured within prior to deployment of such biasing device shafts. The lumen that is formed through the center of the nose ring is sized to accept the tip and distal shaft of a commonly used arthroscopic surgical cannula (or any other type of cannula or surgical instrument), allowing the tip to penetrate and slide through the nose ring lumen. It should be noted that while the nose ring or "shaft retention cap" is depicted as being mounted on most distal end of a cannula shaft (7303), the nose ring can alternatively be mounted at a more proximal location on the cannula shaft, depending on such factors as the length of the shafts of the portal holder device. In such embodiments, a distal portion of the cannula shaft may protrude from the distal end (7340) of the nose ring. The nose ring in some embodiments may have an internal lumen (7332) sized to create a tight fit with the outer wall of the cannula shaft such that the nose ring when mounted may stay substantially secured to such cannula. In other embodiments, the nose ring may be fastened to the shaft of the cannula via one or more fasteners. In one embodiment, an adhesive may be used to attach the outer wall of the nose ring body to the inner wall of the nose ring body (in one embodiment, constructed of stainless steel). In another embodiment, threads may be formed on the internal wall of the nose ring, and other corresponding threads formed on the shaft of the cannula device, such that the nose ring may be threadedly fastened to the cannula shaft. It should also be noted that while the embodiment of the nose ring shown in FIG. 73 is depicted as working to secure the distal tips of three flexible shafts of a portal holder device, the nose ring may be equally utilized to secure a greater or lesser number of tips of flexible shafts of portal holder devices, surgical cannula devices, and other surgical devices having shafts or fins that need to be secured prior to deployment in alternate embodiments of the nose ring.

It is contemplated that the inner diameter of the inner wall portion of the nose ring (7300) should be sized such that a commonly used surgical cannula, when the cannula is inserted into the nose ring, tightly fits around the end of the cannula. In one embodiment, the outer wall of the nose ring is constructed of a flexible polymer having an upper end with an inner diameter sized smaller than the outer diameter of the surgical cannula on which it is intended to be mounted. The polymer outer wall of the nose ring however may stretch to allow passage of the surgical cannula and also provide further gripping on the cannula body to better secure the nose ring onto the cannula. The texture of the polymer may also aid in preventing slippage when the nose ring is attached to the distal end of the surgical cannula. In one embodiment, the nose ring may be comprised of two hollow bodies mated to one another. A first hollow body (7320) may be substantially cylindrical in shape and in some embodiments, may be constructed of a metal such as aluminum or stainless steel. In such an embodiment, the first hollow body may have an inner wall formed a lumen, said inner wall having a diameter only slightly larger than the outer diameter of a cannula shaft on which it is to be mounted. To mount a nose ring having such a first hollow body onto a cannula, a user must apply sufficient force to slide the nose ring onto the cannula shaft. The nose ring may then be positioned at an ideal position on the cannula shaft, taking into account the length of the shaft or fins that are intended to be mounted on the cannula. The nose ring's first hollow body will have an inner wall diameter sized such that when the nose ring is mounted onto the cannula, the nose ring can slowly slide along the length cannula shaft with the application of sufficient force available to most typical users such as surgeons, physician's assistants, nurses, and other operating personnel, but not so loose as to allow the nose ring to slide when the distal tips of shaft or fins are placed within the hood. In other embodiments, the first hollow body may have an upper portion that has a decreased diameter as compared to a diameter of a lower portion of the first hollow body, the inner wall of the first hollow body having an inner wall diameter that gradually tapers from the lower portion to the upper portion. In this manner, the inner wall of the upper portion of the first hollow body may serve to arrest any sliding movement when the nose ring is mounted to a cannula shaft. A second hollow body of the nose ring, which in one embodiment may be constructed of a flexible polymer, has a lumen formed by an inner wall. The diameter of a lower portion of the inner wall of the second hollow body may be configured to be larger than an outer diameter of a lower portion of the first hollow body such that when the first hollow body mates with second hollow body, there exists the aforementioned hood or space between the overlapping first hollow body and second hollow body. It is in this space between the first and second hollow bodies that the distal tips or shafts or fins may be secured as illustrated in FIG. 73. In some embodiments of the nose ring, the first and second hollow bodies may be integrally attached to one another. In other embodiments of the nose ring, the first and second hollow bodies may be removable and may be attachable by various means such as, for example, being threadedly attached to one another.

Figure 74:
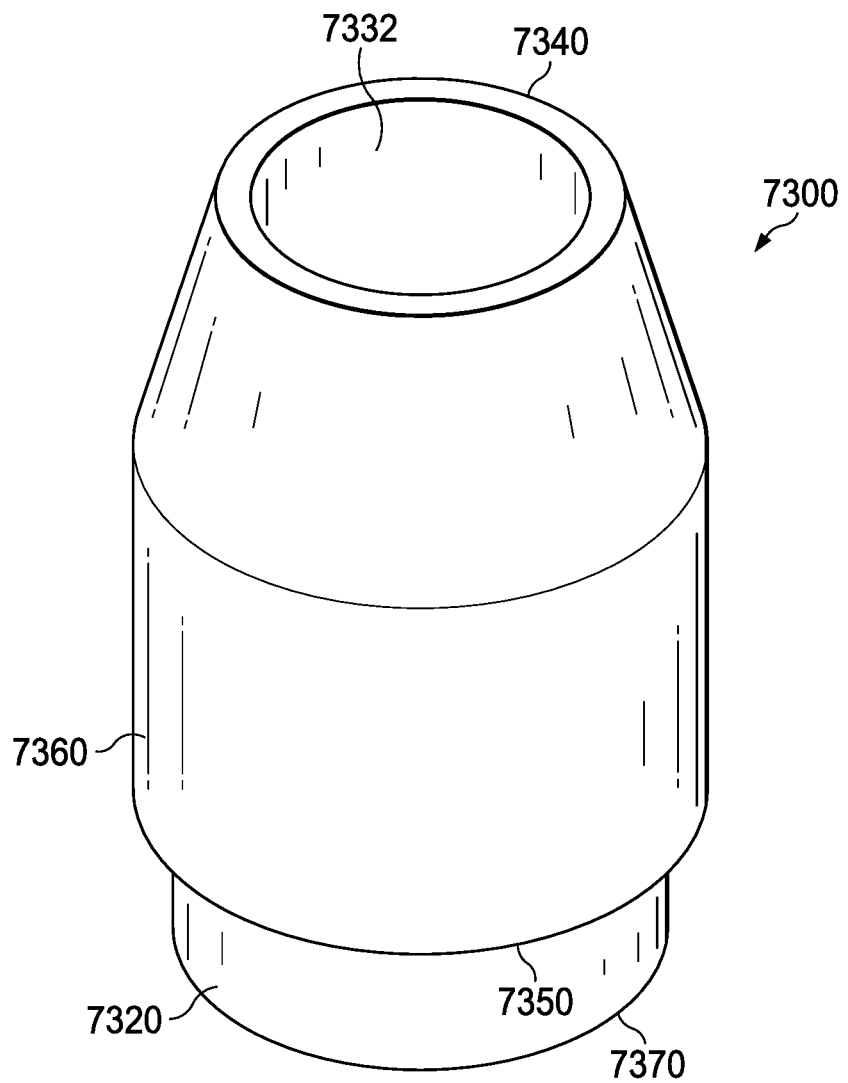
FIG. 74 depicts an upper perspective view of the embodiment of a removable nose "ring" as depicted in FIG. 73.

Referring now to FIG. 74, depicting an upper perspective view of the embodiment of a removable nose "ring" as depicted in FIG. 73. In the embodiment shown at FIG. 74, the nose ring (7300) comprises a body having a central lumen (7332) having a diameter sized to allow for the passage of the distal tip and shaft of a commonly used hollow arthroscopic surgical cannula (and other types of hollow surgical cannulas). In one embodiment, the nose ring comprises an outer wall (7360) and an inner wall (7320). The inner wall is sized such that a space is formed between the surgical cannula (when the nose ring is mounted onto such surgical cannula) and the inner wall, the space providing an area in which the biasing device shafts of a cannula device or the flexible fins of a portal holder device, as discussed above, may be inserted prior to deployment. In one embodiment, one or more apertures may be formed through one or more walls of the nose ring body to provide access for the attachment of a suture.

Figure 75:
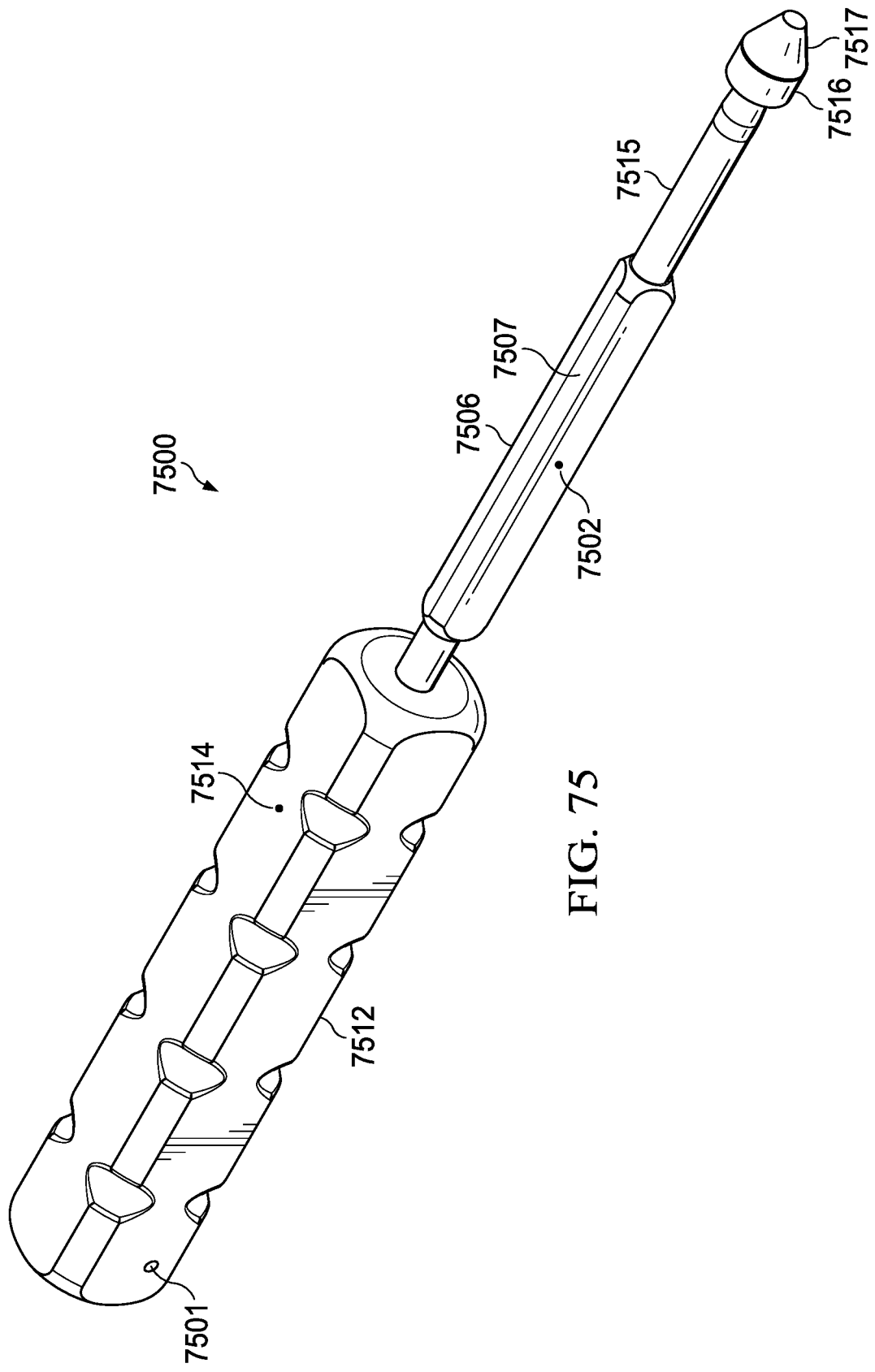
FIG. 75 depicts a perspective view of an embodiment of a cannulated obturator assembly having a selectable length shaft, onto which a portal holder device or other surgical device is configured to be mounted.
Figure 76:
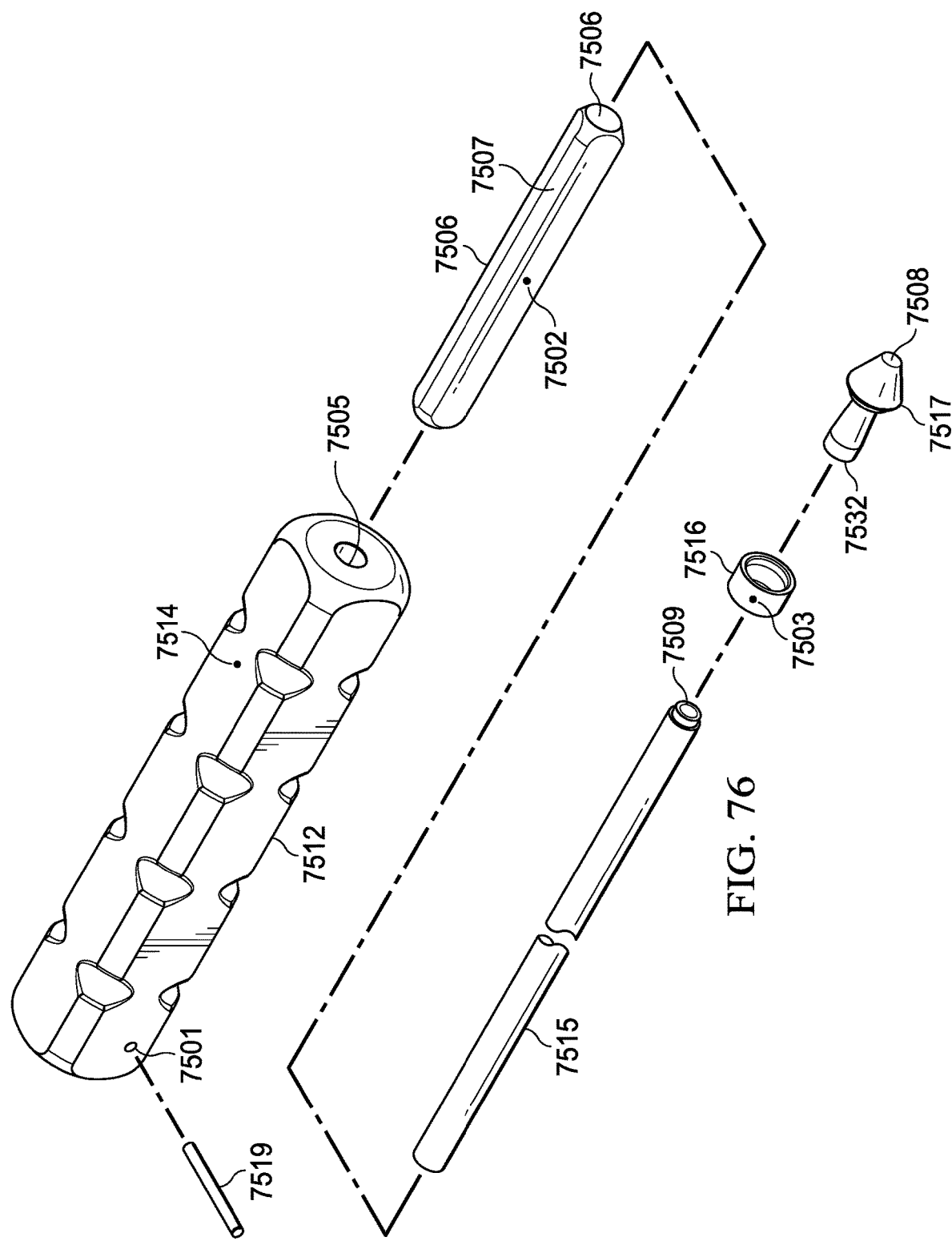
FIG. 76 depicts an exploded view of the embodiment of a cannulated obturator assembly depicted in FIG. 75.

Referring now to FIG. 75 and FIG. 76, depicting a perspective view and an exploded view, respectively, of an alternate embodiment of a cannulated obturator assembly (7500) having a selectable length shaft, onto which a portal holder device (not shown) or other hollow surgical device (for example, the surgical cannula devices having retractable fins discussed herein) is configured to be mounted. In this alternate embodiment, there is provided a selectable length obturator shaft (7515). One or more holes (7505) are formed through the obturator handle (7512) and through to the handle lumen (see FIG. 80 at 7513) which is sized and shaped to receive the obturator shaft (7515), which is configured to slide proximally and distally in such handle lumen (7513) when not secured. A pin (see FIG. 76 at 7519) may be used to slide into the hole (7501) and when the obturator shaft is properly aligned in the handle lumen, into a correspondingly sized hole (not shown) formed onto the obturator shaft, thus securing the obturator shaft at a set working length. Other holes (7514) are shown on the obturator handle, which may also be used to secure the obturator shaft at other working lengths using the pin. In other embodiments now depicted herein, the obturator shaft may be comprised of a telescoping shaft to provide for variable lengths, and may be spring-loaded in some embodiments. For example, in one embodiment, a coil spring may be mounted in the proximal portion of the obturator handle lumen (7513) such that a proximal portion of the obturator shaft may compress it in one mode of operation, but such spring may apply an outwardly directed spring force to telescope the obturator shaft in a distal direction in another mode of operation. In one embodiment, the obturator shaft may comprise a collapsible plurality of connected sections having varying diameters similar to a leg of a collapsible camera tripod, allowing the shaft to extend its length, while also allowing for the shortening of the shaft based on the needs of the surgeon. The components of the obturator assembly may be constructed of various metals, alloys, polymers, and/or a combination of such materials. For example, in one embodiment of the obturator assembly, the handle (7512) may be constructed of 6061-T6 aluminum, and the obturator shaft (7515), obturator tip (7517), tip sleeve (7516), support sleeve (7506), and pin (7519) may be constructed of 17-4 SS H900 stainless steel.

In one embodiment of the obturator assembly (7500), a support sleeve shaft (7506) may have a plurality of raised lobe members (7507) extending from the support sleeve shaft, providing rotational stability for a mounted portal holder assembly or other cannula device, making it less likely that the mounted portal holder or cannula device will rotate about the obturator shaft. For example, the plurality of raised lobes (7507) provides for additional structural support and stability when a distal fluid sleeve (see FIG. 97 at 8952) or similar structure is mounted on the support sleeve prior to deployment of the fins of a portal holder device. In one embodiment, a distally located obturator tip (7517) with a distal opening (7508) is attached to the distal end of the obturator shaft. An obturator tip sleeve (7516) is configured to be mounted to the obturator tip, the tip sleeve (7516) has internal geometry providing for a hood into which the insertion of the distal tips of portal holder flexible fins or distal shaft tips of cannula devices. All of the obturator handle, obturator shaft, support sleeve, and obturator tip and tip sleeve are cannulated (hollow) and have a lumen extending through such structures, with openings formed on opposite ends of such structures, to provide for the passage of surgical instruments and other objects used during surgery (the lumen of the support sleeve allows the cannulated obturator shaft to extend through said support sleeve).

Figure 77:
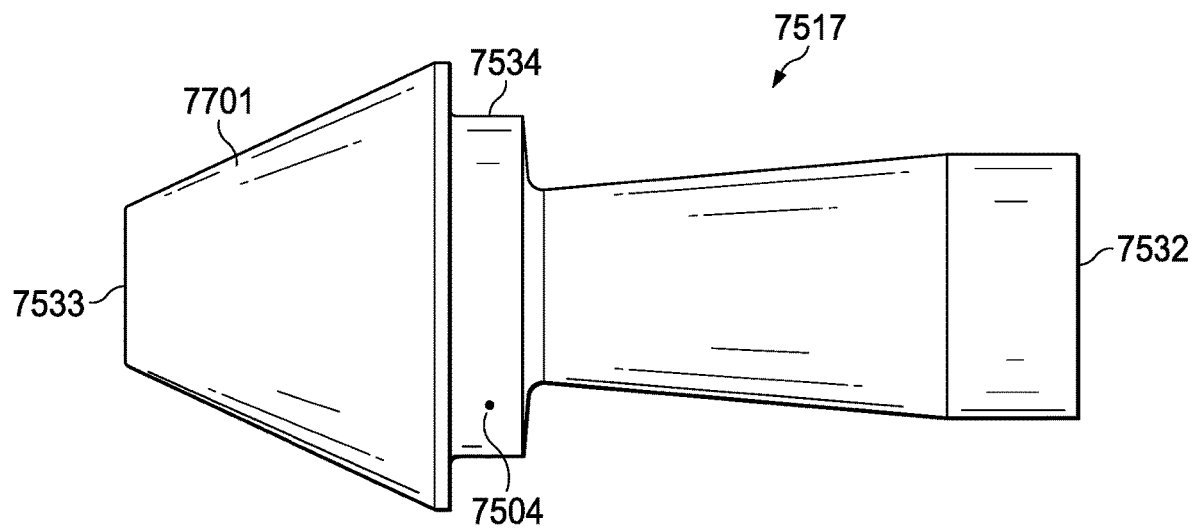
FIG. 77 depicts a side view of the cannulated obturator tip of the embodiment of a cannulated obturator assembly depicted in FIG. 76.
Figure 78:
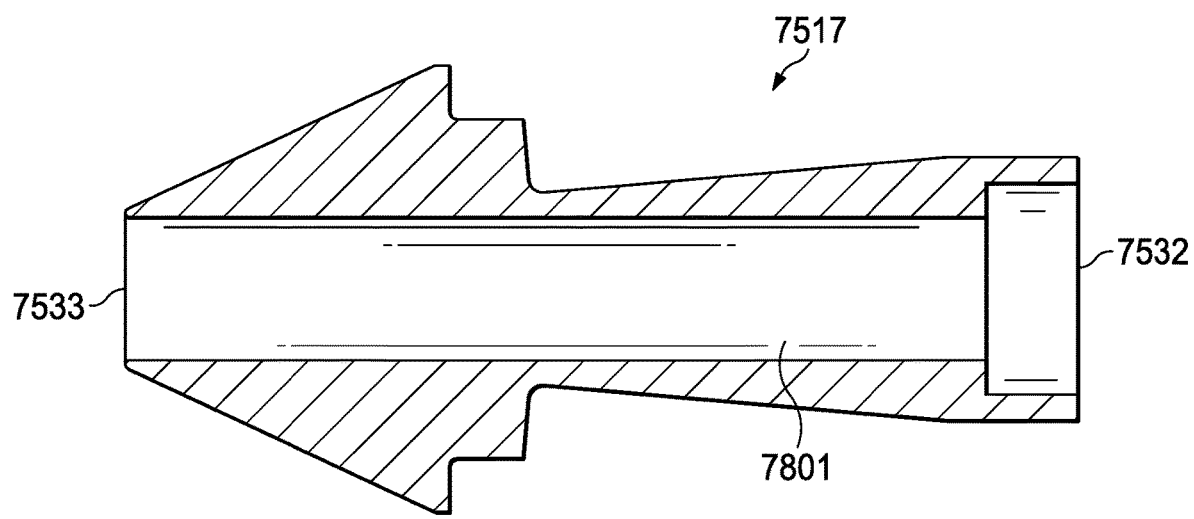
FIG. 78 depicts a cross-sectional view of the cannulated obturator tip depicted in FIG. 77.

Referring now to FIG. 77 and FIG. 78, depicting a side view and a cross-sectional view, respectively, of the cannulated obturator tip (7517) of the embodiment of a cannulated obturator assembly having a selectable length shaft as appearing in FIG. 75 and FIG. 76. A lumen (7801) of the cannulated obturator tip (7517), which provides for the passage of surgical instruments and other objects used during surgery, extends from the proximal end (7532) of the tip to the distal end of the tip (7533). The diameter of the lumen (7801) of the tip may be constructed to have various diameters to accommodate the size of the surgical instruments intended to be passed through said lumen. A distal opening (7508) of the tip is depicted in FIG. 76. A second opening to the lumen (7801) is also present at the opposite proximal end of such lumen. The diameters of the lumen openings of the tip may be constructed to have various diameters to accommodate the size of the surgical instruments intended to be passed through said openings. A shelf (7534) having a smaller outer diameter as compared to the proximal portion of the tapered distal end portion (7701) of the tip, is formed on the obturator tip in one embodiment, allowing for the mounting of a tip sleeve as illustrated at FIG. 79. The tip sleeve, which in one embodiment may be attached to the obturator tip via a pin fastener inserted into a hole (7504), serves as a hood under which the distal tips of flexible fins may be inserted and secured prior to fin deployment in a manner as depicted in FIG. 56, FIG. 58, and FIG. 73.

Referring now to FIG. 79, depicting a cross-sectional view of the tip sleeve (7516) of the embodiment of a cannulated obturator assembly having a selectable length shaft as appearing in FIG. 75 and FIG. 76. A distal portion (7542) of the tip sleeve is sized and shaped to mount onto the shelf of the obturator tip. The tip sleeve serves as a hood under which the distal tips of outwardly-biased flexible shafts may be inserted and secured prior to deployment in a manner as depicted in FIG. 56, FIG. 58, and FIG. 73. While the tip sleeve and obturator tip of the embodiment of the obturator assembly depicted herein are shown as separate structures configured to attach to one another, it is contemplated that alternate embodiments of the obturator tip will include an integral hood structure for securing shaft tips under prior to deployment.

Referring now to FIGS. 75-80, disclosed herein in one embodiment is a surgical device deployment tool, the tool comprising: a cannulated handle member having a proximal end and a distal end; a collapsible cannulated elongate shaft attached to said handle member, said collapsible elongate shaft extending distally and terminating at a cannulated shaft head, said shaft head having a hood such that a gap exists between an inner surface of said shaft head and an outer surface of said shaft head. In one embodiment, the surgical device deployment tool further comprises an elongate hollow support sleeve configured to be mounted around a portion of a length of the shaft of the tool, the support sleeve in one embodiment having a plurality of raised lobe members extending outwardly from the support sleeve. In another embodiment, a shaft head sleeve having a substantially cylindrical shape is attachable to a proximal end of the shaft head and forms the hood in which the distal tips of a surgical device may be secured prior to deployment of the surgical device.

Referring now to FIG. 80, depicting a cross-sectional view of the cannulated obturator handle of the embodiment of a cannulated obturator assembly having a selectable length shaft as appearing in FIG. 75 and FIG. 76. A central lumen (7513) of the cannulated obturator handle (7512) is sized and shaped to receive a correspondingly sized and shaped cannulated obturator shaft (7515). In one embodiment of the obturator assembly, the obturator shaft will be attached to a distal end of the handle and not be inserted into the lumen (7513). An opening (7505) is formed on the distal end of the obturator handle, providing access to the handle lumen (7513). In one embodiment, a hole (7501) is formed through the handle, allowing a pin (7519) to slide through such hole and into the lumen (7513) to mate with a correspondingly sized hole formed in a proximal portion of the obturator shaft to secure such shaft to the handle. In alternate embodiments, such holes may be positioned at various locations on the handle and on the obturator shaft. In some embodiments, the obturator shaft will be attached to the handle by other means such as being threadedly fastened to the handle, fastened via adhesive, or be formed as an integral extension of the handle during construction. In one embodiment, the proximal end of the handle may include an opening to the lumen (7513) such that access to the lumen may be provided on such proximal end of the handle. In this manner, surgical instruments may be inserted into the proximal end of the handle, pass through the lumen of the handle, pass through the lumen of the hollow obturator shaft, and out the distal opening (7508) of the hollow cannulated tip (7517). In other embodiments, the proximal end of the obturator shaft may extend to the proximal end of the handle such that instruments may be inserted directly into the lumen of the obturator shaft.

Figure 81:
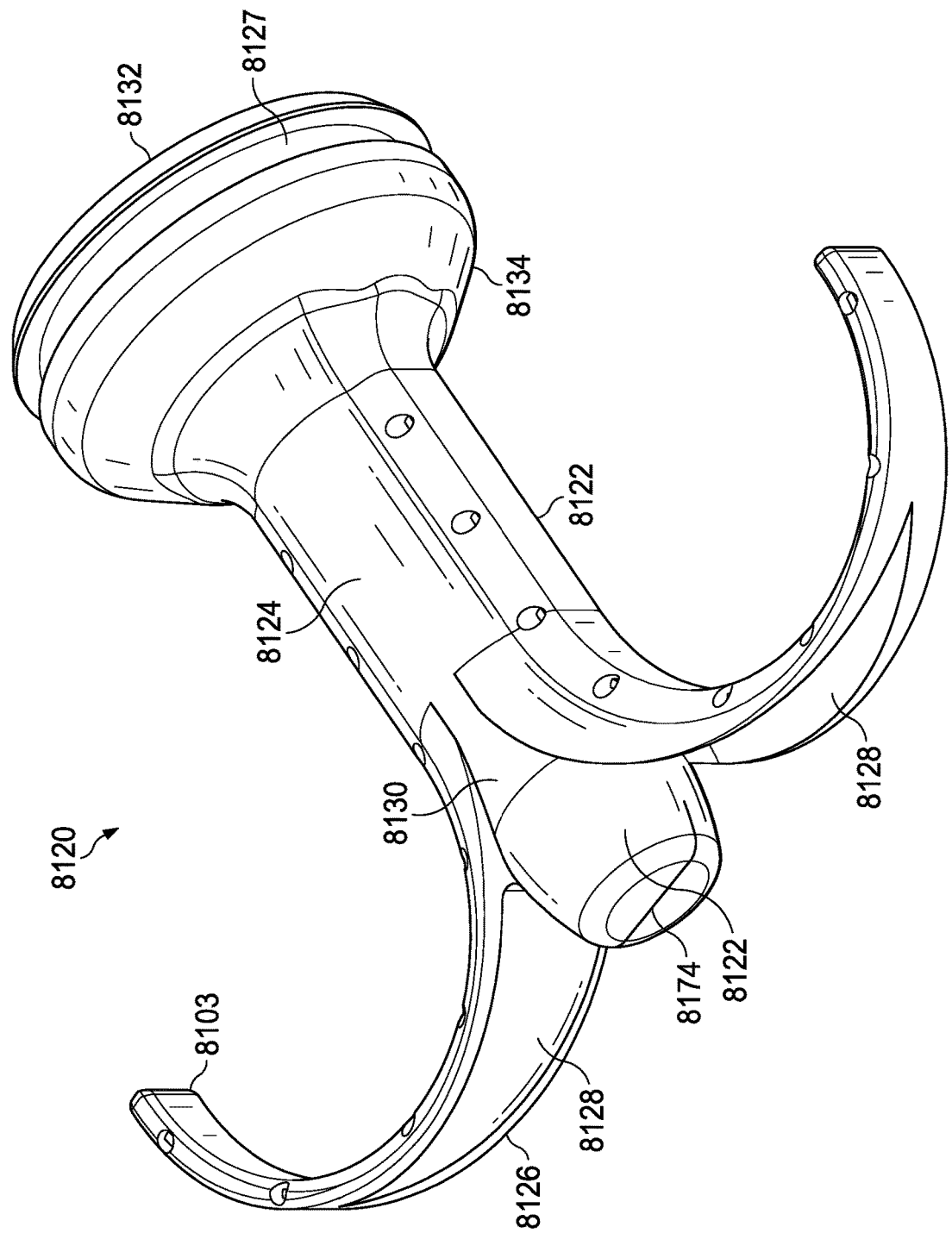
FIG. 81 depicts a perspective view of an alternate embodiment of a surgical cannula device having outwardly-biased elongated shafts embedded within flexible fins, and includes a distally projecting fluid gate.
Figure 87:
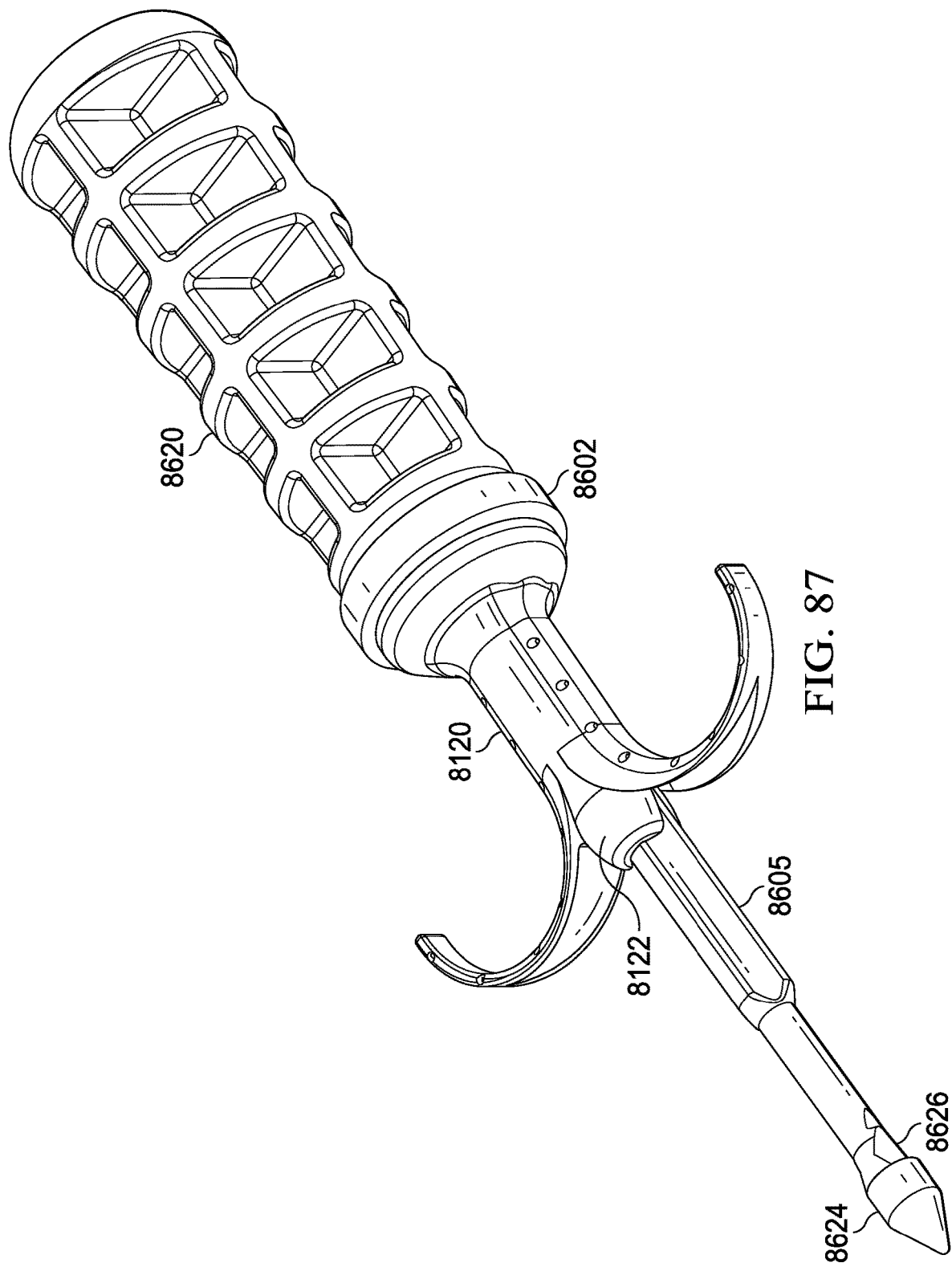
FIG. 87 depicts a perspective view of the alternate embodiment of a surgical cannula device shown in FIG. 86, mounted on an obturator assembly, the fins of the cannula device flexed in an outward position.

Referring now to FIG. 81, depicting a perspective view of an alternate embodiment of the surgical cannula device (8120) having outwardly-biased elongated shafts embedded within flexible fins. The cannula device comprises a body (8122) having an internal central lumen (8124) formed by inner walls, which are split to form branched flexible fins (8126). Elongate shafts (8128), naturally biased in an outward direction and in one embodiment constructed of shape memory alloys such as Nitinol, are embedded within cavities formed within such flexible fins (not shown in FIG. 81, but see FIGS. 30-32, showing the elongate shafts embedded within cavities of the flexible fins of another embodiment of the surgical cannula device, and see FIG. 83 at 8128). At a location adjacent to where the inner walls of the body of the cannula device are split to form the branches of the flexible fins, an internal fluid gate (8122) having a distally located slit opening (8174) protrudes in a distal direction, said internal fluid gate having walls (8130) joined to the body of the cannula device. The internal fluid gate is roughly cylindrical in shape, although in some embodiments, the distal portion of the internal fluid gate may be tapered as shown in FIG. 81 such that the diameter of the distal end of the internal fluid gate (8122) is smaller than the proximal end of the fluid gate. Openings are formed on both ends of the internal fluid gate—the slit opening located on the distal end of the internal fluid gate, and a second opening on the proximal end of the fluid gate, which leads to the lumen of the cannula device. In some embodiments, including the embodiment shown in FIG. 81, the internal fluid gate is a distally projecting extension of the inner walls and outer walls of the body of the cannula device (extending beyond the point or section at which the branched flexible fins split from the body of the cannula device), the internal fluid gate having inner and outer walls of reduced diameter as compared to the walls of the more proximally located portions of the body of the cannula device. In one embodiment the distal end of the internal fluid gate may be flat or rounded, the distal opening being a slit opening that is flexible to allow for the passage of surgical instruments, scopes, and other items that are deployed during surgery, yet able to provide for fluid retention. The flexible slit opening is flexible enough to conform around the shape of the instruments as depicted in FIG. 87, forming a seal around the instruments to aid in fluid retention when positioned within or adjacent to the surgical site. The other walls (8130) are sealed to the body of the cannula device such that of the internal fluid gate such that any fluid or instrument entering or exiting the distal end of the cannula device must pass through the slit opening (8174). The internal fluid gate (8122) in one embodiment protrudes distally away from the locations in which the walls of the body split to form the fin branches. Such distally projecting protrusion of the internal fluid gate provides an advantage, as compared to having a fluid gate opening positioned more proximally, in that the protruded nature of the internal fluid gate positions such gate closer to the surgical site, thereby optimizing its ability to retain fluid. The internal fluid gate is often referred to as being "internal" in the sense that is some embodiments, the internal fluid gate is positioned inside the patient during some parts of a surgical operation. The length by which the internal fluid gate (8122) may protrude distally away from the position at which the branches of the fins split away from the body may vary based on, among other things, the type of surgery in which the cannula device will be implemented, the types of instruments intended to be passed through the cannula device, and based on the anatomy of the patient. In one embodiment, the body of the cannula device, and the fins of the cannula device, may be constructed of a polymer such as a flexible thermoplastic. In one embodiment, the body of the cannula device, and the fins of the cannula device, may be constructed of urethane. As noted elsewhere herein, the elongate shafts may be constructed of a shape memory alloy such as Nitinol.

Still referring now to FIG. 81, disclosed herein in one embodiment is a cannula (8120) for surgical procedures, the cannula comprising: a body member (8122) having an inner wall forming a lumen (see FIG. 83 at 8124) along at least a proximal portion of a length of said body member to form a port for a surgical tool, said inner wall and an outer wall of said body member being split to form branches at a distal end of said lumen so as to form a plurality of flexible fins (8126), wherein a cavity is disposed within each of said plurality of flexible fins (see FIGS. 30-32 showing how cavities are formed in fins), wherein an elongate shaft is embedded within each of said cavities (see FIGS. 30-32 showing elongate shafts 8128 are each embedded within a cavity in the fins), and wherein a hollow internal fluid gate (8122) having a second lumen is formed between said plurality of flexible fins at a junction of the proximal ends of said plurality of flexible fins adjacent to where said body member is split, said internal fluid gate having a distally extended protrusion terminating with a distal flexible slit opening. In one embodiment, the internal fluid gate is substantially cylindrical in shape and has a lower portion (8130) that is sealed to the body of the cannula device and has a proximal opening leading to the lumen (8124) of the cannula device.

Figure 82:
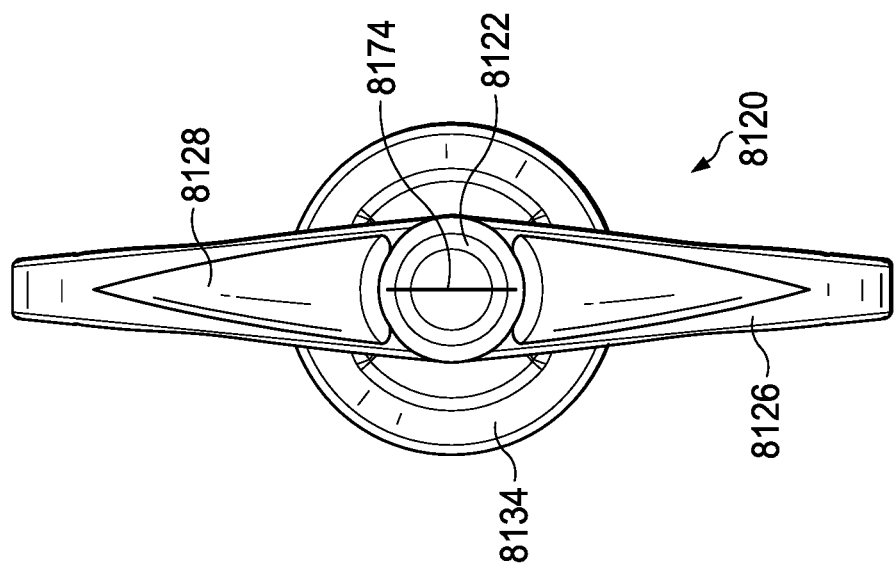
FIG. 82 depicts a top view of the alternate embodiment of a surgical cannula device shown in FIG. 81.

Referring now to FIG. 82, depicting a top view of the alternate embodiment of the cannula device having outwardly-biased elongated shafts embedded within flexible fins and having an internal fluid gate as depicted in FIG. 81. It should be noted that the reference number '8128' is used to indicate that the elongated shafts are embedded within the fins (8126), not to depict the shape of an embodiment of such fins (see FIGS. 84-85, showing elongated shafts).

Figure 83:
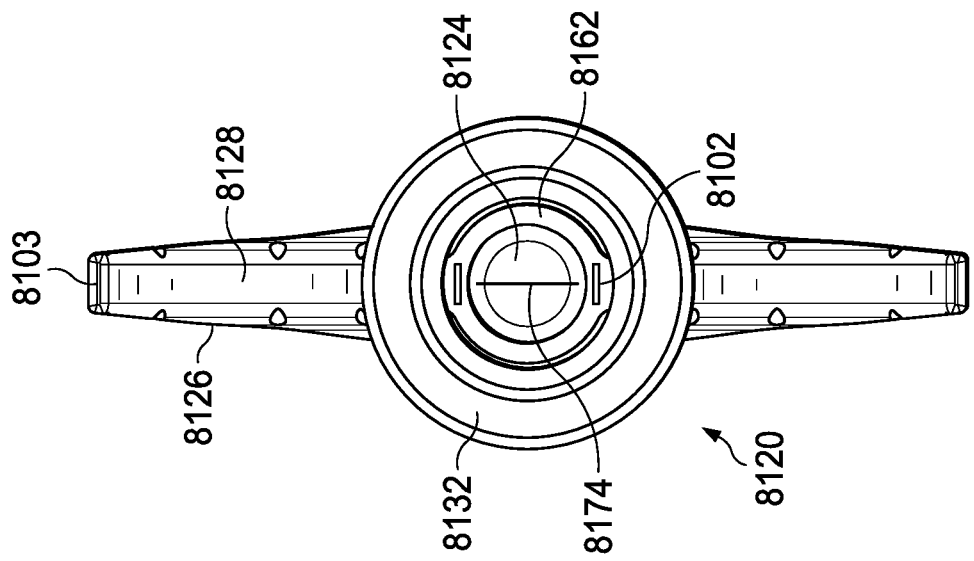
FIG. 83 depicts a bottom view of the alternate embodiment of a surgical cannula device shown in FIG. 81.

Referring now to FIG. 83, depicting a bottom view of the alternate embodiment of the cannula device having outwardly-biased elongated shafts embedded within flexible fins as and having an internal fluid gate as depicted in FIG. 81. The embodiment of the outwardly-biased elongate shafts of the cannula device (see FIG. 96), configured to be embedded within the flexible fins, are joined at a proximal end by a shaft collar (8162) configured to be mounted at a proximal end of the cannula device as depicted in FIGS. 84-85.

Figure 85:
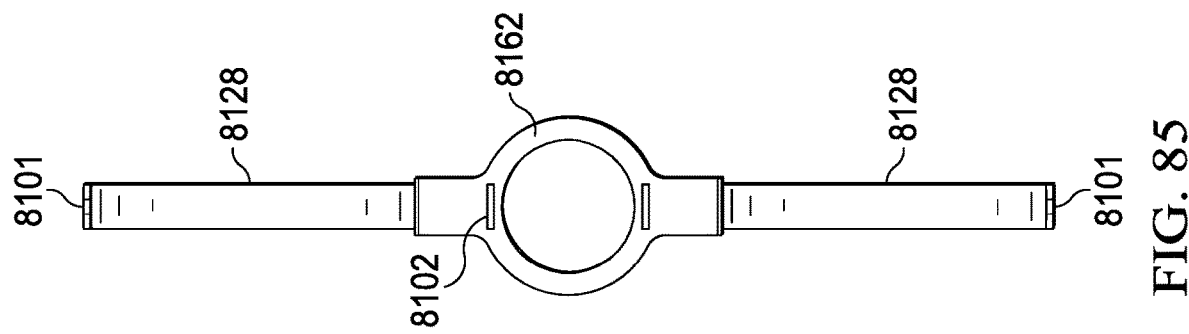
FIG. 85 depicts a bottom view of two joined outwardly biased elongate flexible shafts shown in FIG. 84.
Figure 84:
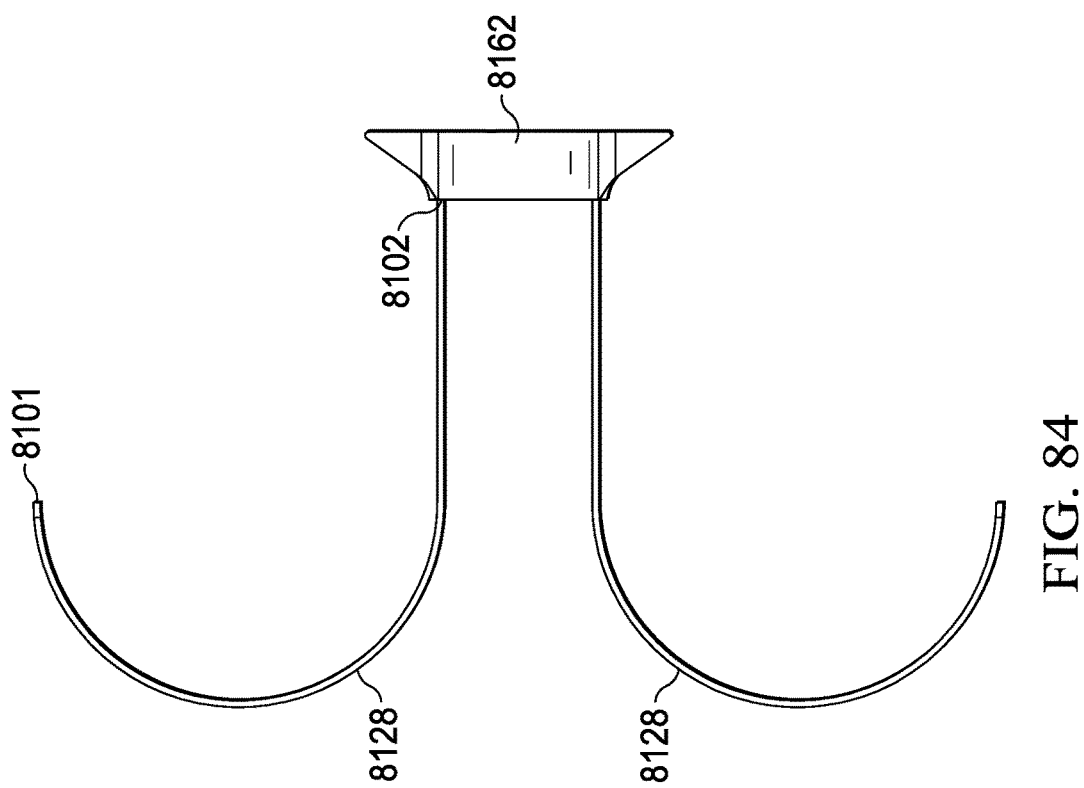
FIG. 84 depicts a side view of two joined outwardly biased elongate flexible shafts configured to be embedded within fin cavities of the alternate embodiment of a surgical cannula device shown in FIG. 81.

Referring now to FIG. 84 and FIG. 85, depicting a side view and a bottom view, respectively, of an embodiment of the outwardly-biased elongate shafts (8128) embedded within flexible fins of the cannula device (see FIGS. 30-31, showing examples of how the shafts are embedded within the flexible fins of another embodiment of a cannula device). The lengths, thickness, and materials used for the shafts of the cannula device may be selected based on the particular type of surgery in which they are intended for use, and the particular anatomy of the patient for which they are intended for use. In one embodiment, the shafts (8128) are constructed of Nitinol and are joined at a proximal end (8102) by a shaft collar (8162) that is constructed of a polycarbonate material that is configured to be mounted at a proximal end of the cannula device. In one embodiment, the distal tips (8101) of the elongate shafts (8128) are configured to protrude from the hollow distal ends (8103) of the flexible fins (8126) (see example of how the tips of the shafts may protrude from the distal tips of the flexible fins as shown in connection with another embodiment of the cannula device at FIG. 30).

Figure 86:
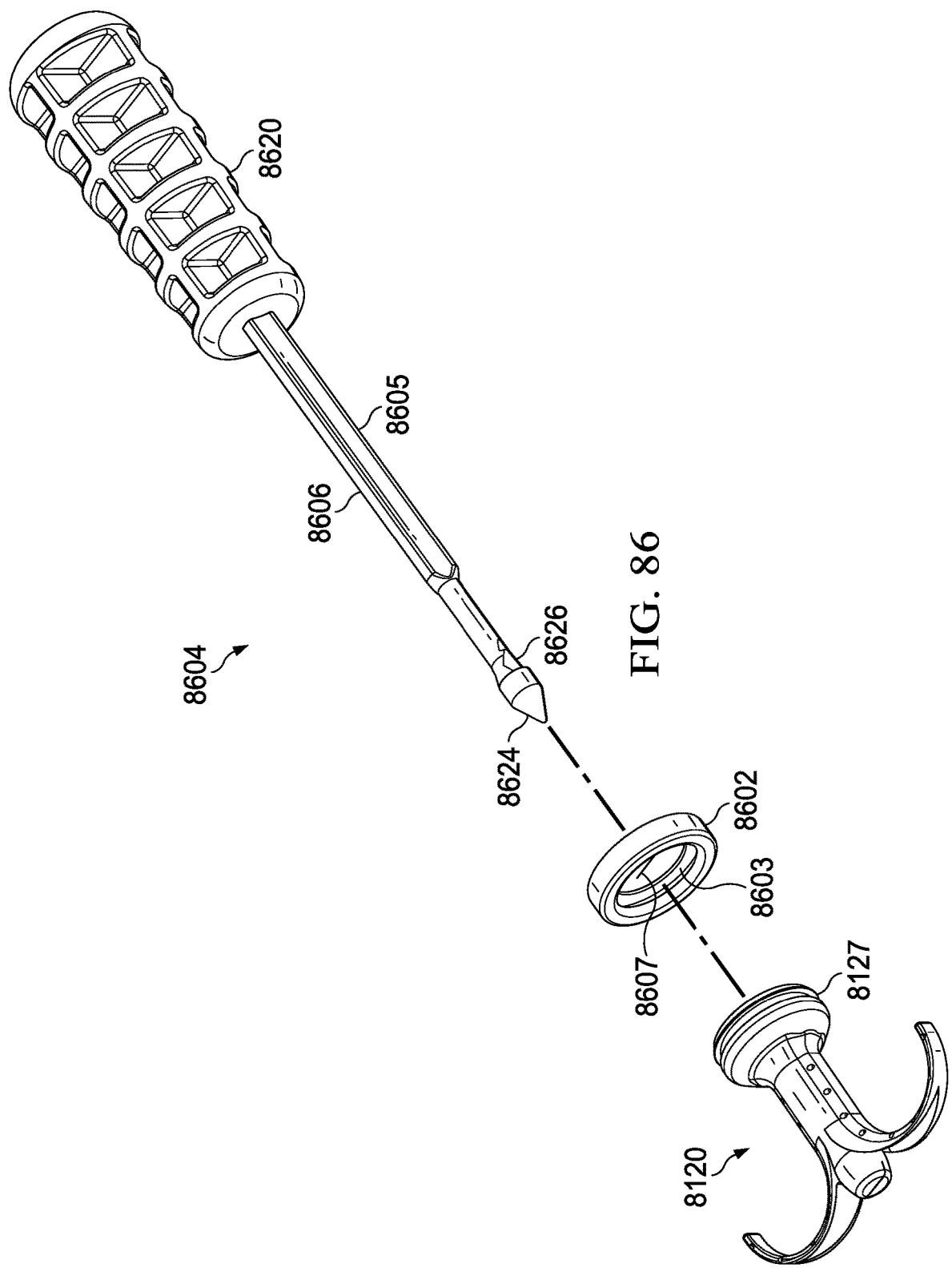
FIG. 86 depicts a perspective view of the alternate embodiment of a surgical cannula device shown in FIG. 81, illustrating how a disc shaped fluid gate may be mounted on a proximal end of said device, and further showing how such device may be mounted on an embodiment of an obturator assembly.

Referring now to FIG. 86, depicting an exploded view of the alternate embodiment of a surgical cannula device having an internal fluid fate as depicted in FIG. 81, and an embodiment of an obturator assembly on which the cannula device may be mounted for deployment. In one embodiment, a disc shaped proximal fluid retention gate (8602), which in one embodiment may be constructed of a medical grade silicone rubber having a 50 Shore A hardness, is configured to be mounted to the proximal end of the surgical cannula device (8120). In one embodiment, the proximal fluid retention gate (8958) has a centrally located slit opening formed in a flexible membrane, and is mountable to the proximal end of the surgical cannula via an annular channel (8127) formed on such collar, which is configured to mate with a correspondingly shaped protrusion and channel formed on the fluid gate. The proximal fluid gate (8602), which in one embodiment is constructed of a flexible polymer, provides for additional fluid retention during surgery.

Still referring now to FIG. 86, the surgical cannula device (8120) and proximal fluid gate (8602) are configured to be mounted on an obturator assembly (8604) prior to deployment to a surgical site in much the same manner as has been described above with respect to the embodiment depicted at FIG. 33. An obturator handle (8620) having a distally extending shaft (8605) terminates at a distal obturator tip (8624). Slots (8626) are formed adjacent to the obturator tip for securing the distal tips of the elongate shafts of the surgical cannula device prior to deployment (see FIG. 88).

Now referring now to FIG. 87, the embodiments of the surgical cannula device (8120) and proximal fluid gate (8602) depicted in FIG. 86, are shown mounted to the embodiment of the obturator assembly (8604) also depicted in FIG. 86. In the embodiment of the surgical cannula device depicted, the flexible fins are shown in a deployed mode, the elongate shafts embedded within such fins outwardly flexing the fins. A support sleeve (8605) having a plurality of raised lobes is mounted on the obturator shaft, between the distal end of the obturator handle and the obturator tip (8624). The support sleeve has an outer diameter greater than the diameter of the obturator shaft, and acts as a support surface upon which the internal fluid gate (8122) may rest prior to fin deployment. The obturator handle (8620) may have notches and other textured features formed on the surface of the handle to aid the user in maintaining a secure grip on the obturator assembly. As noted above, the flexible slit opening located at the distal end of the internal fluid gate (8122) is configured to conform around the shape of the instruments as depicted in FIG. 87, forming a seal around the instruments to aid in fluid retention when positioned within or adjacent to the surgical site. When the instruments are removed from the internal fluid gate, the sides of the slit opening close, preventing fluid leakage. In some embodiments, the distal tips of the shafts embedded within the fins do not protrude from the distal tips of the fins which in such embodiments, said distal tips of said fins are not required to be hollow. In other embodiments, the distal tips of the embedded shafts protrude from hollow distal tips of the fins in the manner depicted in FIGS. 30-32. In some embodiments, the elongate shafts are embedded in the flexible fins and extend proximally to the proximal end of the cannula device. In other embodiments, it is contemplated that the elongate biased shafts may be embedded only in a portion of the flexible fins and not extend proximally to the proximal end of the cannula device body. In one embodiment of the cannula device, the flexible fins are embedded in cavities within the flexible fins, said cavities running a length of said fins from distal tips of the fins to adjacent to the point or section of the cannula body where the branches of the fins split from body of the cannula device.

Figure 88:
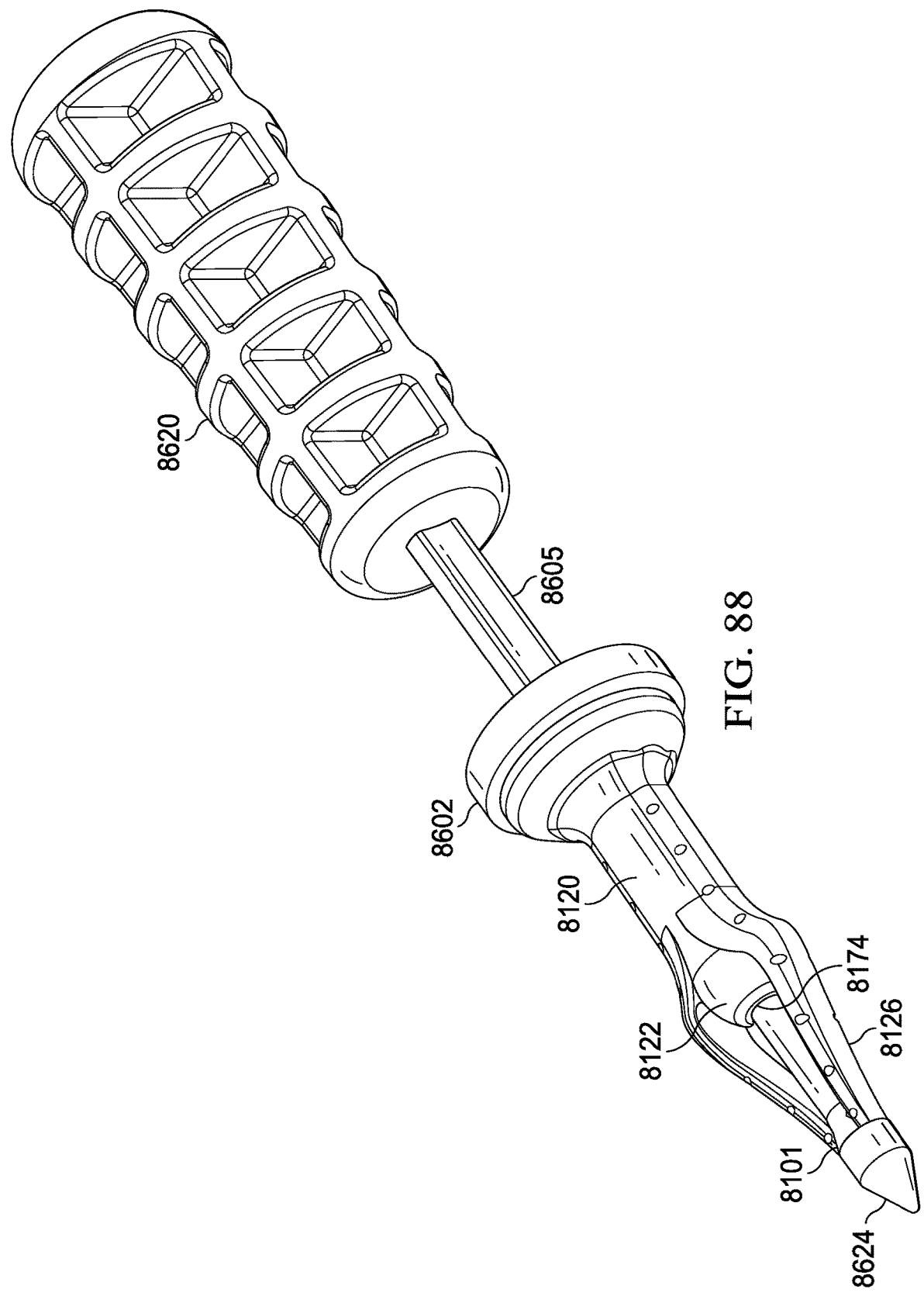
FIG. 88 depicts a perspective view of the alternate embodiment of a surgical cannula device shown in FIG. 86, mounted on an obturator assembly, the distal tips of the flexible shafts secured within the obturator tip.

Now referring now to FIG. 88, the embodiments of the surgical cannula device (8120) and proximal fluid gate (8602) depicted in FIG. 86, are shown mounted to the embodiment of the obturator assembly (8604) also depicted in FIG. 86, with the distal tips (8101) of the elongate shafts (8128) of the cannula device secured within the slots formed adjacent to the obturator tip (8624). In alternate embodiments, the surgical cannula device may be mounted on other embodiments of an obturator assembly configured as discussed herein.

Figure 89:
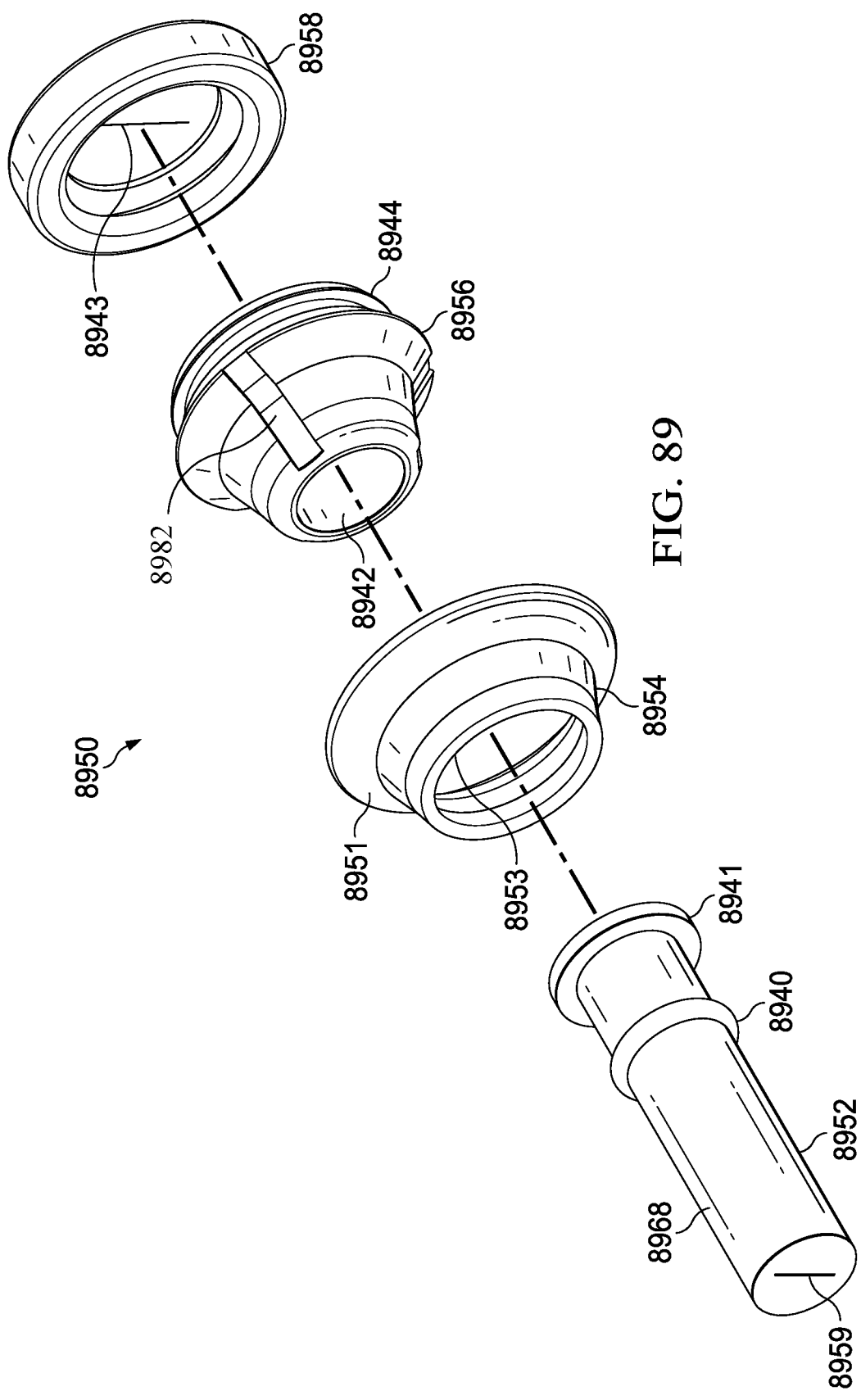
FIG. 89 depicts an exploded view of an alternate embodiment of a portal holder assembly (portal holder flexible fins not shown)
Figure 90:
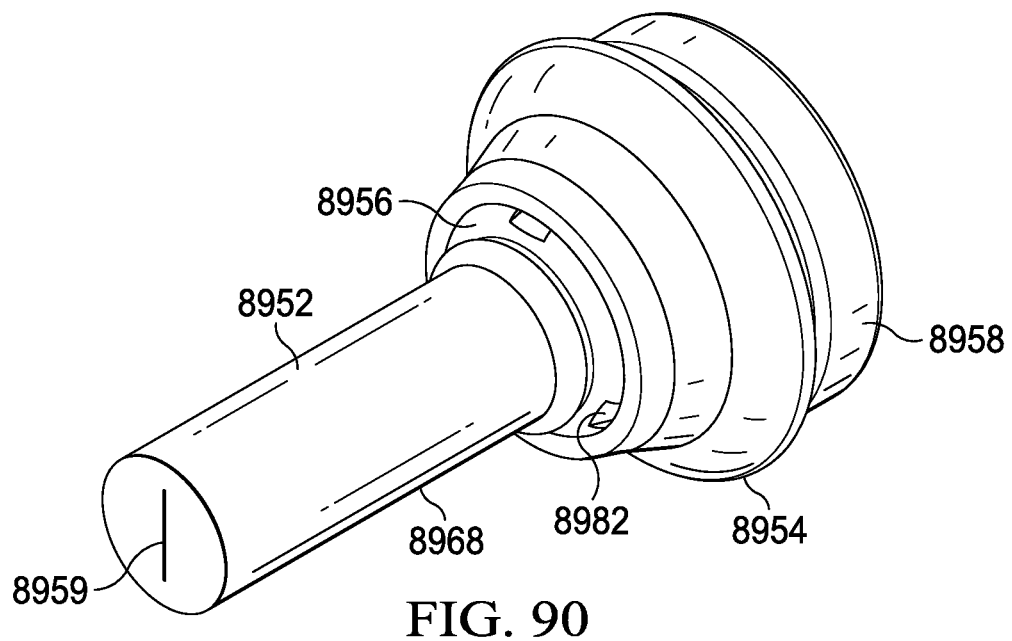
FIG. 90 depicts a perspective view of the alternate embodiment of a portal holder assembly shown in FIG. 89.
Figure 91:
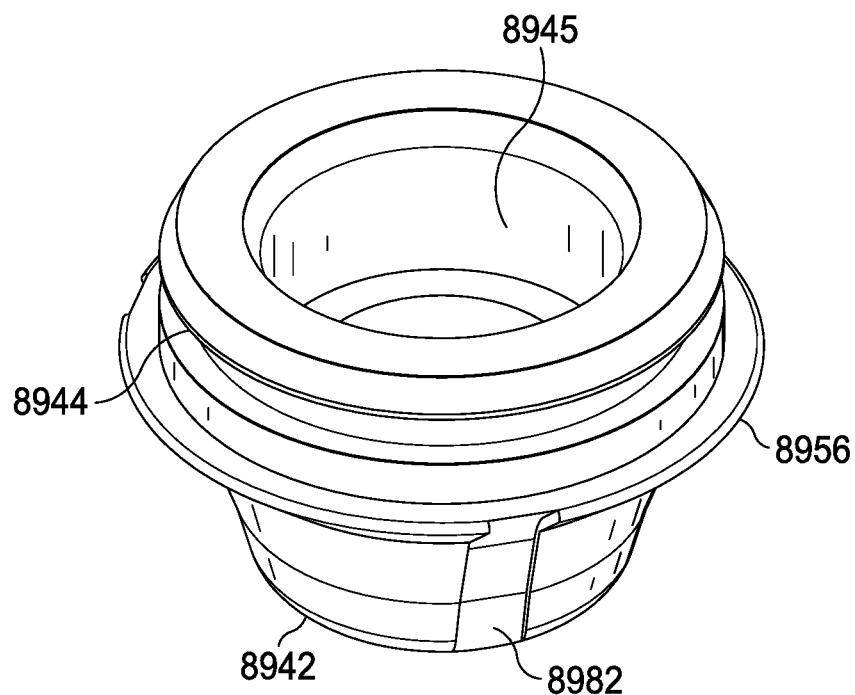
FIG. 91 depicts a perspective view of the collar (proximal end of said collar pointed upwards) of the embodiment of a portal holder assembly shown in FIG. 89 and FIG. 90.
Figure 92:
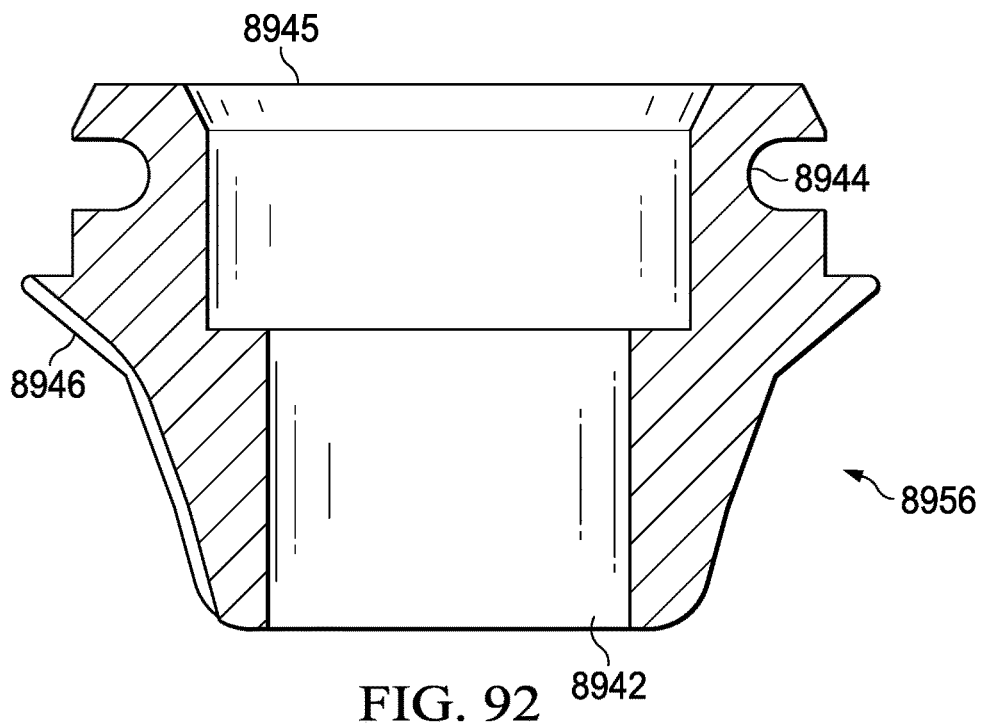
FIG. 92 depicts a cross-sectional view of the collar (proximal end of said collar pointed upwards) of the embodiment of a portal holder assembly shown in FIG. 89 and FIG. 90.
Figure 93:
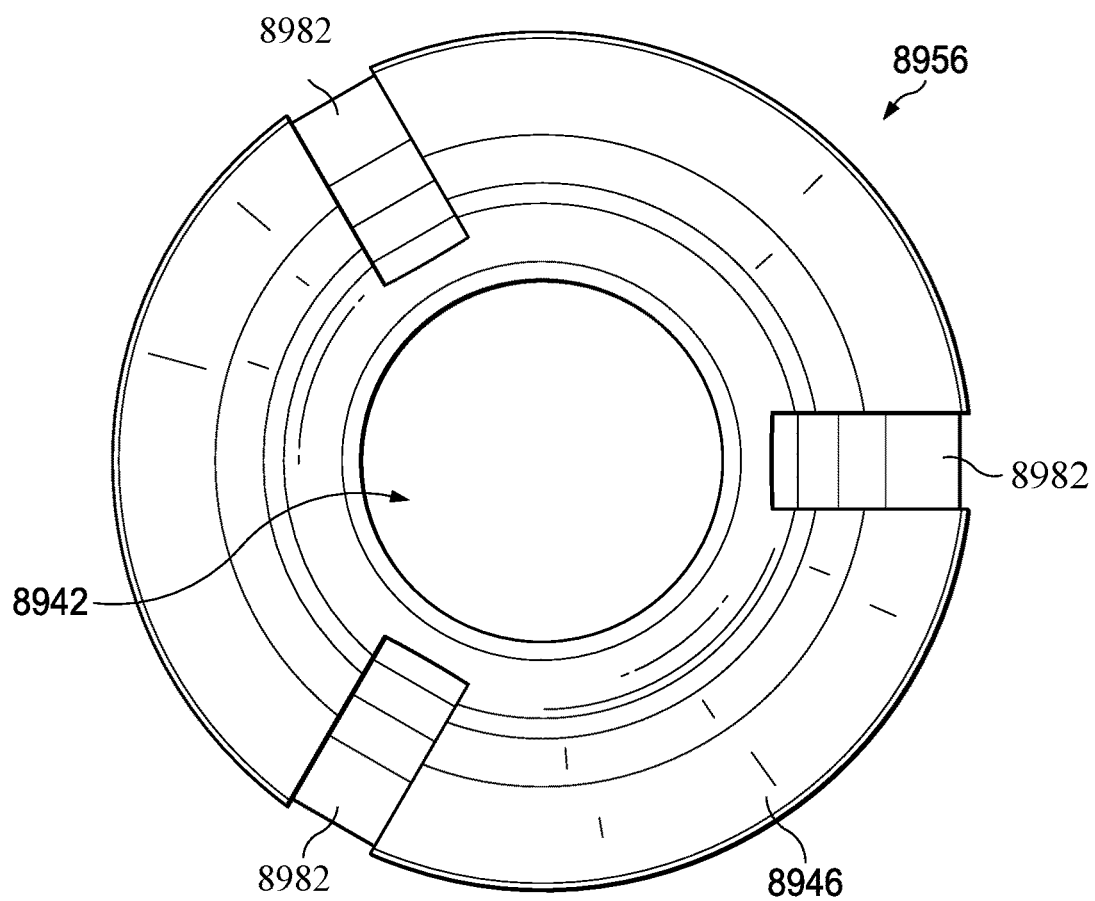
FIG. 93 depicts a top view of the collar (proximal end of said collar pointed upwards) of the embodiment of a portal holder assembly shown in FIG. 89 and FIG. 90.
Figure 96:
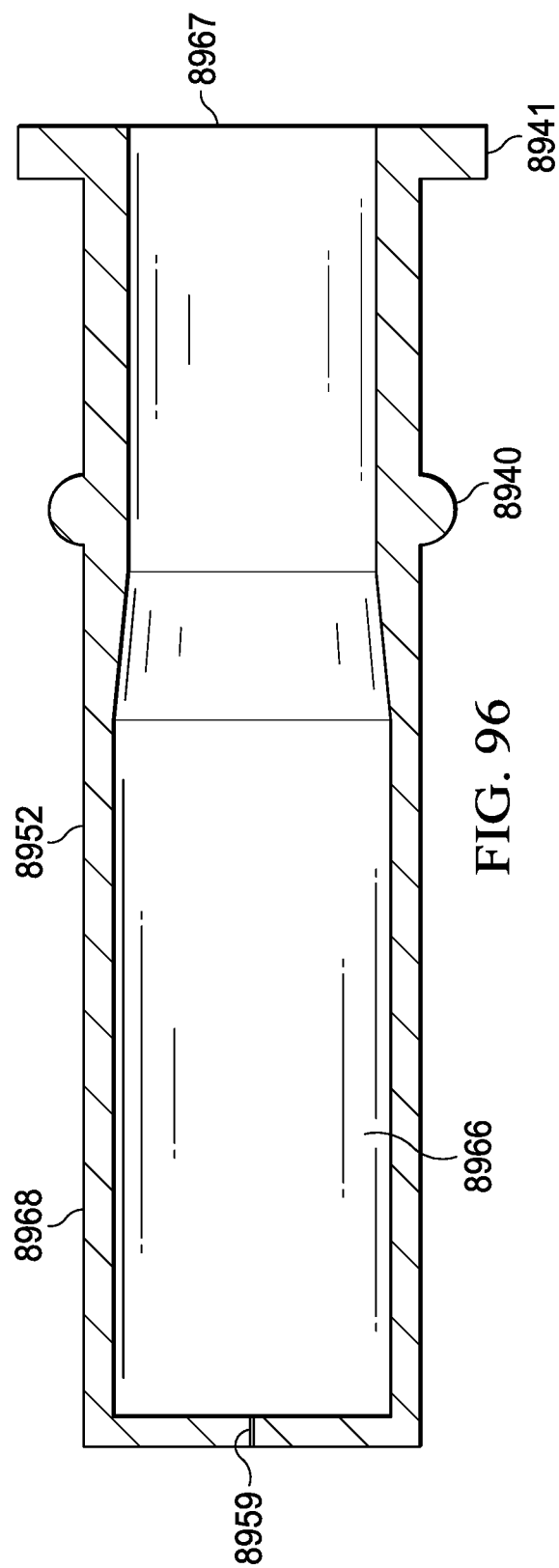
FIG. 96 depicts a cross-sectional view of the distal fluid gate of the embodiment of a portal holder assembly depicted in FIG. 89 and FIG. 90.
Figure 97:
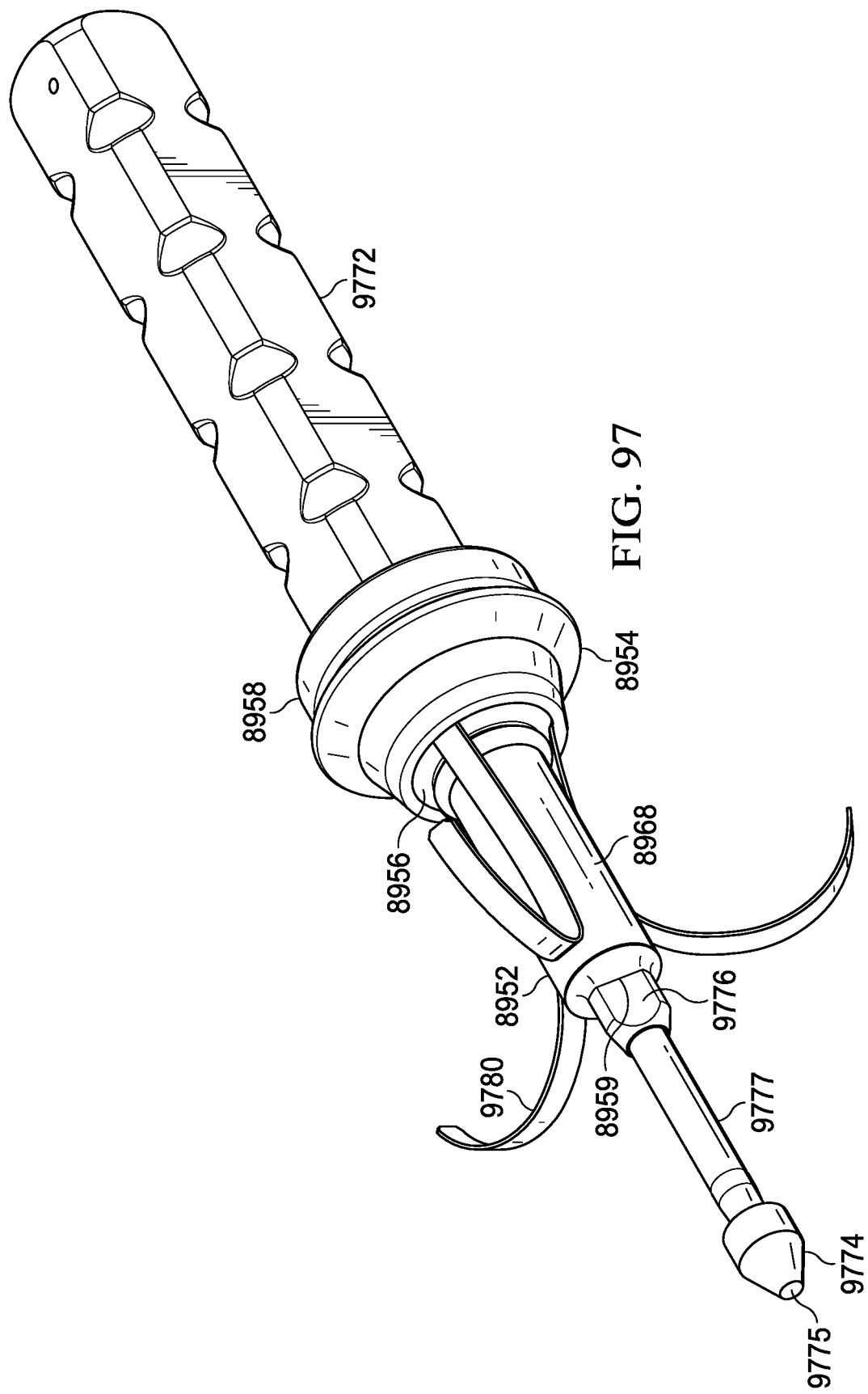
FIG. 97 depicts a perspective view of the alternate embodiment of a portal holder assembly as depicted in FIG. 89 and FIG. 90, shown with mounted portal holder flexible fins, all of which are mounted on an embodiment of the cannulated obturator assembly depicted in FIG. 75.

Referring now to FIG. 89 and FIG. 90, depicting an exploded view and perspective view, respectively, of a further alternate embodiment of a portal holder assembly (portal holder flexible fins not shown—see FIG. 97 showing portal holder flexible fins attached to portal holder assembly) for mounting onto an obturator assembly. The alternate embodiment of the portal holder assembly (are comprised of a portal holder collar or "base member" (8956) having a body with a central lumen formed by the inner walls of the collar. In one embodiment, an outer surface of a proximal portion of the collar is outwardly tapered to deflect the proximal ends of flexible shafts away from the proximal end of the collar aperture. This outward tapering causes the proximal portion of the shafts to be deflected away from the proximal opening of the collar or "base member." In this manner, the degree of possible unwanted contact by the shafts (for example, with the hands of the surgeon and/or surgical instruments) is decreased. A plurality of channels (8982) are formed on the outer surface of the portal holder collar (8956), said channels being shaped and sized to correspond to the shape and size of the portal holder fins which are insertable into such channels and are configured to slide proximally and distally within such channels (allowing the working length of the flexible fins to be adjusted by the user). A fin retention skirt (8954) is configured to be mounted and nested onto the portal holder collar (8956) as depicted in FIG. 90 and FIG. 97. When the portal holder flexible fins are inserted into one of the plurality of channels (8982), the tight-fitting skirt secures the flexible fins to the collar, which also permits for user adjustments to fin working length (length of each respective fin or other flexible shaft, as measured along said fin, from the distal end of the collar/base member, to the distal end of the fin) by sliding the fins through the channels in a proximal and/or distal direction. In one embodiment, a distal (also referred to as an "internal fluid gate" because of its internal position inside patient when in use in some embodiments) hollow fluid retention gate (8952) having a substantially cylindrical shape is constructed of a flexible polymer and has a distally-located slit opening (8959), said fluid retention gate being mountable to the inner walls of the portal holder collar (8956). Raised annular protrusions (8940, 8941) formed around the proximal portion of the curved outer surface (8968) of the fluid retention gate, which allow the gate to be secured to the inner walls of the collar (see internal walls of collar depicted in FIG. 92), which also include correspondingly formed internal wall structures configured to mate with the gate's raised rings to secure said gate to said collar. A disc shaped proximal fluid retention gate (8958), which in one embodiment may be constructed using a medical grade silicone rubber having a 50 Shore A hardness, has a centrally located flexible slit opening formed on an impermeable rubber membrane, and is mountable to the proximal end of the portal holder collar via an annular channel (8944) formed on such collar, and provides for additional fluid retention during surgery. The flexibility of the membrane and slit opening is such that surgical instruments can be slid through the slit opening in a distal and proximal direction, yet retain the ability to retain a significant amount of fluid. One advantage of the alternate embodiment of the portal holder device appearing in FIGS. 89-97 is the use of a proximal fluid retention gate Referring now to FIG. 91, FIG. 92, and FIG. 93, depicting a perspective view of the proximal portion of the collar (8956), a cross-sectional view of the collar (8956) (proximal end pointing upwards), and a top view of the collar (8956), respectively, of the embodiment of a portal holder assembly (portal holder flexible fins not shown) depicted in FIG. 89 and FIG. 90. An annular channel (8944) is formed around the proximal end of the collar, which allows for the mounting of the proximal fluid retention sleeve depicted in FIG. 89, said proximal fluid retention sleeve having an annular rim and channel configured to mate with the channel on the proximal end of the collar so as to be removably secured thereto. A slit opening (8943) formed on the center of the proximal fluid retention sleeve (8958) provides for the passage of surgical instruments while aiding in fluid retention. The proximal retention sleeve provides for additional fluid retention in addition the fluid retention provided by the distal hollow fluid retention sleeve (8954). In one embodiment of the distal fluid retention sleeve, the sleeve is constructed of a flexible polymer material. As discussed above, a plurality of channels (8982) are formed around the outer surface of the portal holder collar (or "base member"), each channel being sized and shaped to receive a correspondingly shaped and sized portal holder flexible fin, which are configured to slide through such respective channels (in a proximal and distal direction) into which they are mounted so that the working length of such fins can be adjusted by the surgeon or other user. Each channel (8982) has a distal end and a proximal end, and an "open length," which is the length of the channel that is exposed and, when a fin retention skirt is mounted on the collar or "base member," is covered by the inner wall of the skirt and prevents a elongate shaft from moving in a manner other than a distally or proximally directed sliding motion within the channel. The cross-sectional view of the collar appearing in FIG. 92 depicts the internal wall structures inside such collar, which provide for the mounting of the distal fluid retention sleeve (8952) via the raised annular protrusions (8940, 8941) as shown in FIG. 96.

Figure 94:
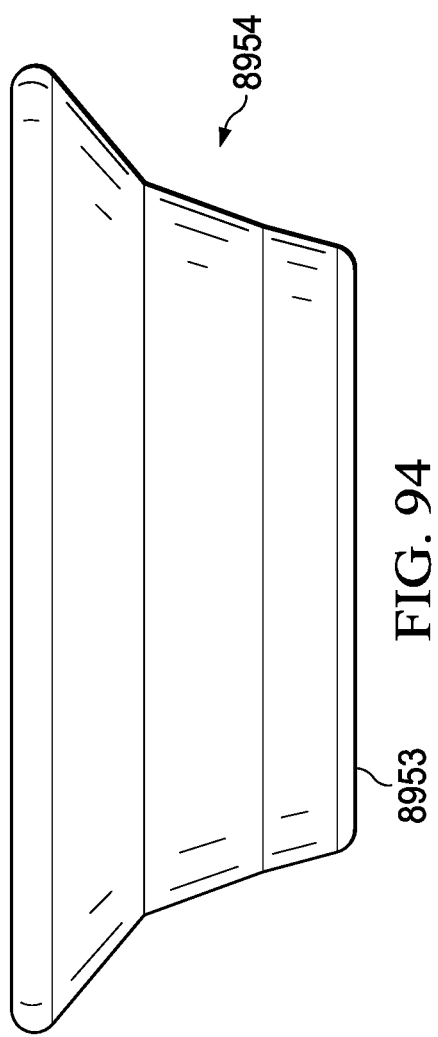
FIG. 94 depicts a side view of the fin retention skirt of the embodiment of a portal holder assembly depicted in FIG. 89 and FIG. 90.
Figure 95:
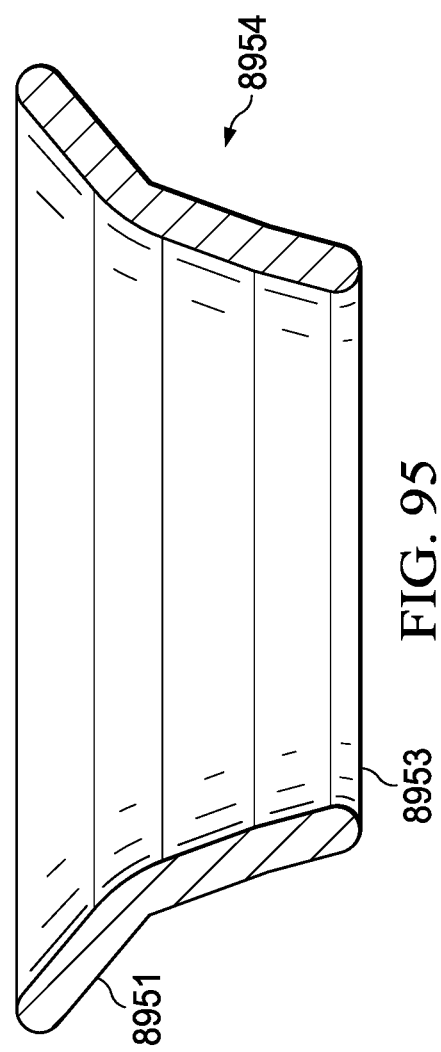
FIG. 95 depicts a cross-sectional view of the fin retention skirt of the embodiment of a portal holder assembly depicted in FIG. 89 and FIG. 90.

Referring now to FIG. 94 and FIG. 95, depicting a side view and a cross-sectional view, respectively, of the fin retention skirt (8954) of the embodiment of a portal holder assembly (portal holder flexible fins not shown) depicted in FIG. 89 and FIG. 90. The fin retention skirt (8954) is sized and shaped to mount on the portal holder collar (8956) as depicted in FIG. 90 and FIG. 97. The fin retention skirt (8954) is tightly mounted to the collar so as to cover the channels (8982) and thereby secure the portal holder fins within such channels, while still allowing a user to adjust the working lengths of the fins by sliding the fins within such channels (8982) in a proximal and distal direction. In one embodiment, the fin retention skirt is configured to rest on top of, or "nest," on the distal portion of the collar. The inner walls of the skirt (8954) are shaped to correspond and mate with the shape of the outer surface of the proximal portion of the collar (8956). For example, the proximal portion of the inner walls of the skirt taper outwardly to correspond to the outwardly tapered proximal portion (8946) of the collar (8956) on which it is configured to be mounted. In other embodiments of the collar and skirt, each structure may be configured to be removably attached to one another. For example, in one embodiment, portions of the outer surface of the collar and portions of the inner walls of the skirt may be threaded such that the skirt and collar may be threadedly fastened to one another.

Referring now to FIG. 96, depicting a cross-sectional view of the distal fluid gate of the embodiment of a portal holder assembly (portal holder flexible fins not shown) depicted in FIG. 89 and FIG. 90. A slit opening (8959) is formed on the distal end of the distal fluid retention gate and provides for the passage of surgical instruments while aiding in fluid retention. The distal fluid gate includes a central lumen (8966) having a proximal opening (8967) thereto. One or more annular protrusions (8940, 8941) are formed on the outer surface (8968) of the distal fluid gate. As noted above, such annular protrusions are configured to mate with correspondingly shaped structures formed on the internal walls of the collar to removably secure such gate to the collar. In one embodiment of the distal fluid retention gate, the sleeve is constructed of a flexible polymer material.

Referring now to FIG. 97, depicting a perspective view of the alternate embodiment of a portal holder assembly as depicted in FIG. 89 and FIG. 90, shown with mounted portal holder flexible fins, all of which are mounted on an embodiment of the cannulated obturator assembly depicted in FIG. 75. The fin retention skirt (8954) is mounted onto and around the top portion of the portal holder collar (8956) and secures the flexible fins (9780) within the collar channels (not shown). A distal fluid retention gate (8952), when mounted to the collar, extends distally and has a slit opening (8959) formed on its distal end, allowing for the passage of the obturator shaft and obturator tip, as well as surgical instruments and other objects used during surgery, while aiding in fluid retention. The distal fluid retention gate (8952), while flexible enough to provide for the slit (8959) to be penetrated by an obturator shaft or surgical instrument with minimal force, must still be structurally rigid enough to not deform due to inward forces exerted by the flexible fins bearing against it as depicted in FIG. 97. The flexible fins are configured to slide, when a pushing or pulling force is applied by a user, within the channels (8982) of the collar even when secured by the fin retention skirt (8954). While not shown in FIG. 97, the distal tips of the alternate embodiment of the portal holder assembly are configured to be secured within the hood of the obturator tip (9774) prior to deployment of such fins (see FIG. 73 and FIG. 88, showing examples of how the distal tips of flexible fins may be secured within the obturator tip prior to deployment of such fins). It should also be noted that while the embodiment of the portal holder device shown in FIG. 97 is depicted as having three flexible fins, the portal holder device may be configured to utilize a greater or lesser number of flexible fins in alternate embodiments of the device. For example, in one alternate embodiment, the portal device may include a collar (base member) having six channels such that six flexible fins could be mounted to the portal holder device, which in some surgical procedures could provide for needed additional soft tissue retraction and compression.

Still referring now to FIG. 97, a support sleeve (9776) having a plurality of raised lobes is mounted on the cannulated obturator shaft (9777), between the distal end of the obturator handle (9772) and the obturator tip (9774). The support sleeve has an outer diameter greater than the diameter of the obturator shaft, and acts as a support surface upon which the distal sleeve (8952) and portal holder flexible fins (9780) may rest prior to fin deployment (the fins are actually resting on the outer surface (8968) distal sleeve, but the support sleeve nonetheless supports such fins. As has been previously discussed above, the portal holder flexible fins (9780) are mounted to the portal holder collar via channels (may also be referred to as "slots") on the outer collar wall, which allow the user to slide the fins distally and proximally to adjust the working lengths of the fins according the needs of the user and the anatomy of the surgical site. The obturator handle (9772) may have notches and other textured features formed on the surface of the handle to aid the user in maintaining a secure grip on the obturator assembly.

Referring to FIGS. 89-97, disclosed herein in one embodiment is a surgical device (8950) for providing soft tissue retraction and fluid retention during surgical procedures, said surgical device comprising: a base member (8956) having an aperture extending from a proximal end to a distal end; and a plurality of flexible shafts (9780) disposed within channels (8982) formed an outer surface of said base member, each of said plurality of flexible shafts having a distal end, and a proximal end, and a working length, said channels each having an open length, wherein a skirt member having a proximal end and a distal end is configured to be mounted on and be nested over at least a distal portion of said base member such that the skirt member covers all or a portion of the open lengths of said channels, and wherein said working length of each of said plurality of flexible shafts is a length of each respective flexible shaft, as measured along said respective flexible shaft, from said distal end of said base member to said distal end of said respective flexible shaft, wherein said distal ends of said plurality of flexible shafts are naturally biased in an outward direction, wherein an outer surface (8946) of said proximal end of said base member is outwardly tapered to deflect said proximal ends of each of said plurality of flexible shafts away from an opening to said aperture adjacent to said proximal end of said base member, wherein a user grasping and applying a force to the proximal end of one of said plurality of flexible shafts causes said respective flexible shaft to slide in a proximal direction or a distal direction respective to said base member, thereby allowing the user to increase and decrease said working length of said respective flexible shaft, wherein each of said plurality of flexible shafts is capable of sliding in the proximal direction with respect to said base member such that the respective proximal end of each of said plurality of flexible shafts protrudes past said proximal end of said base member. In one embodiment of the surgical device, a gap between said plurality of flexible shafts at a convergence point may be varied by the user by increasing or decreasing the working lengths of said plurality of flexible shafts. In another embodiment of the surgical device, the surgical device may further comprise a substantially cylindrical hollow fluid gate (8952) having a slit opening (8959) formed on a distal end, and a second opening on a proximal end, a proximal portion of the fluid gate being removably or integrally attached to an inner wall of the base member, said fluid gate having a length that extends in a distal direction. In another embodiment of the surgical device, the surgical device may further comprise a disc shaped fluid gate (8958) having a slit opening (8943) formed on a membrane covering of said gate, the disc shaped fluid gate being configured to be removably or integrally attached to the proximal end of the base member.

As previously noted above, it is emphasized that while the device embodiments described herein may be used during shoulder arthroscopy, one of ordinary skill will understand that these surgical devices may also be employed in essentially any arthroscopic, laparoscopic, or endoscopic surgery, as well as any other type of surgery, and in connection with surgery on any type of anatomical structure requiring the surgeon to establish a working port in the tissue of a patient. Moreover, it should be noted that alternate embodiments of the devices and assemblies discussed herein may be utilized to perform surgery on subjects other than humans such as, for example, animals such as dogs, cats and livestock. Those of ordinary skill in the art will recognize that the dimensions of the device embodiments discussed herein will require modification depending upon the anatomical structures of the particular subject of the surgery in which the invention is utilized, as wells as the type of surgery being performed.

The inventions may be embodied in other specific forms without departing from the spirit or essential characteristics thereof. The present embodiments are therefore to be considered in all respects as illustrative and not restrictive. Accordingly, the scope of the inventions are established by the appended claims rather than by the foregoing description. All changes that come within the meaning and range of equivalency of the claims are embraced therein. Further, the recitation of method steps does not denote a particular sequence for execution of the steps. Such method steps may therefore be performed in a sequence other than that recited unless the particular claim expressly states otherwise.

I claim:

1. A cannula for surgical procedures, the cannula comprising:
    a body member having an inner wall forming a lumen along at least a proximal portion of a length of said body member to form a port for a surgical tool, said inner wall and an outer wall of said body member being split to form branches at a distal end of said lumen so as to form a plurality of flexible fins,
    wherein a cavity is disposed within each of said plurality of flexible fins,
    wherein an elongate shaft is embedded within each of said cavities, and
    wherein a hollow internal fluid gate having a second lumen is formed between said plurality of flexible fins at a junction of proximal ends of said plurality of flexible fins adjacent to where said body member is split to form the plurality of flexible fins, said hollow internal fluid gate having a protrusion extending in a distal direction away from said junction and terminating with a distal slit opening.

2. The cannula of claim 1, wherein each elongate shaft is naturally biased in an outward direction.

3. The cannula of claim 1, wherein a distal tip of each elongate shaft protrudes from a distal end of the respective cavities in which each of said elongate shaft is embedded within.

4. The cannula of claim 1, wherein each elongate shaft comprises a polymer.

5. The cannula of claim 1, wherein each elongate shaft comprises a shape memory alloy.

* * * * *